United States Patent [19]
Villalobos et al.

[11] Patent Number: 5,750,542
[45] Date of Patent: May 12, 1998

[54] BENZISOXAZOLE AND BENZISOTHIZOLE DERIVATIVES AS CHOLINESTERASE INHIBITORS

[75] Inventors: Anabella Villalobos, Niantic; Arthur A. Nagel, Gales Ferry; Yuhpyng L. Chen, Waterford, all of Conn.

[73] Assignee: Pfizer, New York, N.Y.

[21] Appl. No.: 127,847

[22] Filed: Sep. 28, 1993

Related U.S. Application Data

[63] Continuation-in-part of PCT/US92/01605 Mar. 9, 1992.

[51] Int. Cl.[6] .............. C07D 413/12; C07D 413/06; A61K 31/445
[52] U.S. Cl. .............. 514/322; 546/199; 546/198; 546/209; 548/207; 548/241; 514/321
[58] Field of Search ............... 546/209, 199, 546/198; 548/207, 241; 514/321, 322

[56] References Cited

U.S. PATENT DOCUMENTS

| | | | |
|---|---|---|---|
| 4,112,105 | 9/1978 | Carlson et al. | 424/270 |
| 4,122,176 | 10/1978 | Katsube et al. | 424/250 |
| 4,458,075 | 7/1984 | Davis et al. | 546/198 |
| 4,458,076 | 7/1984 | Strupczewski et al. | 546/199 |
| 4,461,894 | 7/1984 | Omodei--Sale et al. | 544/370 |
| 4,528,376 | 7/1985 | Strupczewski et al. | 546/198 |
| 4,604,395 | 8/1986 | Davis et al. | 514/255 |
| 4,698,346 | 10/1987 | Musser | 514/293 |
| 4,806,649 | 2/1989 | Strupczewski | 546/193 |
| 4,963,677 | 10/1990 | Sellin | 544/247 |
| 5,100,902 | 3/1992 | Peglion et al. | 514/321 |
| 5,364,866 | 11/1994 | Strupczewski | 514/321 |

FOREIGN PATENT DOCUMENTS

| | | |
|---|---|---|
| 0091511A2 | 10/1983 | European Pat. Off. . |
| 0229391A1 | 7/1987 | European Pat. Off. . |
| 0296560A2 | 12/1988 | European Pat. Off. . |
| 0326106 | 8/1989 | European Pat. Off. . |
| 0330026 | 8/1989 | European Pat. Off. . |
| 0378207 | 7/1990 | European Pat. Off. . |
| 0383318 | 8/1990 | European Pat. Off. . |
| 0401715 | 12/1990 | European Pat. Off. . |
| 428437A1 | 5/1991 | European Pat. Off. . |
| 3002155 | 1/1990 | Japan . |
| 2169569 | 6/1990 | Japan . |
| 2212459 | 8/1990 | Japan . |
| 9217475 | 10/1992 | WIPO . |
| 9304063 | 3/1993 | WIPO . |

OTHER PUBLICATIONS

Adger et al., "1,2,3-Benzotriazines," *J. Chem. Soc. Perkin Trans. I*, pp. 31–40 (1975).
Appel, Stanley H., "Alzheimer's Disease," *Neurology*, 6, pp. 312–317, Month and Year Not Available.
Bartsch et al., "Phase Transfer Catalyzed Synthesis of Indazoles from o-Alkylbenzenediazonium Tetrafluoroborates," *J. Heterocyclic Chem.*, 21, pp. 1063–1064 (1984); (Jul.–Aug.).
Becker et al., "Mechanisms of Cholinesterase Inhibition In Senile Dementia of the Alzheimer Type," *Drug Development Research*, 12, pp. 163–195 (1988).

Behr et al., "Pyrazoles, Pyrazolines, Pyrazolidines, Indazoles, and Condensed Rings," *Heterocyclic Compounds*, pp. 289–382 (1967).
Claramunt et al., "Synthesis By Phase Transfer Catalysis of N-Benzyl, N-diphenyl-Methyl and N-Triphenylmethyl Azoles and Benzazoles: Proton NMR and Chromatographic Data as a Tool for Identification," *Heterocycles*, 23, No. 11, pp. 2895–2906 (1985).
Crabbe et al., "Unusual Base-induced Transformations of 2',6'-Dihydroxyacetophenone Oxime," *J. Chem. Soc. Perkin I*, pp. 2220–2225 (1973).
Higashino, Takeo, "Takeo Higashino: On the Reaction of 4-Quinazolinecarbonitrile with Nucheophilic Reagents. II. Reaction of 4-Quinzaolinecarbonitrile with Grignard Reagents," *Chem. Pharm. Bull.*, 10, pp. 1043–1047 (1962).
International Search Report in corresponding International Patent Application No. PCT/US 92/01605, with Notification and one-page annex; Jul. 1992.
Kalkote et al., "New Synthesis of 1,2-Benzisoxazole Derivatives," *Aust. J. Chem.*, 30, pp. 1847–1850 (1977).
Kant et al., "Nature of Reissert Analogs Derived from N,N–Dialkyl and N,N–Diaryl Carbamoyl Chlorides," *J. Heterocycl. Chem.*, 22, pp. 1065–1069 (1985).
McKinnon et al., "Fused Heterocycles From o-acylbenzenethiol Derivatives," *Can. J. Chem.*, 66, pp. 1405–1409 (1988).
Oliver et al., "Alkylation and Rearrangement of Lithiated 3-Methyl-1,2-benzisoxazoles," *J. Org. Chem.*, 54, pp. 4970–4973 (1989).
Ruchardt et al., "Aromatic Didazonium Salts. X.—A One-Pot Procecure for the Jacobson Synthesis of Indazole," *Liebigs Ann. Chem.*, pp. 908–927 (1980).
Thakar et al., "A Modified Method for the Synthesis of 1,2-Benzisoxazoles," *Indian J. Chem.*, 15B, pp. 1058–1059 (1977); Nov.
Uff et al., "Studies with Reissert Compounds, Part 17. Mono–Reissert Compound Formation at the 1,2-Position of the Quinazoline System," *J. Chem. Soc. Perkin Trans. I*, pp. 2295–2303 (1986).
Verboom et al, "'tert-Amino Effect' in Heterocyclic Synthesis. Formation of N-Heterocycles by Ring–Closure Reactions of Substituted 2-Vinyl-N,N–dialkylanilines," *J. Org. Chem.*, 49, pp. 269–276 (1984).

*Primary Examiner*—Johann Richter
*Assistant Examiner*—Laura L. Stockton
*Attorney, Agent, or Firm*—Peter C. Richardson; Paul H. Ginsburg; Karen DeBenedictis

[57] ABSTRACT

Described herein are compounds of the formula

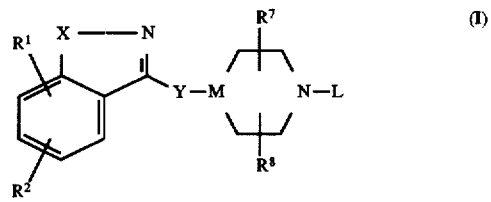

wherein $R^1$, $R^2$, $R^7$, $R^8$, X, Y, M and L are defined as below. The compounds of formula I are cholinesterase inhibitors and are useful in enhancing memory in patients suffering from dementia and Alzheimer's disease.

6 Claims, No Drawings

BENZISOXAZOLE AND BENZISOTHIZOLE DERIVATIVES AS CHOLINESTERASE INHIBITORS

This application is a continuation-in-part of international patent application Ser. No. PCT/US 92/01605 filed Mar. 9, 1992.

BACKGROUND OF THE INVENTION

The present invention relates to heterocyclic-cyclic amine derivatives of the formula I below, and pharmaceutically acceptable salts of such compounds. The compounds of formula I are cholinesterase inhibitors and are useful in enhancing memory in patients suffering from dementia and Alzheimer's disease.

Alzheimer's disease is associated with degeneration of cholinergic neurons in the basal forebrain that play a fundamental role in cognitive functions, including memory. Becker et al., Drug Development Research, 12, 163–195 (1988). As a result of such degeneration, patients suffering from the disease exhibit a marked reduction in acetylcholine synthesis, choline acetyltransferase activity, acetylcholinesterase activity and choline uptake.

It is known that acetylcholinesterase inhibitors are effective in enhancing cholinergic activity and useful in improving the memory of Alzheimer's patients. By inhibiting acetylcholinesterase enzyme, these compounds increase the level of the neurotransmitter acetylcholine, in the brain and thus enhance memory. Becker et al., supra, report that behavioral changes following cholinesterase inhibition appear to coincide with predicted peak levels of acetylcholine in the brain. They also discuss the efficacy of the three known acetylcholinesterase inhibitors physostigmine, metrifonate, and tetrahydroaminoacridine.

European Patent Application EP A 0 229 391 relates to piperidine derivatives of the formula: $R^1$—X—A—$R^2$. European Patent Application EP A 296 560 relates to a cyclic amine compound of the formula

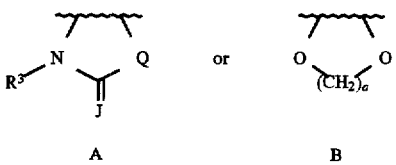

All documents cited herein, including the foregoing, are incorporated herein by reference in their entireties.

SUMMARY OF THE INVENTION

The present invention relates to compounds of the formula

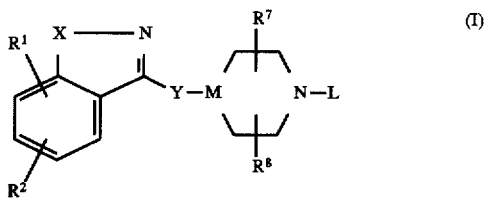

wherein $R^1$ and $R^2$ are independently selected from hydrogen, $(C_1-C_6)$alkoxy, benzyloxy, phenoxy, hydroxy, phenyl, benzyl, halo, nitro, cyano, $COR^5$, —$COOR^5$, —$CONHR^5$, —$NR^5R^6$, —$NR^5COR^6$, —$OCONR^5R^6$, —$NHCOOR^5$, $(C_1-C_6)$alkyl optionally substituted with from 1 to 3 fluorine atoms; $SO_pCH_2$-phenyl or $SO_p(C_1-C_6)$alkyl, wherein p is 0, 1 or 2; pyridylmethyloxy or thienylmethyloxy; 2-oxazolyl, 2-thiazolyl and benzenesulfonamide; wherein the phenyl moieties of said phenoxy, benzyloxy, phenyl, benzyl and benzenesulfonamide groups, the pyridyl and thienyl moieties of said pyridylmethyloxy or thienylmethyloxy and the oxazolyl and thiazolyl moieties of said 2-oxaxolyl and 2-thiazolyl may optionally be substituted with 1 or 2 substituents independently selected from halo, $(C_1-C_4)$alkyl, trifluoromethyl, $(C_1-C_4)$ alkoxy, cyano, nitro and hydroxy.

or $R^1$ and $R^2$, when attached to adjacent carbon atoms and when X is oxygen, sulfur or $NR^4$ wherein $R^4$ is hydrogen or $(C_1-C_4$ alkyl) may form, together with the carbon atoms to which they are attached, a group of the formula

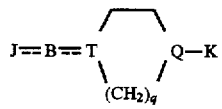

wherein

J is oxygen, sulfur or $NR^4$, "a" is 1 or 2, $R^3$ is hydrogen or $(C_1-C_6)$alkyl and Q is oxygen, sulfur, NH, $CHCH_3$, $C(CH_3)_2$, —CH=CH—, or $(CH_2)_l$ wherein l is an integer from 1 to 3;

X is oxygen, sulfur, —CH=CH—, —CH=N—, —N=CH—, —N=N—, or $NR^4$ wherein $R^4$ is hydrogen or $(C_1-C_4)$ alkyl;

Y is —$(CH_2)_m$—, —CH=CH$(CH_2)_n$—, —$NR^4$ $(CH_2)_m$—, or —O$(CH_2)_m$— wherein $R^4$ is defined as above. n is an integer from 0 to 3 and m is an integer from 1 to 3;

$R^5$ and $R^6$ are each independently selected from hydrogen, $(C_1-C_6)$alkyl, phenyl or benzyl, wherein the phenyl moieties of said phenyl and benzyl may optionally be substituted with 1 or 2 substituents independently selected from fluoro, chloro, bromo, iodo, $(C_1-C_4)$ alkyl, trifluoromethyl, $(C_1-C_4)$ alkoxy, cyano, nitro and hydroxy, or $NR^5R^6$ together form a 4 to 8 membered ring wherein one atom of the ring is nitrogen and the others are carbon, oxygen or nitrogen (e.g. pyrrolidinyl, piperidinyl, morpholino, piperazinyl or N-methylpiperazinyl), or $NR^5COR^6$ together form a 4 to 8 membered cyclic lactam ring;

M is —CH— or nitrogen;

L is phenyl, phenyl-$(C_1-C_6)$alkyl, cinnamyl or pyridylmethyl, wherein the phenyl moieties of said phenyl and phenyl-$(C_1-C_6)$alkyl may optionally be substituted with 1 to 3 substituents independently selected from $(C_1-C_6)$alkyl, $(C_1-C_6)$alkoxy, $(C_1-C_4)$ alkoxycarbonyl, $(C_1-C_4)$alkylcarbonyl, —$OCONR^5R^6$, —$NHCOOR^5$ or halo; or L is a group of the formula

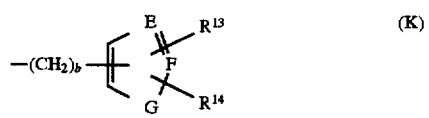

wherein b is an integer from 1 to 4, $R^{13}$ and $R^{14}$ are independently selected from hydrogen, $(C_1-C_4)$ alkyl, halo and phenyl, E and F are independently selected from —CH— and nitrogen, and G is oxygen, sulfur or $NR^4$ wherein $R^4$ is defined as above, with the proviso that when E and F are both nitrogen, one of $R^{13}$ and $R^{14}$ is absent; and $R^7$ and $R^8$ are independently selected from hydrogen, $(C_1-C_6)$alkyl, $(C_1-C_6)$alkoxycarbonyl, $(C_1-C_6)$alkylcarbonyl and $(C_1-C_6)$alkoxy, with the proviso that said $(C_1-C_6)$alkoxy is not attached to a carbon that is adjacent to a nitrogen.

This invention also relates to the pharmaceutically acceptable acid addition salts of compounds of the formula I. Examples of such pharmaceutically acceptable acid addition salts are the salts of hydrochloric acid, p-toluenesulfonic acid, maleic acid, fumaric acid, citric acid, succinic acid, salicylic acid, oxalic acid, hydrobromic acid, phosphoric acid, methanesulfonic acid, tartaric acid, di-p-toluoyl tartaric acid, and mandelic acid.

This invention also relates to a pharmaceutical composition for inhibiting cholinesterase comprising a compound of the formula I or a pharmaceutically acceptable acid addition salt thereof, and a pharmaceutically acceptable carrier.

This invention also relates to a method for inhibiting cholinesterase in a mammal comprising administering to a mammal an amount of a compound of the formula I or a pharmaceutically acceptable acid addition salt thereof effective in inhibiting cholinesterase.

This invention also relates to a method for enhancing memory or treating or preventing Alzheimer's disease in a mammal comprising administering to a mammal an amount of a compound of the formula I or a pharmaceutically acceptable acid addition salt thereof effective in enhancing memory or treating or preventing Alzheimer's disease.

This invention also relates to compounds of the formula

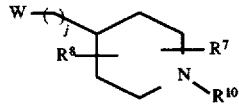

wherein

W is a leaving group; j is an integer from 0 to 2;

$R^{10}$ is a nitrogen protecting group; and $R^7$ and $R^8$ are independently selected from hydrogen, $(C_1-C_6)$ alkyl, $(C_1-C_6)$ alkoxycarbonyl, $(C_1-C_6)$ alkylcarbonyl and $(C_1-C_6)$ alkoxy, with the proviso that said $(C_1-C_6)$ alkoxy is not attached to a carbon that is adjacent to a carbon that is adjacent to a nitrogen. These compounds are useful as intermediates in the synthesis of compounds of the formula I.

This invention also relates to compounds of the formula

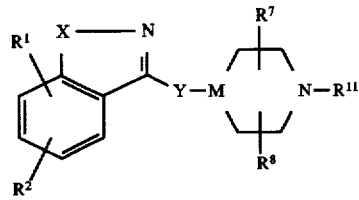

wherein $R^1$, $R^2$, $R^7$, $R^8$, X, Y and M are as defined above and $R^{11}$ is hydrogen or a nitrogen protecting group. These compounds are useful as intermediates in the synthesis of compounds of the formula I.

This invention also relates to compounds of the formula:

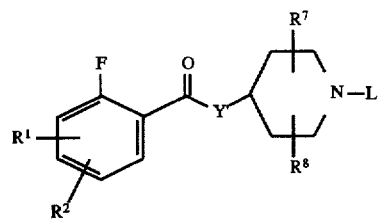

wherein $R^1$, $R^2$, $R^7$, $R^8$ and L are as defined above and Y is —CH=CH—$(CH_2)_n$— or —$(CH_2)_m$—. These compounds are useful as intermediates in the sythesis of compounds of the formula I.

The term "mammal", as used herein, includes humans.

The term "halo", as used herein, includes chloro, bromo, iodo or fluoro.

The term "alkyl", as used herein, unless otherwise indicated, includes saturated monovalent hydrocarbon radicals having straight, branched, or cyclic moieties or combinations thereof.

The term "$(C_1-C_4)$ alkylcarbonyl", as used herein, refers to a substituent of the formula

    V wherein $R^{15}$ is $(C_1-C_4)$ alkyl.

The term "$(C_1-C_4)$ alkoxycarbonyl", as used herein, refers to a substituent of the formula V above, wherein $R^{15}$ is $(C_1-C_4)$ alkoxy.

The term "$(C_1-C_6)$ alkoxycarbonyl", as used herein, refers to a substituent of the formula V above, wherein $R^{15}$ is $C_1-C_6)$ alkoxy.

The term "$(C_1-C_6)$alkylcarbonyl", as used herein, refers to a substituent of the formula V above, wherein $R^{15}$ is $(C_1-C_6)$ alkyl.

Preferred compounds of this invention are compounds of the formula I wherein X is oxygen or sulfur, Y is —$CH_2$—, —$CH_2$—$CH_2$—, M is —CH— and L is benzyl, $R^1$ and $R^2$ are $C_1-C_6$)alkyl, $(C_1-C_6)$alkoxy, $NR^5R^6$, or $NR^5COR^6$, $R^3$ is hydrogen or $(C_1-C_6)$alkyl, J is oxygen or sulfur and Q is $CH(CH_3)$, $CH(CH_3)_2$, —CH=CH or $(CH_2)_1$ and the pharmaceutically acceptable salts of such compounds.

3-[2-[1-(Phenylmethyl)-4-piperidinyl]ethyl]-1,2-benzisoxazole;

5-Methyl-3-[2-[1-(phenylmethyl)-4-piperidinyl]ethyl]-1,2-benzisoxazole;

5,6-Dimethyl-3-[2-[1-(phenylmethyl)-4-piperidinyl]ethyl]-1,2-benzisoxazole;

5-Methoxy-3-[2-[1-(phenylmethyl)-4-piperidinyl]ethyl]-1,2-benzisoxazole;

6-Methoxy-3-[2-[1-(phenylmethyl)-4-piperidinyl]ethyl]-1,2-benzisoxazole;

7-Methoxy-3-[2-[1-(phenylmethyl)-4-piperidinyl]ethyl]-1,2-benzisoxazole;

6-Acetamido-3-[2-[1-(phenylmethyl)-4-piperidinyl]-1,2-benzisoxazole;

6-Amino-3-[2-[1-(phenylmethyl)-4-piperidinyl]ethyl]-1,2-benzisoxazole;

6-Benzamide-3-[2-[1-(phenylmethyl)-4-piperidinyl]ethyl]-1,2-benzisoxazole;

6-Benzenesulfonamide-3-[2-[1-(phenylmethyl)-4piperidinyl]ethyl]-1,2-benzisoxazole;

6-(4-Morpholinyl)-3-[2-[1-(phenylmethyl)-4piperidinyl]ethyl]-1,2-benzisoxazole;

5,7-Dihydro-3-[2-[1-(phenylmethyl)-4-piperidinyl]ethyl]-6H-pyrrolo[4,5-f]-1,2-benzisoxazol-6-one;
1-[2-[1-(Phenylmethyl)-4-piperidinyl]ethyl]isoquinoline;
3-[2-[1-(Phenylmethyl)-4-piperidinyl]ethyl]-1,2-benzisothiazole;
4-[2-[1-(Phenylmethyl)-4-piperidnyl]ethyl]-1,3-quinazoline;
6-Hydroxy-3-[2-[1-(phenylmethyl)-4-piperidyl]ethyl]-1,2-benzisoxazole;
6-Bromo-3-[2-[1-(phenylmethyl)-4-piperidyl]ethyl]-1,2-benzisoxazole;
6-Cyano-3-[2-[1-(phenylmethyl)-4-piperidyl]ethyl]-1,2-benzisoxazole;
6-Carboxamide-3-[2-[1-(phenylmethyl)-4-piperidyl]ethyl]-1,2-benzisoxazole;
3-[(1-Phenylmethyl-4-piperidyl)methoxy]-1,2-benzisoxazole;
3-[(1-Phenylmethyl-4-piperidyl)methylamino]-1,2-benzisoxazole;
3-[2-(1-Phenylmethyl)-4-piperidyl)ethylamino]-1,2-benzisoxazole;
3-[3-[1-(Phenylmethyl)-4-piperidyl]propyl]-1,2-benzisoxazole;
trans-3-[2-[1-(Phenylmethyl)-4-piperidyl]ethenyl]-1,2-benzisoxazole;
3-[2-[1-(Phenylmethyl)-4-piperazinyl]ethyl]-1,2-benzisoxazole;
5,7-Dihydro-7-methyl-3-[2-[1-(phenylmethyl)-4-piperidinyl]ethyl]-6H-pyrrolo[4,5-f]-1,2-benzisoxazol-6-one;
5,7-Dihydro-7-ethyl-3-[2[1-(phenylmethyl)-4-piperidinyl]ethyl]-6H-pyrrolo[4,5-f]-1,2-benzisoxazol-6-one;
5,7-Dihydro-3-[2-[1-(2-chloro-5-thiophenemethyl)-4-piperidinyl]ethyl]-6H-pyrrolo[4,5-f]-1,2-benzisoxazol-6-one;
5,7-Dihydro-3-[2-[1-(2-methyl-4-thiazolemethyl)-4-piperidinyl]ethyl]-6H-pyrrolo[4,5-f]-1,2-benzisoxazol-6-one;
3-[2-[1-(3-Bromophenylmethyl)-4-piperidinyl]-5,7-dihydro-6H-pyrrolo[4,5-f]-1,2-benzisoxazol-6-one;
3-[2-[1-(4-Bromophenylmethyl)-4-piperidinyl]ethyl]-5,7-dihydro-6H-pyrrolo[4,5-f]-1,2-benzisoxazol-6-one;
5,7-Dihydro-3-[3-[1-(phenylmethyl)-4-piperidinyl]propyl]-6H-pyrrolo[4,5-f]-1,2-benzisoxazol-6-one;
3-[2-[1-(Phenylmethyl)-4-piperidinyl]ethyl]-5,6,8-trihydro-7H-isoxazolo[4,5-g]quinolin-7-one;
6,8-Dihydro-3-[2-[1-(phenylmethyl)-4-piperidinyl]ethyl]-7H-pyrrolo[5,4-g]-1,2-benzisoxazol-7-one;

5,7-Dihydro-3-[2-[1-(phenylmethyl)-4-piperidinyl]ethyl]-6H-pyrrolo[5,4-f]-1,2-benzisoxazol-6-one;
3-[2-[1-(Phenylmethyl)-4-piperidinyl]ethyl]-1H-indazole;
and the pharmaceutically acceptable salts of such compounds.

Examples of other compounds of the formula I are:
6-Phenylamino-3-[2-[1-(phenylmethyl)-4-piperidinyl]ethyl]-1,2-benzisoxazole;
6-(2-Thiazolyl)-3-[2-[1-(phenylmethyl)-4-piperidinyl]ethyl]-1,2-benzisoxazole;
6-(2-Oxazolyl)-3-[2-[1-(phenylmethyl)-4-piperidinyl]ethyl]-1,2-benzisoxazole;
6-Pyrrolidinyl-3-[2-[1-(phenylmethyl)-4-piperidinyl]ethyl]-1,2-benzisoxazole;
6-Piperidinyl-3-[2-[1-(phenylmethyl)-4-piperidinyl]ethyl]-1,2-benzisoxazole;
5,7-Dihydro-5,5-dimethyl-3-[2-[1-(phenylmethyl)-4-piperidinyl]ethyl]-6H-pyrrolo[4,5-f]-1,2-benzisoxazol-6-one;
5,7-Dihydro-3-(2-[1-(phenylmethyl)-4-piperidinyl]ethyl]-7-n-propyl-6H-pyrrolo[4,5-f]-1,2-benzisoxazol-6-one;
5,7-Dihydro-3-[2-[1-(phenylmethyl)-4-piperidinyl]ethyl]-7-i-propyl-6H-pyrrolo[4,5-f]-1,2-benzisoxazol-6-one;
5,7-Dihydro-3-[2-[1-(phenylmethyl)-4-piperidinyl]ethyl]-6H-pyrrolo[4,5-f]-1,2-benzisoxazol-6-one;
3[2-[1-(Phenylmethyl)-4-piperidinyl]ethyl]-6-phenylmethylsulfone-1,2-benzisoxazole;
1-Methyl-3-[2-[1-(phenylmethyl)-4-piperidinyl]ethyl]1H-indazole; and
3-[1-Phenylmethyl-4-piperidinyl)methyl]-1,2-benzisoxazole.

The compounds of formula I may have optical centers and may therefore occur in different isomeric forms. The invention includes all stereoisomers of such compounds of formula I, including mixtures thereof.

DETAILED DESCRIPTION OF THE INVENTION

The preparation of compounds having the formula I and certain of the starting materials used in their synthesis is illustrated in the following reaction schemes. Except where otherwise stated, in the reaction schemes and discussion that follow, $R^1$, $R^2$, $R^3$, $R^4$, $R^5$, $R^6$, $R^7$, $R^8$, $R^{13}$, $R^{14}$, E, G, X, Y, M, L, a, b, l, m, n, p, and structures I, A, B, and K are defined as above.

All articles, books, patents and patent applications cited in the following discussion are incorporated herein by reference.

SCHEME 1

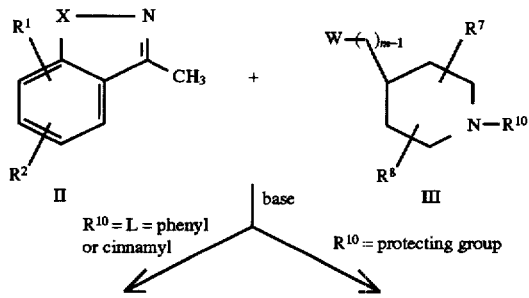

-continued
SCHEME 1
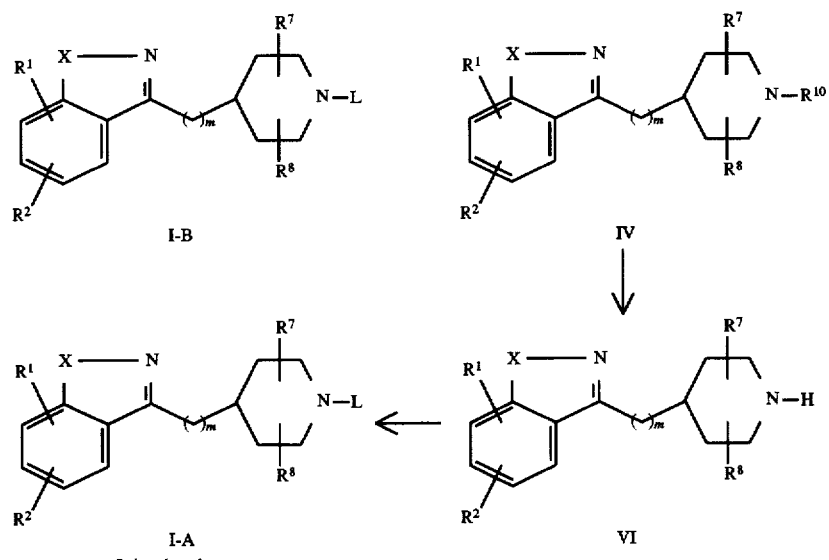
I-A
L is other than
phenyl or cinnamyl
SCHEME 2
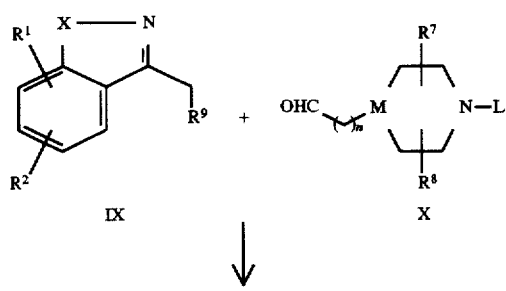
-continued
SCHEME 2
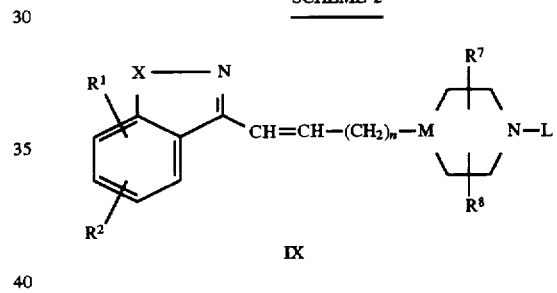

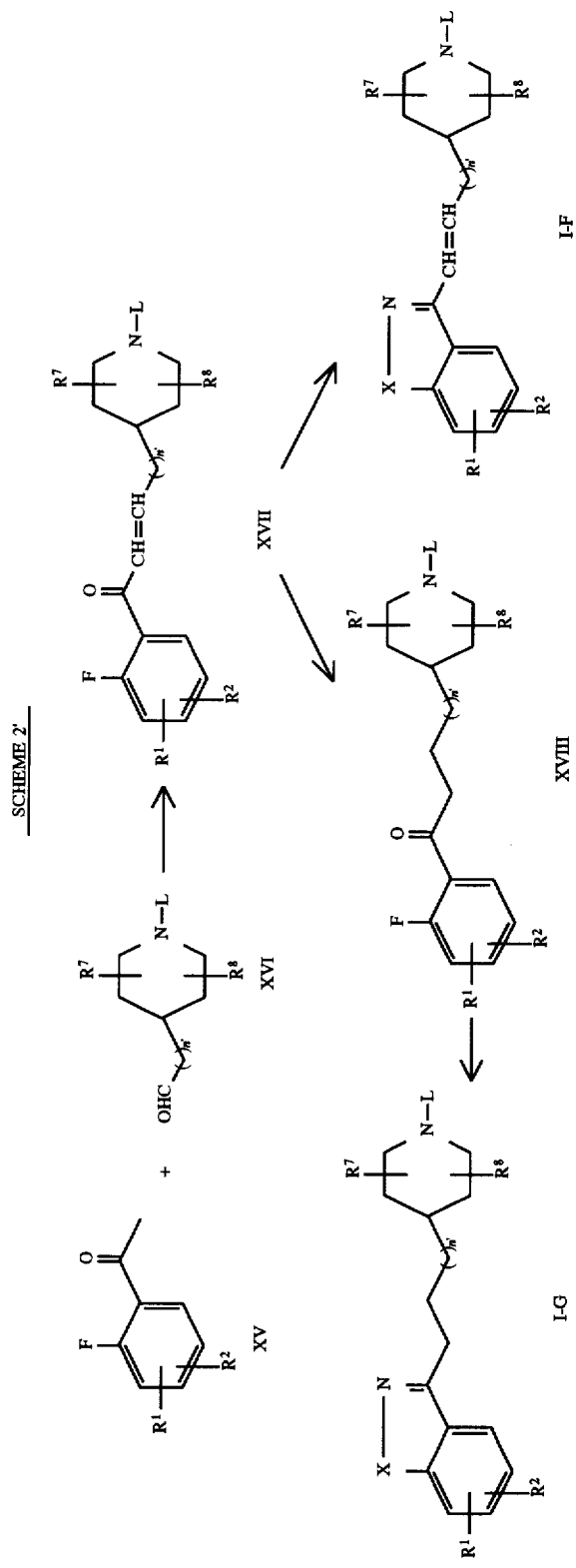

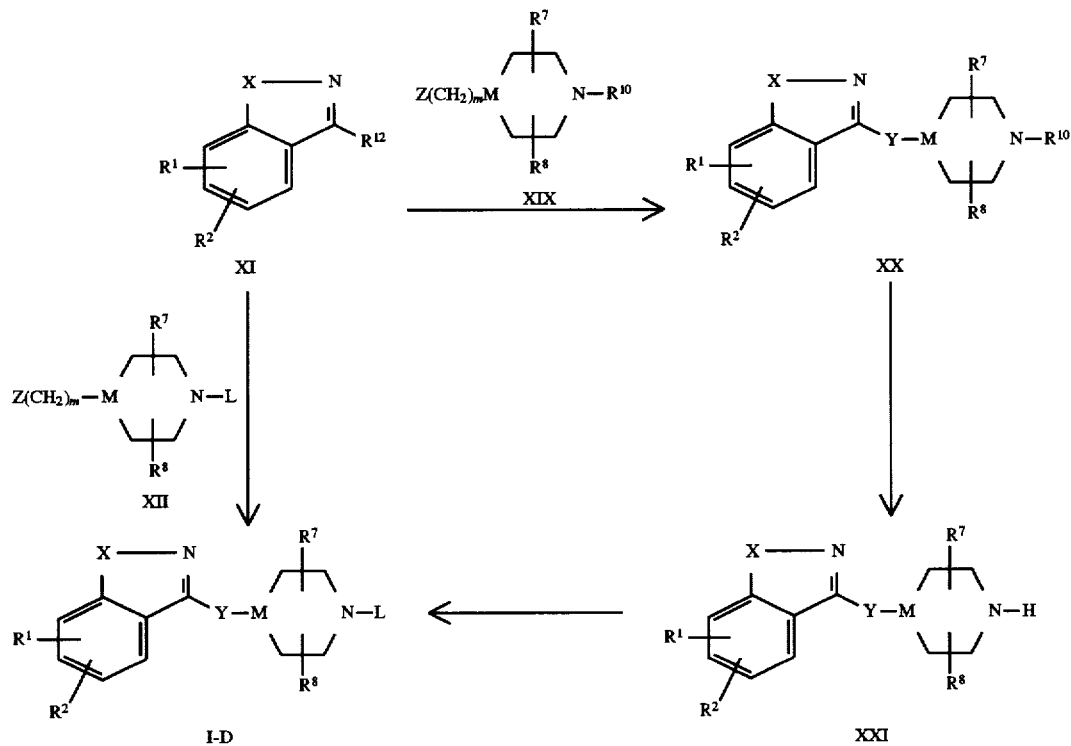
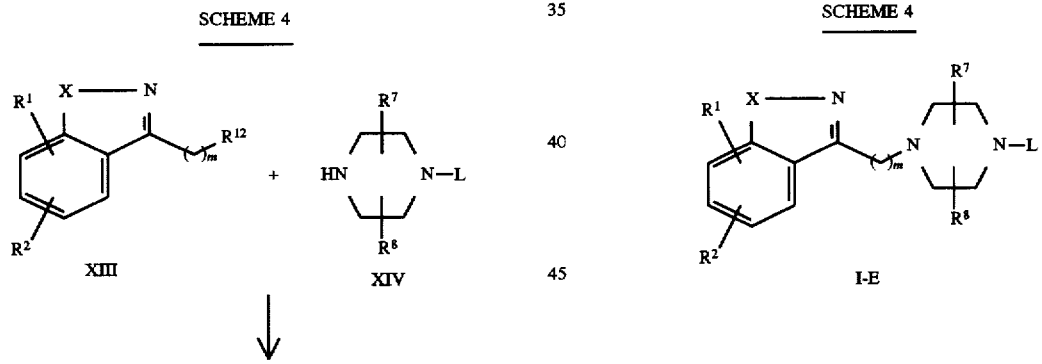

SCHEME 5
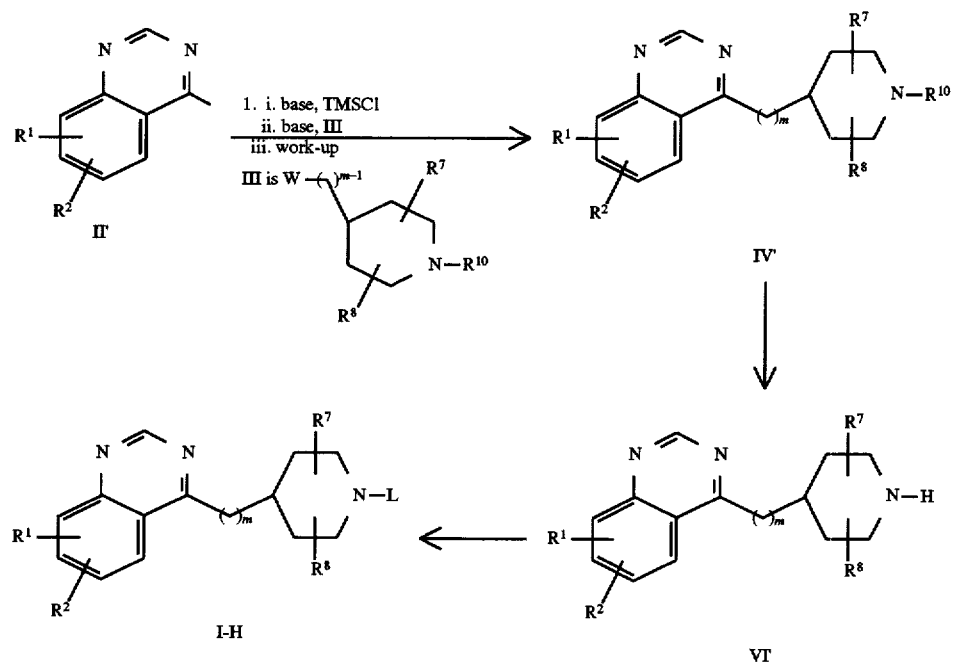
SCHEME 6
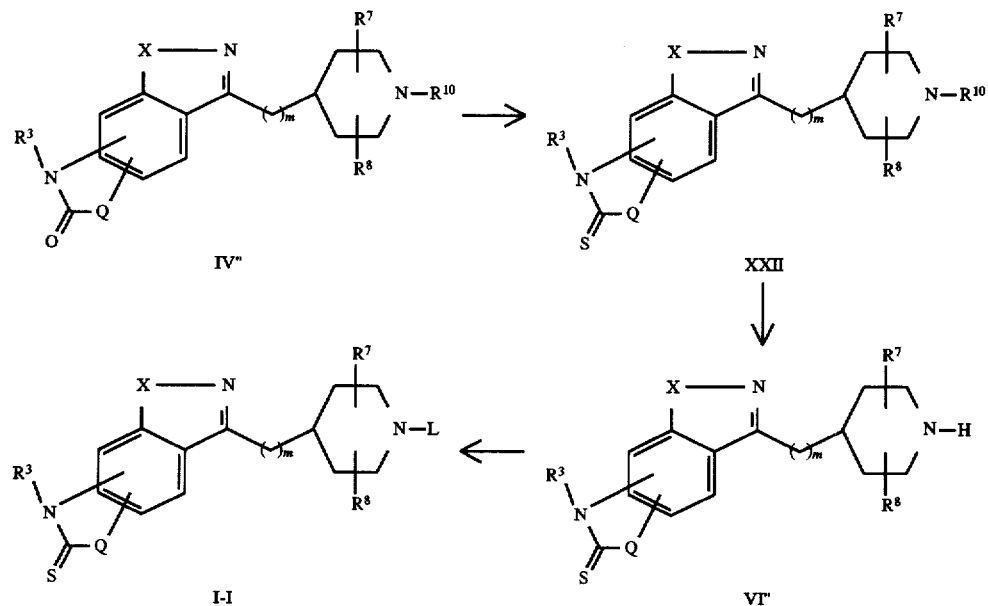

SCHEME 7

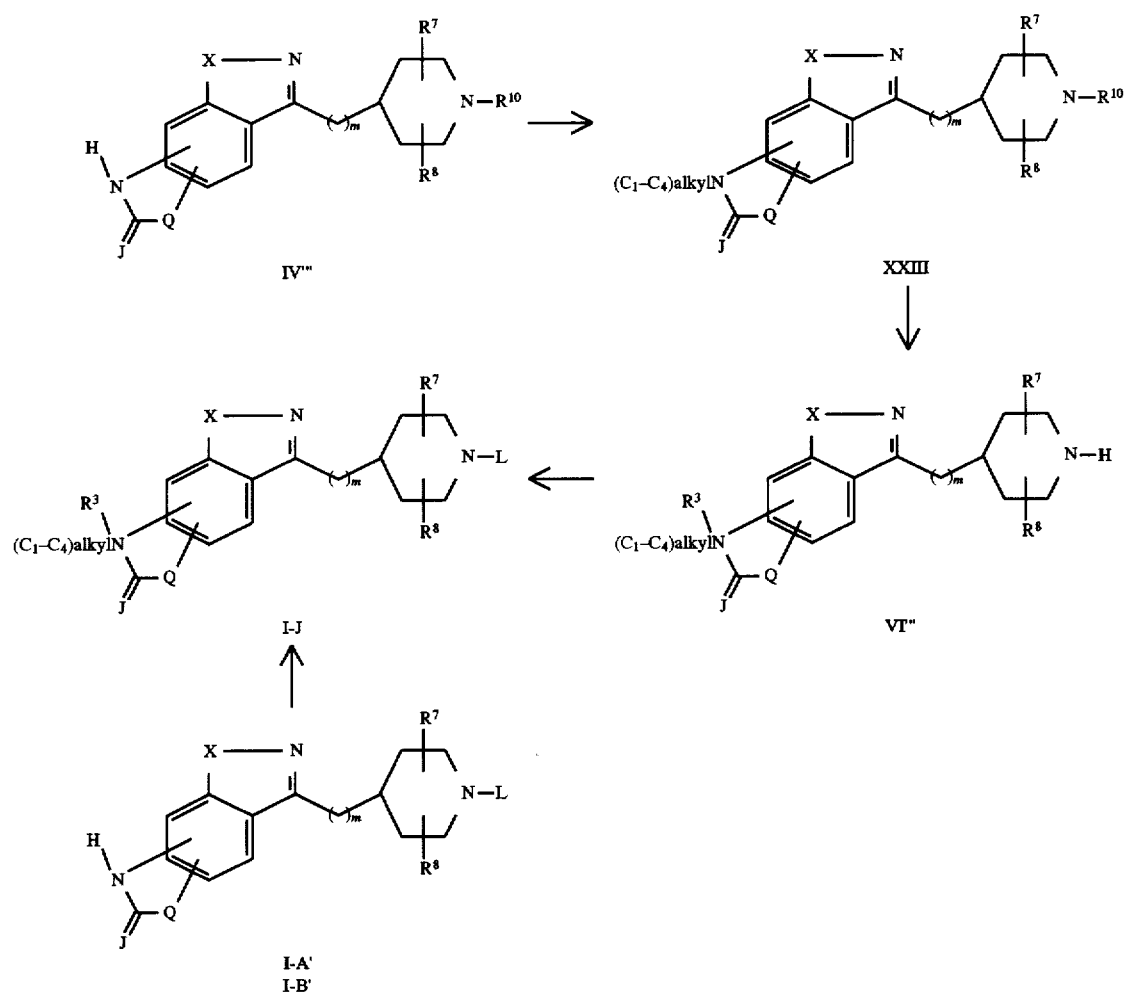

The preparation of compounds of the formula I wherein Y is —(CH$_2$)$_m$ and M is —CH— is illustrated in scheme 1. These compounds are designated in scheme 1 and hereinafter referred to as compounds of the formula I-A (those wherein L is phenyl-(C$_1$-C$_6$)alkyl, pyridylmethyl or a group of the formula K) and compounds of the formula I-B (those wherein L is phenyl or cinnamyl).

Referring to scheme 1, compounds of the formula I-A may be prepared by deprotonating a compound of the formula II with a base in the presence of, or followed by the addition of an alkylating agent of the formula III wherein R$^{10}$ is a nitrogen protecting group and W is a leaving group. When R$^{10}$ is a nitrogen protecting group, this reaction produces an intermediate of the formula IV. This intermediate is then deprotected to yield a secondary piperidine of the formula VI as a free base or a salt of the free base, after which such free base or salt is alkylated with a compound of the formula WL, wherein W is defined as above and L is phenyl-(C$_1$-C$_6$)alkyl, pyridylmethyl or a group of the formula K.

Examples of suitable leaving groups (W) are mesylate, tosylate, chloride, iodide and bromide. Examples of suitable nitrogen protecting groups (R$^{10}$) are amides such as N-formyl and N-acetyl and carbamates such as t-butoxycarbamate (BOC). The preferred nitrogen protecting group is BOC. Appropriate bases for use in the preparation of compounds of the formula IV include strong bases such as lithium diisopropylamide (LDA), n-butyllithium, s-butyllithium, and lithium (or sodium or potassium) hexamethyldisilazide (LiHMDS, NaHMDS, or KHMDS). LDA and s-butyllithium are preferred.

The reaction of a compound of formula II with a compound of formula III is generally carried out in a polar, aprotic solvent such as diethyl ether, 1,2-dimethoxyethane, or tetrahydrofuran (THF). Temperatures may range from about −78° C. to about 30° C. This reaction is preferably conducted in THF at about −78° C.

Usually, compounds of the formula II are deprotonated in the presence of a compound of formula III. However, in cases where the compound of formula II has more than one acidic proton, it is preferable to carry out the deprotonation step first followed by the immediate and rapid addition of the alkylating agent of formula III.

The protecting group (R$^{10}$) can be removed from compounds of the formula IV to form the corresponding compounds of formula VI by methods known to those skilled in the art. For example, when R$^{10}$ is BOC or another carbamate, it can be removed with an acid such as hydrogen bromide (gas or aqueous), hydrogen chloride (gas or aqueous) or trifluoroacetic acid. In the case of trifluoroacetic acid, a t-butyl cation scavenger such as thioanisole may be added. When an acid is used as the deprotecting agent, an acid addition salt of the compound of formula VI is produced rather than the free base of such compound. Appropriate solvents include non-polar solvents such as methylene chloride, as well as polar solvents such as diethyl ether, ethyl acetate, dioxane, alcohols (e.g. methanol or ethanol) and water. Temperatures may range from about −20° C. to about the reflux temperature of the solvent. It is preferable to use trifluoroacetic acid in methylene chloride with or without thioanisole at about 0° C.

Alternatively, when $R^{10}$ is BOC, it can be removed with a trialkylsilyltrifluoromethanesulfonate derivative such as trimethylsilyl-, triethylsilyl-, or t-butyldimethylsilyltrifluoromethanesulfonate in the presence of an aromatic or tertiary amine base such as 2,6-lutidine or triethylamine. Appropriate solvents for this reaction include nonpolar solvents such as methylene chloride and polar aprotic solvents such as THF, diethyl ether or DMF. Temperatures may range from about −20° C. to room temperature. It is preferable to use trimethylsilyltrifluoromethane-sulfonate and 2,6-lutidine in methylene chloride at a temperature from about 0° C. to about room temperature.

The intermediate secondary piperidine of the formula VI, obtained as the free base or salt as described above, is reacted with 2–10 equivalents of a base and then with an alkylating agent of the formula WL, wherein W is defined as above and L is phenyl-($C_1$–$C_6$)alkyl, pyridylmethyl or a group of the formula K. Suitable bases include tertiary amines such as triethylamine and diisopropylethyl-amine, aromatic amines such as pyridine and dimethylaminopyridine, and metal carbonates such as sodium bicarbonate or sodium or potassium or cesium carbonate. When W is chloride, catalytic iodide (potassium iodide or tetra-n-butylammonium iodide) may be added. Appropriate solvents include non-polar solvents such as methylene chloride and polar solvents such as dimethylformamide, THF, acetontrile, acetone, dioxane, and alcohols such as methanol or ethanol. It is preferable to carry out the alkylation in the presence of triethylamine in methylene chloride at room temperature or in the presence of sodium carbonate in dimethylformamide at room temperature.

Alternatively, the intermediate secondary piperidine of formula VI, when obtained as a salt after removal of the protecting group, can be deprotonated to the free amine by dissolving or suspending it in an appropriate solvent (e.g., methylene chloride or ethyl acetate), mixing it with aqueous sodium bicarbonate or aqueous sodium or potassium hydroxide and recovering the free amine from the organic layer by conventional extraction techniques. The free amine can then be subjected to alkylation with the appropriate alkylating agent of the formula WL under the conditions described above using 1–2 equivalents of an appropriate base.

The starting materials of formula II can be prepared according to methods known in the art. When X is oxygen, the starting 3-methyl-1,2-benzisoxazoles can be prepared by procedures similar to those described by Wunsch et al., *Adv. Heterocycl. Chem.*, 1967, 8, 277; Smalley, R. K., *Adv. Heterocycl. Chem.* 1981, 29, 2; and Thakar et al., *Indian J. Chem.* 1977, 15B, 1058. The appropriate o-hydroxy acetophenones are converted to the corresponding oximes by reaction with hydroxylamine hydrochloride in the presence of an appropriate base such as potassium or sodium hydroxide, sodium acetate or pyridine, preferably aqueous potassium hydroxide or aqueous sodium acetate, in a polar solvent such as methanol, ethanol, or water, preferably ethanol, at a temperature from about room temperature to about 120° C. The oxime is then converted to the corresponding oxime acetate by acetylation with an appropriate acylating agent such as acetic anhydride. Temperatures for this reaction may range from about room temperature to the reflux temperature of the solvent. Temperatures between 80° C. and 130° C. are preferred.

Ring closure to form the benzisoxazole ring may be carried out by heating the neat oxime acetate at a temperature from about 125° C. to about 200° C. under atmospheric pressure or reduced pressure (e.g., from about 0.01 mm Hg ($1.33 \times 10^{-5}$ bars) to about 760 mm Hg (1.01 bars)). Ring closure is preferably accomplished by heating the oxime acetate at reflux in an appropriate base such as pyridine, or by heating the oxime acetate at a temperature of about 130° C. in a polar solvent such as DMF or DMSO (dimethylsulfoxide) in the presence of several equivalents of an appropriate base such as pyridine or 2,6-lutidine.

Alternatively, ring closure can be carried out directly from the oxime by reaction with an acyl or sulfonyl chloride such as oxalyl or thionyl chloride in the presence of an aromatic amine such as pyridine (See Kalkote et al., *Aust. J. Chem.* 1977, 30, 1847). Suitable solvents include polar solvents such as diethyl ether or THF. Temperatures can range from about 0° C. to about room temperature. Another method of closure involves treatment of the oxime with one or less equivalents of a base such as potassium hydroxide in a polar solvent such as methanol at temperatures ranging from about room temperature to about 100° C. (Crabbe et al., *J. Chem. Soc. Perkin Trans. 1*, 1973, 2220).

When X is sulfur, the starting 3-methyl-1,2-benzisothiazoles can be prepared from o-methylthio acetophenones following procedures similar to those described above for the benzisoxazoles (See McKinnon et al., *Can. J. Chem.*, 1988, 66, 1405 and references cited therein). The o-methylthio acetophenones are converted into the corresponding oximes and ring closure is carried out directly by reaction with an appropriate acylating agent such as acetic anhydride in a base such as pyridine. The reaction temperature may range from about room temperature to about 130° C., and is preferably about 120° C.

When X is $NR^4$ wherein $R^4$ is hydrogen the starting 3-methyl-1H-indazoles can be prepared according to methods described by Behr et al., "Pyrazoles, Pyrazolines, Pyrazolidines, Indazoles, and Condensed Rings," Heterocyclic Compounds, R. H. Wiley, Ed., 1967, 289; Bartsch et al., *J. Heterocycl. Chem.*, 1984, 21, 1063; Hannig et al., *Pharmazie* 1976, 31, 534; Barton et al., *J. Chem. Soc. Chem. Comm.*, 1982, 450; Ruechardt et al., *Liebigs Ann. Chem.*, 1980, 908; and Rees et al., *J. Chem. Soc. D*, 1971, 827. N-Alkylation of 3-methyl-1H-indazoles (X is $NR^4$ wherein $R^4$ is ($C_1$–$C_4$)alkyl) can be carried out as described by Behr et al., "Pyrazoles, Pyrazolines, Pyrazolidines, Indazoles, and Condensed Rings," Heterocyclic Compounds, R. H. Wiley, Ed., 1967, 309; Palmer et al., *J. Chem. Soc., Perkin Trans. II*, 1975, 1695; and Claramunt et al., *Heterocycles* 1985, 23, 2895.

When X is —CH═CH—, the starting 1-methylisoquinolines can be prepared according to the Bischler-Napieralksi or Pictet-Spengler methods (See Organic Reactions, Vol. VI, chapters 2 and 3, pp. 74–190, John Wiley and Sons, New York, 1951).

When X is —N═CH—, the starting 4-methylquinazolines can be prepared according to methods described by Byford et al., *Indian J. Chem.*, 1988, 27B, 396; Higashino, T., *Chem. Pharm. Bull.*, 1962, 10, 1043; and Uff et al., *J.*

*Chem. Soc., Perkin Trans. 1,* 1986, 2295.

When X is —CH=N— the starting 1-methylphthalazines can be prepared according to methods described by Kant et al., *J. Heterocycl. Chem.,* 1985, 22, 1065 and references cited therein; Acheson et al., *J. Chem. Soc. C,* 1966, 2218; and Gabriel et al., *Chem. Ber.* 1897, 30, 3022.

When X is —N=N—, the starting 4-methyl-1,2,3-benzotriazines can be prepared according to methods described by Adger et al., *J. Chem. Soc., Perkin Trans. 1,* 1975, 31; Boulton et al., *Ibid.,* 1988, 1509; and Rees et al., *J. Chem. Soc. D,* 1971, 828.

When one or both of $R^1$ and $R^2$ are $NH_2$, the starting material of formula II may be prepared from the corresponding NHAc precursor (Ac=acetyl) by acid hydrolysis. The acid hydrolysis can be carried out with aqueous hydrochoric acid at temperatures ranging from about 50° C. to about 120° C. Heating to reflux (about 120° C.) in 1N HCl is preferred. The corresponding NHBz (Bz=benzoyl) or $NHSO_2C_6H_5$ compounds can be prepared from the corresponding amino derivative by reaction with the appropriate benzoyl or benzenesulfonyl chloride in the presence of a base such as triethylamine, pyridine, or dimethylaminopyridine. Suitable solvents include methylene chloride, THF, diethylether, or dimethylformamide. Temperatures may range from about −20° to about 80° C. When one or both of $R^1$ and $R^2$ is NHBz, it is preferable to use triethylamine/dimethylaminopyridine in methylene chloride at room temperature. When one or both of $R^1$ and $R^2$ is $NHSO_2Ph$, it is preferable to use pyridine in methylene chloride at 0° C.

Cyclic dialkylamino compounds of the formula II (i.e., those wherein one or both of $R^1$ and $R^2$ are $NR^5R^6$ wherein $NR^5R^6$ together form a ring) can also be prepared from the corresponding amino derivative by alkylation with the appropriate bis-halide reagent of the formula

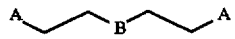

wherein each A is independently bromide or chloride and B is oxygen or $(CH_2)_q$ wherein q is 0 to 2, in the presence of an appropriate base such as triethylamine or diisopropylethylamine (Hunig's base), in an appropriate nonpolar solvent such as toluene or xylene. The alkylation is typically carried out at a temperature from about room temperature to about 150° C. It is preferably conducted in the presence of Hunig's base in toluene at about 120° C. (reflux). (See Verboom et al., *J. Org. Chem.* 1984, 49, 269).

Alternatively, these cyclic dialkylamino derivatives may be prepared by nucleophillic displacement of an aromatic fluoride with the appropriate cyclic amine. Suitable solvents for this reaction include polar aprotic solvents such as dimethylsulfoxide (DMSO), dimethylformamide (DMF), acetonitrile, pyridine and hexamethylphosphoramide. Acetonitrile and pyridine are preferred. The reaction may be run in the presence of a base such as a tertiary or aromatic amines (e.g., triethylamine, diisopropylethylamine, pyridine or dimethylaminopyridine), preferably pyridine or triethylamine. The reaction temperature may range from about room temperature to about 160° C., and is preferably from about 80° C. to about 160° C.

When $R^1$ and $R^2$, together with the carbons to which they are attached, form a group of the formula

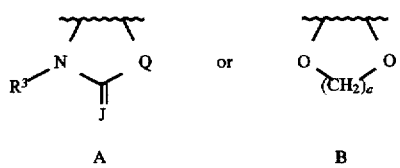

and X is oxygen or sulfur, the starting material of formula II may be prepared by the following procedure which is illustrated only for cases wherein $R^1$ and $R^2$ form a group of formula A.

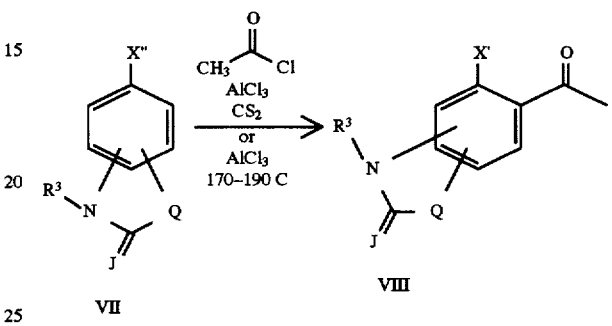

First, a compound of the formula VIII wherein X' is hydroxy, thiol or methyl sulfide is prepared by Friedel-Crafts acylation of the corresponding compound of the formula VII, wherein X" is methoxy or methyl sulfide with an acylating agent such as acetyl chloride or acetic anhydride, preferably acetyl chloride, in the presence of a Lewis acid such as aluminum chloride, titanium tetrachloride or boron triflouride etherate, preferably aluminum chloride. Appropriate solvents include carbon disulfide, 1,2-dichloroethane and nitrobenzene. Carbon disulfide and 1,2-dichloroethane are preferred. Generally, this reaction is conducted at a temperature from about room temperature to about 200° C., preferably from about 50° C. to about 100° C.

Alternatively, a compound of formula VIII wherein X' is hydroxy, may also be obtained by Fries rearrangement of the corresponding compound of the formula VII wherein X" is acetyloxy. A mixture of VII and a Lewis acid such as aluminum chloride, boron trifluoride etherate or titanium tetrachloride is heated at temperatures from about 80° C. to 200° C. either neat or in the presence of a solvent such as nitrobenzene, or 1,2-dichloroethane. The Fries rearrangment is preferably conducted neat with aluminum chloride at 170°–190° C.

The compounds of formula VIII obtained by the foregoing process may be converted to the corresponding starting materials of formula II by the procedure described above for 1,2-benzisoxazoles and 1,2-benzisothiazoles.

Referring to scheme 1, compounds of the formula III may be prepared from the corresponding compounds wherein W is hydroxy by methods known in the art. For example, compounds of the formula III wherein W is iodide can be prepared by reacting the hydroxy counterpart with iodine and triphenylphosphine in the presence of a base such as pyridine or imidazole in a non-polar solvent such as benzene or toluene at a temperature from about room temperature to about 130° C. Preferably, the reaction is carried out in benzene in the presence of pyridine at about 90° C. (reflux).

Compounds of the formula I-B may be prepared by deprotonating a compound of the formula II with a base in the presence of, or followed by the addition of, an alkylating agent of the formula III wherein $R^{10}$ is phenyl or cinnamyl and W is defined as above. Suitable and preferred bases, solvents and conditions are similar to those described above for the preparation of compounds of the formula IV.

Scheme 2 illustrates the preparation of compounds of the formula I wherein Y is —CH=CH(CH$_2$)$_n$— via an aldol-type condensation. These compounds are designated in scheme 2 and hereinafter referred to as compounds of the formula I-C. Referring to scheme 2, a compound of the formula IX wherein R$^9$ is hydrogen is deprotonated with a base followed by immediate and rapid addition of an aldehyde of the formula X. Suitable bases and solvents are the same as those described above for the first reaction in scheme 1. The reaction temperature may range from about −78° C. to about room temperature. The reaction is preferably carried out using lithium diisopropylamide in THF at about −78° C. and allowed to warm to room temperature.

If an intermediate alcohol is formed, it can be dehydrated to the olefin under standard acidic conditions, using an acid such as dilute hydrochloric acid, p-toluenesulfonic acid or pyridinium p-toluenesulfonate, preferably p-toluenesulfonic acid, in a solvent such as benzene, toluene, THF or methylene chloride, at a temperature from about 0° C. to about 130° C. Preferably, the dehydration is carried out in benzene at about 80° C. (reflux) with azeotropic removal of water. Dehydration may also be accomplished by treatment with Burgess' reagent

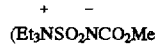

(Et$_3$NSO$_2$NCO$_2$Me in methylene chloride or benzene at a temperature from about room temperature to about 80° C.

Alternatively, the intermediate alcohol may be converted into a good leaving group such as mesylate or tosylate and then eliminated with an appropriate base. The mesylate or tosylate can be prepared under standard conditions by reacting the alcohol with methanesulfonyl chloride or p-toluenesulfonyl chloride in the presence of a base such as triethylamine, diisopropylethylamine, or pyridine. Appropriate solvents include methylene chloride and THF, with methylene chloride being preferred.

Temperatures may range from about 0° C. to about 60° C., and are preferably from about 0° C. to about room temperature. Elimination to form the olefin can then be carried out with a base such as diazabicycloundecane or diazabicyclononane in a suitable solvent such as benzene, methylene chloride, or THF, with benzene or methylene chloride being preferred, at a temperature from about 0° C. to about 100° C., preferably from about room temperature to about 100° C.

Compounds of the formula I-C may also be prepared by a Wittig reaction from compounds of the formula IX wherein R$^9$ is bromine, chlorine or iodine. According to this procedure, a compound of formula IX is converted into its phosphonium salt by treatment with triphenylphosphine in a nonpolar solvent such as benzene, toluene or xylene, preferably toluene, at a temperature from about room temperature to about 150°, preferably from about 80° C. to about 120° C. The phosphonium salt may then be deprotonated with a strong base such as sodium hydride, potassium t-butoxide, potassium hydride or n-butyllithium in a suitable solvent such as diethylether or THF, at a temperature from about 0° C. to about 80° C. The deprotonation is preferably carried out with sodium hydride in THF at about room temperature.

Scheme 2' illustrates an alternative preparation of compounds of the formula I wherein X is oxygen or NR$^4$, Y is (CH$_2$)$_m$ or —CH=CH(CH$_2$)$_n$ and M is carbon (i.e. —CH—). These compounds are designated in Scheme 2', and hereinafter referred to as compounds of the formula I-F (those where Y is —CH=CH(CH$_2$)$_n$, and n' is an integer from 0 to 3) and I-G (those where Y is (CH$_2$)$_m$ and n' is an integer from 0 to 1). Referring to Scheme 2', compounds of the formula I-F may be prepared by deprotonating a compound of the formula XV with a suitable base followed by addition of an aldehyde of formula XVI to give an intermediate of formula XVII. This intermediate is then transformed to compounds of the formula I-F by reaction with an appropriate amine.

Appropriate bases for use in the preparation of compounds of the formula XVII include lithium diisopropylamide, lithium or sodium or potassium hexamethyldisilazide, or n-butyllithium, preferably lithium diisopropylamide or lithium hexamethydisilazide. The reaction of a compound of formula XV with a compound of formula XVI is generally carried out in a polar aprotic solvent such as diethyl ether, 1,2-dimethoxyethane, or tetrahydrofuran. Temperatures may range from −78° C. to 80° C. This reaction is preferably conducted in THF at −78° C. and allowed to warm to room temperature.

A compound of formula I-F is then obtained from an intermediate of formula XVII by reaction with an amine such as hydrazine or hydroxylamine in the presence of a base such as sodium or potassium hydroxide, sodium or potassium carbonate, or sodium or potassium alkoxide (methoxide or ethoxide), preferably sodium or potassium hydroxide. In some cases (when amine is hydrazine), addition of a base may not be necessary. Suitable solvents for this reaction include methanol, ethanol, i-propanol, water, or, when amine is hydrazine, hydrazine itself may be used as a solvent. Temperatures may range from 50° C. to 120° C. It is preferable to react XVII with hydrazine at 120° C. (reflux), or with hydroxylamine and potassium hydroxide in EtOH/water at 100° C. (reflux). Upon reaction with hydroxylamine, the intermediate oxime obtained may be isolated and then cylclized to compounds of the formula I-F following the suitable and preferred conditions described above for the preparation of starting materials 3-methyl-1, 2-benzioxazoles.

Compounds of the formula I-G may be prepared by reducing an intermediate of formula XVII to give a compound of formula XVIII. The intermediate of formula XVII may then be reacted with an amine to give compounds of the formula I-G. An intermediate of formula XVII is reduced with hydrogen gas to an intermediate of formula XVIII in the presence of a catalyst such as palladium on carbon, platinum oxide, or rhodium on carbon, preferably platinum oxide in a polar solvents such as ethyl acetate, tetrahydrofuran, ethanol, or acetic acid, preferably EtOH. Pressure may range from atmospheric to 50 psi (3.45 bars), preferably 40–50 psi (2.76–3.45 bars) and temperature may range from room temperature to 80° C., preferably room temperature.

A compound of formula I-G is then obtained from an intermediate of formula XVIII following the suitable and preferred conditions described above for the preparation a compound of formula I-F from an intermediate of formula XVII.

Scheme 3 illustrates the preparation of compounds of the formula I wherein Y is —O(CH$_2$)$_m$— or —NR$^4$(CH$_2$)$_m$. These compounds are designated in scheme 3 and hereinafter referred to as compounds of the formula I-D. Referring to scheme 3, compounds of the formula I-D may be prepared by reacting a compound of the formula XI wherein R$^{12}$ is chloro or bromo, with a nucleophile of the formula XII, wherein Z is —NHR$^4$ or —OH. When Y is NR$^4$(CH$_2$)$_m$ (i.e., Z is —NHR⁴), the amine of formula XII is generally reacted with the appropriate compound of formula XI either neat or in a polar solvent such as dimethylformamide (DMF), dimethylsulfoxide (DMSO), THF or pyridine. DMSO and DMF are preferred solvents. An acid acceptor such as diazabicycloundecane, pyridine, lutidine, triethylamine or metal carbonates such as potassium or sodium or cesium carbonate may be added. Metal carbonates such as potassium carbonate are preferred. The reaction temperature may range from about room temperature to about 160° C. and is preferably from about 100° C. to about 160° C.

When Y is $O(CH_2)_m$ (i.e., Z is —OH), the alkoxide anion is formed and this species is reacted with the compound of formula XI. According to this procedure, the alcohol (XII) is deprotonated with a suitable base, after which the appropriate compound of formula XI is added and the mixture is heated. Examples of suitable bases are sodium, sodium hydride and potassium hydride with sodium hydride being preferred. Suitable solvents include THF, DMF and DMSO, with THF and DMF being preferred. This reaction is generally conducted at a temperature from about 40° C. to about 160° C. Temperatures between about 60° C. and about 160° C. are preferred.

Alternatively, compounds of the formula I-D may be prepared by reacting a compound of formula XI with a nucleophile of the formula XIX wherein Z and $R^{10}$ are defined as above. This reaction produces an intermediate of formula XX which is then deprotected to yield a secondary piperidine of formula XXI as a free base or a salt of the free base, after which such free base or salt is alkylated with a compound of the formula WL, wherein W is defined as above and L is phenyl($C_1$–$C_6$)alkyl, pyridylmethyl, or a group of the formula K.

Suitable and preferred bases, solvents, and conditions for the reaction of a compound of formula XI with a nucleophile of the formula XIX are similar to those described for the reaction of a compound of the formula XI with a nucleophile of the formula XII for the preparation of compounds of the formula I-D. Suitable and preferred bases, solvents, and conditions for the transformations of compounds of the formulas XX and XXI to prepare compounds of the formula I-D are similar to those described in scheme 1 for compounds of the formulas IV and VI to prepare compounds of the formula I-A.

Scheme 4 illustrates the preparation of compounds of the formula I wherein Y is —($CH_2$)$_m$— and M is nitrogen. These compounds are designated in scheme 4 and hereinafter referred to as compounds of the formula I-E. Referring to scheme 4, a compound of the formula XIII wherein $R^{12}$ is chloro, bromo or iodo is reacted with a compound of the formula XIV. This reaction may be carried out in the presence of an acid acceptor such as pyridine, 2,6-lutidine or a metal carbonate (e.g., sodium bicarbonate or sodium or potassium carbonate). When $R^{12}$ is chloro or bromo, a catalytic amount of a displacement promoter may be added. Examples of suitable displacement promoters are sodium iodide, potassium iodide or tetra-n-butylammonium iodide. Generally, this reaction is conducted in a nonpolar solvent such as toluene or xylene, or in a polar solvent such as THF, DMF or DMSO, preferably xylene or DMF, at a temperature from about room temperature to about 160° C., preferably from about 90° C. to about 160° C.

Scheme 5 illustrates the preparation of compounds of the formula I wherein X is —N=CH— and M is carbon (i.e. —CH). These compounds are designated in scheme 5 and hereinafter referred to as compounds of the formula I-H. Referring to scheme 5, a compound of the formula II' may be deprotonated with one equivalent of a base followed by addition of a silylating agent (trimethylsilyl chloride). Sequential deprotonation with a second equivalent of the same base followed by addition of an alkylating agent of the formula III and appropriate work-up produces an intermediate of the formula IV'. This intermediate is then deprotected as described in scheme I to yield a secondary piperidine of formula VI' as a free base or a salt of the free base, after which such free base or salt is alkylated with a compound of the formula WL, wherein W is defined as above and L is phenyl($C_1$–$C_6$)alkyl, pyridylmethyl, or a group of the formula K.

Suitable bases, solvents, and temperatures for deprotonation of a compound of the formula II' are the same as those described above for the first reaction in scheme I, preferably LDA in THF at 0° to room temperature. After addition of the first equivalent of base, a silylating agent such as trimethylsilyl or triethylsilyl chloride is added, preferably trimethylsilyl chloride. A second equivalent of the same base is then added followed by an alkylating agent of the formula III. The trimethylsilyl group is then removed under acidic conditions by stirring the crude reaction mixture with dilute hydrochloric acid for 30–60 min at room temperature. Then, the crude reaction mixture is made basic with aqueous sodium carbonate, or aqueous sodium or potassium hydroxide, preferably aqueous sodium hydroxide, and the intermediate of formula IV' is extracted with an organic solvent by conventional extraction techniques. Suitable and preferred conditions for the transformation of intermediates of the formula IV' to compounds of the formula I-H are the same described in scheme I for the preparation of compounds of the formula I-A.

Scheme 6 illustrates the preparation of compounds of the formula I wherein Y is ($CH_2$)$_m$, M is carbon (i.e. —CH—), J is sulfur and Q is CHCH₃, C(CH₃)₂, —CH=CH, or ($CH_2$)$_1$. These compounds are designated in scheme 6 and hereinafter referred to as compounds of the formula I-I. Referring to scheme 6, a compound of the formula I-I may be prepared from the corresponding compound of the formula IV" where J is oxygen by reacting with a phosphorus sulfide to give an intermediate of the formula XXII. This intermediate is then deprotected as described in scheme I to yield a secondary piperidine of formula VI" as a free base or a salt of the free base, after which such free base or salt is alkylated with a compound of the formula WL, wherein W is defined as above and L is phenyl($C_1$–$C_6$)alkyl, pyridylmethy, or a group of the formula K.

The transformation of a compound of formula IV" to an intermediate of formula XXII is carried out with a phosphorous sulfide such as phosphorous pentasulfide ($P_2S_{10}$) or Lawesson's reagent [2,4-bis(4-methoxyphenyl)-1,3-dithia-2,4-diphosphetane-2,4-disulfide] in an non-polar solvent such as benzene, toluene, or xylene. Temperatures may range from 50° C. to 160° C. Lawesson's reagent in toluene at 80° C. is preferred. Suitable and preferred conditions for the transformation of intermediates of the formula XXII to compounds of the formula I-I are the same ones described in scheme 1 for the preparation of compounds of the formula I-A.

Scheme 7 illustrates the preparation of compounds of the formula I wherein Y is ($CH_2$)m, M is carbon (i.e. —CH—), and $R^3$ is ($C_1$–$C_6$) alkyl. These compounds are designated in scheme 7 and hereinafter referred to as compounds of the formula I-J. Referring to scheme 7, a compound of the formula I-J may be prepared from the corresponding compounds of the formula IV'" where $R^3$ is hydrogen by deprotonating with a base followed by addition of the appropriate alkylating agent (preferably the appropriate ($C_1$–$C_6$) alkyl chloride, bromide, or iodide) to give an intermediate of formula XXIII. This intermediate is then deprotected as described in scheme 1 to yield a secondary piperidine of formula VI''' as a free base or a salt of the free base, after which such base or salt is alkylated with a compound of the formula WL, wherein W is defined as above and L is phenyl($C_1$–$C_6$)alkyl, pyridylmethyl, or a group of the formula K.

Suitable bases for the transformation of a compound of the formula IV''' to a compound of the formula XXIII include sodium hydride, potassium hydride, lithium diisopropylamide, or n-butyllithium, preferably sodium hydride. The reaction is generally carried out in a polar aprotic solvent such as tetrahydrofuran, dimethylformamide, or 1,2-dimethoxyethane and temperatures may range from –78° C. to 80° C. The reaction is preferably conducted in dimethylformamide at room temperature. Suitable and preferred conditions for the transformation of intermediates of the formula XXIII to compounds of the formula I-J are the same described in scheme 1 for the preparation of compounds of the formula I-A.

Alternatively, a compound of the formula I-J may be prepared directly from the corresponding compound of the formula I-A' wherein L is phenyl-($C_1$–$C_6$) alkyl, pyridylmethyl or a group of the formula K and $R^3$ is hydrogen or I-B' wherein L is phenyl or cinnamyl and $R^3$ is hydrogen. Compounds of the formula I-A' and I-B' are prepared according to the methods described in scheme 1 for the preparation of compounds I-A and I-B. Suitable and preferred bases, solvents, and conditions for the transformation of compounds of the formula I-A' and I-B' to compounds of the formula I-J are the same described above for the preparation of compounds of the formula XXIII.

When one or both of $R^1$ and $R^2$ are OH, compounds of the formula I may be prepared from the corresponding —OMe precursor by dealkylation with a Lewis acid such as aluminum trichloride, boron trichloride, boron tribromide, or a protic acid such as aqueous hydrochloric or hydrobromic acid. Suitable solvents for the reaction with Lewis acids include non-polar solvents such as benzene, toluene, dichloromethane, or 1,2-dichlorethane. Temperatures may range from –78° C. to 120° C. Aqueous hydrobromic acid (48%) at 100°–120° C. (reflux) is preferred.

When one or both of $R^1$ and $R^2$ are $NH_2$, compounds of the formula I may be prepared from the corresponding NHAc precursor (Ac=acetyl) by acid hydrolysis under the suitable and preferred conditions described above for the formation of starting materials of formula II wherein one or both of $R^1$ and $R^2$ are $NH_2$. The corresponding nitrile (—CN) compounds can be prepared from the corresponding amino compounds via a diazonium salt formation by reacting the amino compound with nitrous acid (made from aqueous hydrochloric acid and sodium nitrite) followed by neutralization and addition to CUCN. Suitable solvents include polar protic solvents such as water or biphasic mixtures with non-polar solvents such as benzene, toluene, or xylene. Neutralization may be carried out by adding a base such as sodium carbonate, potassium carbonate, sodium hydroxide, or potassium hydroxide until pH 7. Temperatures may range from –20° C. to 60° C. It is preferable to carry out the diazonium salt formation in water at 0° C., to neutralize with sodium carbonate, and to add the diazonium salt to a biphasic mixture of aqueous CuCN and toluene at 0° C., followed by heating to 50° C.

When one or both of $R^1$ and $R^2$ are carboxamide (—$CONH_2$), compounds of the formula I may be prepared from the corresponding nitrile (—CN) precursor by reaction with a base such as sodium hydroxide, potassium hydroxide or tetramethylammonium hydroxide in a polar solvent such as water, methanol, ethanol, or t-butanol. Temperatures may range from room temperature to 120° C. Potassium hydroxide in t-butanol at 85°–100° C. is preferred.

Compounds of the formula I other than those of formulae I-A–I-J may be prepared by methods that will be obvious to those skilled in the art from the procedures described above and other known methods.

In each of the above reactions, pressure is not critical. Pressures in the range of about 0.5–3 atm (0.5–3 bars) are suitable, and ambient pressure (generally, about one atmosphere) is preferred as a matter of convenience. Also, for those reactions where the preferred temperature varies with the particular compounds reacted, no preferred temperature is stated. For such reactions, preferred temperatures for particular reactants may be determined by monitoring the reaction using thin layer chromatography.

The compounds of formula I and their pharmaceutically acceptable salts (hereinafter referred to as the "active compounds of the invention") may be administered to a patient by various methods, for example, orally as capsules or tablets, parentally as a sterile solution or suspension, and in some cases, intravenously in the form of a solution. The free base compounds of the invention may be formulated and administered in the form of their pharmaceutically acceptable acid addition salts.

The daily dose of the active compounds of the invention is generally in the range of from about 0.005 to about 300 mg/day, optionally from about 1 to 300 mg/day, and preferably from about 0.01 to about 1 mg/day for the average adult human, and may be administered in single or divided doses.

When incorporated for parenteral administration into a solution or suspension, the active compounds of the invention are present in a concentration of at least 1 weight percent, and preferably between about 4 to 70 weight percent (based on the total weight of the unit). The parenteral dosage unit typically contains between about 5 to 100 mg of active compound(s).

The active compounds of the invention may be administered orally with an inert diluent or an edible carrier, or they may be enclosed in gelatin capsules or compressed into tablets. Such preparations should contain at least 0.5% of active compound(s), but the concentration may vary depending upon the particular form and may be from 4 to 70 weight percent (based on the total weight of the unit). The oral dosage unit typically contains between 1.0 mg to 300 mg of active compound.

The cholinesterase inhibiting activity of the active compounds of the invention may be determined by a number of standard biological or pharmacological tests. One such procedure for determining cholinesterase inhibition is described by Ellman et al. in "A New and Rapid Colorimetric Determination of Acetylcholinesterase Activity", Biochem. Pharm. 1, 88, (1961).

The present invention is illustrated by the following examples. It will be understood, however, that the invention is not limited to the specific details of these examples. Melting points are uncorrected. Proton nuclear magnetic resonance spectra ($^1$H NMR) and $C^{13}$ nuclear magnetic resonance spectra ($C^{13}$ NMR) were measured for solutions in deuterochloroform ($CDCl_3$) except where otherwise noted and peak positions are expressed in parts per million (ppm). The peak shapes are denoted as follows: s, singlet; d, doublet; t, triplet; q, quartet; m, multiplet; br, broad. Frequencies (J) are expressed in Hertz. 1M solutions of lithium diisopropylamide were freshly prepared by adding n-butyllithium (1.6–2.5M in hexanes) to a solution of diisoproylamine in tetrahydrofuran at 0°.

EXAMPLE 1

3-[2-[1-(Phenylmethyl)-4-piperidinyl]ethyl]-1,2-benzisoxazole maleate

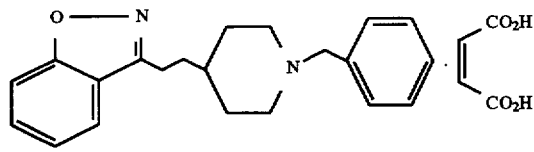

a) 1,4-Piperidinedicarboxylic acid, 1-(1,1-dimethylethyl) ester, 4-ethyl ester

A solution of ethyl isonipecotate (20.0 g, 0.127 mol) and triethylamine (17.8 mL, 0.127 mol) in 1:1 dioxane-$H_2O$ (1.2 L) was cooled to 0° C. After 15 min, t-BOC-anhydride (35.2 g, 0.161 mol) was added and the resulting mixture was allowed to warm to room temperature overnight. The mixture was extracted with ethyl acetate (4 times) and the combined organic layer was washed with 1N hydrochloric acid, water and brine, and then dried (magnesium sulfate), filtered, and concentrated to give a light orange oil. A Kugelrohr distillation (0.05 torr (6.67 bars), 80°–90° C.) gave the title carbamate (30.69 g, 94%) as a colorless oil.

$^1$H-NMR (CDCl$_3$) δ 4.11 (q, 2H, J=7.2 Hz), 3.97–4.05 (m, 2H), 2.80 (br t, 2H, J-11.6 Hz), 2.40 (tt, 1H, J=11.0 Hz, J=3.9 Hz), 1.81–1.86 (m, 2H), 1.52–1.66 (m, 2H), 1.43 (s, 9H), 1.23 (t, 3H, J=7.2 Hz).

b) 4-Hydroxymethyl-1-piperidinecarboxylic acid, 1-(1,1-dimethylethyl)ester

Lithium aluminum hydride (4.3 g, 0.114 mol) was added to a cold solution (0° C.) of the carbamate formed in step a (26.57 g, 0.103 mol) in tetrahydrofuran (THF) (1 L). After 30 min, the ice bath was removed and the reaction mixture was allowed to stir overnight at room temperature. Sodium sulfate decahydrate was added carefully until the evolution of gas subsided. After stirring for 1 hour, the mixture was filtered through a CELITE™ pad and the filtrate was concentrated. Recrystallization (ethyl ether/hexanes) gave the title alcohol (20.67 g, 93%) as a white solid.

$^1$H-NMR (CDCl$_3$) δ 4.04–4.26 (m, 2H), 3.49 (d, 2H, J=6.4 Hz), 2.70 (brt, 2H, J=12.0 Hz), 1.6–1.73 (m, 3H), 1.47 (s, 9H), 1.15 (ddd, 2H, J=23.2 Hz, J=12.0 Hz, J=4.3 Hz).

c) 4-Iodomethyl-1-piperidinecarboxylic acid, 1-(1,1-dimethylethyl)ester

Triphenylphosphine (31.0 g, 0.119 mol) was added to a mixture of iodine (29.0 g, 0.114 mol) in benzene (1 L). After 5 min, pyridine (18.5 ml, 0.228 mol) followed by the alcohol formed in step b (20.5 g, 0.095 mol) was added. The resulting mixture was heated to reflux for 1.5 hours. The cooled reaction mixture was filtered, and the filtrate was washed with saturated sodium thiosulfate ($Na_2S_2O_3$) and brine, and dried (magnesium sulfate), filtered, and concentrated. Purification by silica gel chromatography (10%→20% ethyl acetate/hexanes) gave the title iodide (28.5 g, 92%) as a clear oil. Upon cooling, a white solid was obtained.

M.p.: 58°–59° C.

$^1$H-NMR (CDCl$_3$) δ 4.09 (br d, 2H, J=13.1 Hz), 3.08 (d, 2H, J=6.5 Hz), 2.66 (br t, 2H, J=13.1 Hz), 1.80 (br d, 2H, J=12.9 Hz), 1.52–1.64 (m, 1H), 1.43 (s, 9H), 1.11 (ddd, 2H, J=24.7 Hz, J=12.7 Hz, J=4.3 Hz).

d) 4-[2-[1,2-Benzisoxazol-3-yl]ethyl]-1-piperidinecarboxylic acid, 1-(1,1-dimethylethyl)ester A mixture of 3-methyl-1,2-benzisoxazole (0.410 g, 3.08 mmol) and the iodide formed in step c (1.05 g, 3.23 mmol) in dry THF (3.2 mL) was cooled to −78° C. Freshly prepared 1M lithium diisopropylamide (LDA) (3.1 mL, 3.1 mmol) was added dropwise and the resulting yellow-orange solution was stirred for 25 min at −78° C. Saturated ammonium chloride was added and the mixture was extracted with ethyl acetate (3 times). The combined organic layer was washed with brine and then dried (MgSO$_4$), filtered, and concentrated. Purification by silica gel flash chromatography (10%→20% ethyl acetate/hexanes) gave the title compound (0.430 g, 42%) as a colorless oil.

$^1$H-NMR (CDCl$_3$) δ 7.62 (d, 1H, J=8.0 Hz), 7.49–7.55 (m, 2H), 7.25–7.31 (m, 1H), 4.09 (m, 2H), 3.00 (t, 2H, J=7.8 Hz), 2.66 (br t, 2H, J=13.0 Hz), 1.71–1.84 (m, 4H), 1.47–1.53 (m, 1H), 1.43 (s, 9H), 1.14 (ddd, 2H, J=24.5 Hz, J-12.1 Hz, J=4.1 Hz).

e) 3-[2-[1-(Phenylmethyl)-4-piperidinyl]ethyl]-1,2-benzisoxazole maleate

Trifluoroacetic acid (TFA) (7 mL) was added dropwise to a cold (0° C.) solution of the piperidine formed in step d (0.50 g, 1.51 mmol) in methylene chloride (7 mL). The resulting solution was stirred at 0° C. for 30 min. Volatiles were removed under reduced pressure and excess TFA was removed by concentrating from toluene twice. The crude product was redissolved in methylene chloride (10 mL) and then triethylamine (0.42 mL, 3.01 mmol) and benzyl bromide (0.18 mL, 1.51 mmol) were added. The resulting mixture was stirred overnight (15 hours) at room temperature. The mixture was washed with water and brine and dried (MgSO$_4$), filtered, and concentrated. Purification by silica gel flash chromatography (50% ethyl acetate/hexanes) gave the title compound (free base) (0.350 g, 73%) as a colorless oil.

The maleate salt was prepared by adding a solution of maleic acid (0.108 g, 0.930 mmol) in ethyl ether (20 mL) to a solution of the free base (0.297 g, 0.926 mmol) in ethyl ether (20 mL). The white solid formed was collected and rinsed with ethyl ether. Yield: 0.35 g, 87%.

M.p. 146.4°–147.6° C.

EIMS (no parent) 319.1, 303.1, 185.2, 172.1, 91.1

$^1$H NMR (CDCl$_3$) δ 7.60 (d, J=8, 1H), 7.51–7.52 (m, 2H), 7.37–7.49 (m, 5H), 7.25–7.32 (m, 1H), 6.30 (s, 2H), 4.16 (s, 2H), 3.45–3.51 (m, 2H), 2.98 (t, J=7.4, 2H), 2.60–2.70 (m, 2H), 1.84–1.95 (m, 4H), 1.60–1.82 (m, 3H). $^{13}$C NMR δ 169.5, 163.0, 157.7, 135.8, 131.1, 130.1, 130.0, 129.3, 128.5, 123.5, 121.3, 121.1, 110.0, 60.6, 52.1, 32.8, 28.8, 22.1.

IR (KBr) 2944, 2927, 2921, 2499–2518 (broad), 2329–2388 (broad), 1583, 1517, 1473, 1458, 1445, 1438, 1383, 1360, 782 cm$^{-1}$.

Calc'd for $C_{21}H_{24}N_2O \cdot C_4H_4O_4$: C, 68.79; H, 6.47; N, 6.42. Found: C, 68.80; H, 6.35; N, 6.27.

EXAMPLE 2

5-Methyl-3-[2-[1-(phenylmethyl)-4-piperidinyl]ethyl]-1,2-benzisoxazole maleate

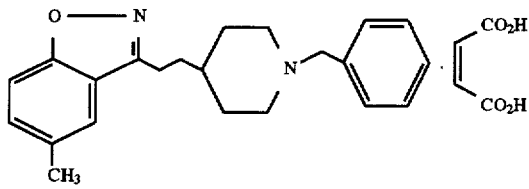

a) 4-[2-[5-Methyl-1,2-benzisoxazol-3-yl]ethyl]-1-piperidinecarboxylic acid, 1-(1,1-dimethylethyl)ester The procedure described in Example 1d was followed using 3,5-dimethyl-1,2-benzisoxazole (0.500 g, 3.40 mmol), 4-iodomethyl-1-piperidinecarboxylic acid, 1-(1,1-dimethylethyl)ester (1.20 g, 3.74 mmol), and 1M lithium diisopropylamide (LDA) (3.74 mL, 3.74 mmol) in dry THF (5 mL). After purification, the title compound (0.910 g, 78%) was obtained as a clear oil.

$^1$H-NMR (CDCl$_3$) δ 7.28–7.40 (m, 3H), 4.04–4.11 (m, 2H), 2.94 (t, 2H, J=7.8 Hz), 2.64 (br t, 2H, J=12.3 Hz), 2.43 (s, 3H), 1.70–1.99 (m, 4H), 1.42 (s, 9H), 1.41–1.55 (m, 1H), 1.13 (ddd, 2H, J=24.4 Hz, J=12.0 Hz, J=4.1 Hz).

b) 5-Methyl-3-[2-[1-(phenylmethyl)-4-piperidinyl]ethyl]-1,2-benzisoxazole maleate The procedure described in Example 1e was followed using the piperidine formed in step a (0.910 g, 2.64 mmol) and TFA (13 mL) in methylene chloride (CH$_2$Cl$_2$) (13 mL), and triethylamine (3.7 mL, 26.4 mmol) and benzyl bromide (0.32 mL, 2.69 mmol) in methylene chloride (CH$_2$Cl$_2$) (20 mL). After purification, the title compound (free base) (0.56 g, 63%) was obtained as a clear oil.

The maleate salt was prepared by adding a solution of maleic acid (0.20 g, 1.72 mmol) in ethyl ether (Et$_2$O) (10 mL) to a solution of the free base (0.56 g, 1.67 mmol) in Et$_2$O (40 mL). The white solid formed was collected and rinsed with Et$_2$O. Yield: 0.70 g, 93%.

M.p. 149°–151° C.

$^1$H NMR (CDCl$_3$) δ 7.27–7.43 (m, 8H), 6.32 (s, 2H), 4.17 (s, 2H), 3.51 (br d, J=11.6, 2H), 2.96 (t, J=7.3, 2H), 2.66 (br t, J=10.8, 2H), 2.45 (s, 3H), 1.60–1.97 (m, 7H).

$^{13}$C NMR δ 169.4, 161.6, 157.3, 135.7, 133.2, 131.6, 131.0, 130.1, 129.3, 128.4, 121.4, 120.2, 60.6, 52.0, 32.8, 32.7, 28.7, 22.0, 21.1.

IR (KBr) 2934, 2848, 2499, 2362, 1701, 1617, 1572, 1487, 1454, 1357 cm$^{-1}$.

EIMS (no parent) 333.1, 317.2, 185.1, 172.1, 91.1 (base).

Calc'd for C$_{22}$H$_{26}$N$_2$O.C$_4$H$_4$O$_4$: C, 69.32; H, 6.71; N, 6.22. Found: C, 69.18; H, 6.48; N, 6.08.

EXAMPLE 3

5,6-Dimethyl-3-[2-[1-(phenylmethyl)-4-piperidinyl]ethyl]-1,2-benzisoxazole maleate

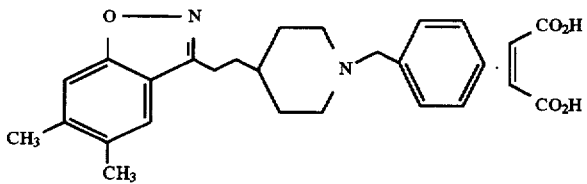

a) 4-[2-[5,6-Dimethyl-1,2-benzisoxazol-3-yl]ethyl]-1-piperidinecarboxylic acid, 1-(1,1-dimethylethyl)ester The procedure described in Example 1d was followed using 3,5,6-trimethyl-1,2-benzisoxazole (0.600 g, 3.73 mmol), 4-iodomethyl-1-piperidinecarboxylic acid, 1-(1,1-dimethylethyl)ester (1.30 g, 4.10 mmol), and 1M LDA (4.10 mL, 4.10 mmol) in dry THF (10 mL). After purification, the title compound (1.04 g, 78%) was obtained as a clear oil.

$^1$H-NMR (CDCl$_3$) δ 7.32 (s, 1H), 7.27 (s, 1H), 4.04–4.10 (m, 2H), 2.93 (t, 2H, J=7.8 Hz), 2.64 (br t, 2H, J=11.9 Hz), 2.35 (s, 3H), 2.32 (s, 3H), 1.70–1.80 (m, 4H), 1.43 (s, 9H), 1.43–1.51 (m, 1H), 1.13 (ddd, 2H, J=24.3 Hz, J=12.3 Hz, J=4.2 Hz).

b) 5,6-Dimethyl-3-[2-[1-(phenylmethyl)-4-piperidinyl]ethyl]-1,2-benzisoxazole maleate The procedure described in Example 1e was followed using the piperidine formed in step a (1.04 g, 2.90 mmol) and TFA (16 mL) in CH$_2$Cl$_2$ (16 mL), and triethylamine (4.2 mL, 29.0 mmol) and benzyl bromide (0.36 mL, 3.03 mmol) in CH$_2$Cl$_2$ (20 mL) After purification, the title compound (free base) (0.53 g, 52%) was obtained as a clear oil.

The maleate salt was prepared by adding a solution of maleic acid (0.18 g, 1.55 mmol) in Et$_2$O (10 mL) to a solution of the free base (0.53 g, 1.52 mmol) in Et$_2$O (25 mL). The white solid formed was collected and rinsed with Et$_2$O. Yield: 0.65 g, 92%.

M.p. 182°–183.5° C.

$^1$H NMR (CDCl$_3$) δ 7.30–7.41 (m, 7H), 6.32 (s, 2H), 4.17 (s, 2H), 3.51 (br d, J=11.8, 2H) 2.95 (t, J=7.2, 2H) 2.65 (br t, J=11.7, 2H), 2.38 (s, 3H), 2.34 (s, 3H), 1.59–1.96 (m, 7H).

$^{13}$C NMR δ 169.4, 162.3, 157.1, 140.2, 135.7, 132.6, 131.1, 130.1, 129.3, 128.3, 120.3, 119.2, 110.0, 60.6, 52.0, 32.7, 28.7, 22.0, 20.9, 19.9.

EIMS 347.2, 331.1, 185.1, 172.1, 91.1, (base)

IR (KBr) 2949, 2914, 2512, 2420, 1580, 1476, 1456, 1449, 1358 cm$^{-1}$.

Calc'd for C$_{23}$H$_{28}$N$_2$O.C$_4$H$_4$O$_4$.¼H$_2$O: C, 69.14; H, 6.93; N, 5.97. Found: C, 69.27; H, 6.83; N, 5.91.

EXAMPLE 4

5-Methoxy-3-[2-[1-(phenylmethyl)-4-piperidinyl]ethyl]-1,2-benzisoxazole maleate

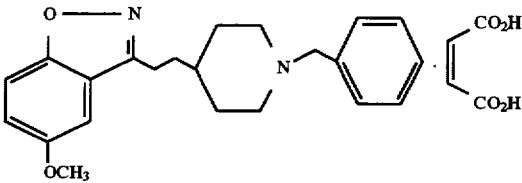

a) 4-[2-[5-Methoxy-1,2-benzisoxazol-3-yl]ethyl]-1-piperidinecarboxylic acid, 1-(1,1-dimethylethyl)ester The procedure described in Example 1d was followed using 5-methoxy-3-methyl-1,2-benzisoxazole (0.32 g, 1.96 mmol), 4-iodomethyl-1-piperidinecarboxylic acid, 1-(1,1-dimethylethyl)ester (0.70 g, 2.15 mmol), and 1M LDA (2.0 mL, 2.0 mmol) in dry THF (2 mL). After purification, the title compound (0.62 g, 87%) was obtained as a clear oil.

$^1$H-NMR (CDCl$_3$) δ 7.46 (d, 1H, J=9.1 Hz), 7.17 (dd, 1H, J=9.1 Hz, J=2.5 Hz), 6.96 (d, 1H, J=2.4 Hz), 4.09–4.16 (m, 2H), 3.87 (s, 3H), 2.99 (t, 2H, J=7.8 Hz), 2.69 (br t, 2H, J=12.3 Hz), 1.74–1.85 (m, 4H), 1.46–1.64 (m, 1H), 1.46 (s, 9H), 1.17 (ddd, 2H, J=22.3 Hz, J=12.2 Hz, J=4.2 Hz).

b) 5-Methoxy-3-[2-[1-(phenylmethyl)-4-pieridinyl]ethyl]-1,2-benzisoxazole maleate The procedure described in Example 1e was followed using the piperidine formed in step a (0.58 g, 1.61 mmol) and TFA (7 mL) in CH$_2$Cl$_2$ (7 mL), and triethylamine (0.50 mL. 3.6 mmol) and benzyl bromide (0.195 mL, 1.64 mmol) in CH₂Cl₂ (10 mL). After purification, the title compound, free base (0.27 g, 48%) was obtained as a clear oil.

The maleate salt was prepared by adding a solution of maleic acid (0.080 g, 0.69 mmol) in Et₂O (10 mL) to a solution of the free base (0.24 g, 0.68 mmol) in Et₂O (20 mL). The white solid formed was collected and rinsed with Et₂O. Yield: 0.29 g, 91%.

M.p. 143.5°–145° C.

$^1$H NMR (CDCl₃) δ 7.35–7.42 (m, 6H), 7.13 (dd, $J_1$=9.1, $J_2$=2.5, 1H), 6.92 (d, J=2.4, 1H), 6.30 (s, 2H), 4.17 (s, 2H), 3.83 (s, 3H), 3.46–3.51 (m, 2H), 2.94 (t, J=7.3, 2H), 2.60–2.80 (m, 2H), 1.60–1.96 (m, 7H).

$^{13}$C NMR δ 169.4, 158.4, 157.6, 156.3, 135.8, 131.0, 130.0, 129.2, 128.4, 121.5, 120.3, 110.6, 101.1, 60.5, 56.0, 52.0, 32.7, 32.5, 28.7, 22.0.

IR (KBr) 2942, 2927, 2916, 2518, 2366, 1616, 1572, 1544, 1521, 1480, 1454, 1443, 1384, 1357, 1220 cm$^{-1}$.

EIMS 349.2, 333.2, 318.1, 259.1, 185.1, 172.1, 91.1 (base).

Calc'd for C₂₂H₂₆N₂O₂·C₄H₄O₄: C, 66.94; H, 6.48; N, 6.00. Found: C, 67.21; H, 6.52; N, 5.94.

EXAMPLE 5

6-Methoxy-3-[2-[1-(phenylmethyl)-4-piperidinyl]ethyl]-1,2-benzisoxazole

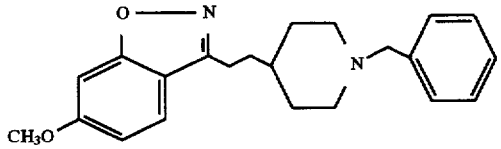

a) 4-[2-[6-Methoxy-1,2-benzisoxazol-3-yl]ethyl]-1-piperidinecarboxylic acid, 1-(1,1-dimethylethyl)ester The procedure described in Example 1d was followed using 6-methoxy-3-methyl-1,2-benzisoxazole (0.32 g, 1.96 mmol), 4-iodomethyl-1-piperidinecarboxylic acid, 1-(1,1-dimethylethyl)ester (0.70 g, 2.15 mmol), and 1M LDA (2.0 mL, 2.0 mmol) in dry THF (3 mL). After purification, the title compound (0.57 g, 80%) was obtained as a white solid.

M.p.: 95°–96° C.

$^1$H-NMR (CDCl₃) δ 7.47 (d, 1H, J=8.7 Hz), 6.99 (d, 1H, J=2.1 Hz) 6.91 (dd, 1H, J=8.6 Hz, J=2.1 Hz), 4.08–4.11 (m, 2H), 3.89 (s, 3H), 2.97 (t, 2H, J=7.8 Hz), 2.68 (br t, 2H, J=12.7 Hz), 1.72–1.84 (m, 4H), 1.46–1.60 (m, 1H), 1.46 (s, 9H), 1.16 (ddd, 2H, J=24.6 Hz, J=12.3 Hz, J=4.3 Hz).

b) 6-Methoxy-3-[2-[1-(phenylmethyl)-4-piperidinyl]ethyl]-1,2-benzisoxazole

The procedure described in Example 1e was followed using the piperidine formed in step a (0.49 g, 1.36 mmol) and TFA (7 mL) in CH₂Cl₂ (7 mL), and triethylamine (0.85 mL, 6.1 mmol) and benzyl bromide (0.165 mL, 1.39 mmol) in CH₂Cl₂ (8 mL). After purification, the title compound (0.265 g, 55%) was obtained as a white solid.

M.p. 90.5°–91.5° C.

$^1$H NMR (CDCl₃) δ 7.47 (d, J=8.7, 1H), 7.21–7.33 (m, 5H), 6.98 (d, J=1.8, 1H), 6.90 (dd, $J_1$=8.7, $J_2$=2.0, 1H), 3.88 (s, 3H), 3.50 (s, 2H), 2.88–2.98 (m, 4H), 1.96 (br t, J=10.6, 2H), 1.74–1.83 (m, 4H), 1.27–1.34 (m, 3H).

$^{13}$C NMR δ 164.8, 162.0, 158.3, 138.4, 129.2, 128.1, 126.9, 121.4, 115.0, 113.8, 92.6, 63.4, 55.7, 53.7, 35.3, 34.3, 32.6, 22.6.

IR (KBr) 2924, 2913, 2797, 2758, 1625, 1608, 1276, 1196, 1154, 734 cm$^{-1}$.

EIMS 349.2, 333.6, 259.1, 185.1, 172.1, 91.0 (base).

Calc'd for C₂₂H₂₆N₂O₂: C, 75.40; H, 7.48; N, 7.99. Found: C, 75.52; H, 7.63; N, 7.94.

EXAMPLE 6

7-Methoxy-3-[2-[1-(phenylmethyl)-4-piperidinyl]ethyl]-1,2-benzisoxazole fumarate

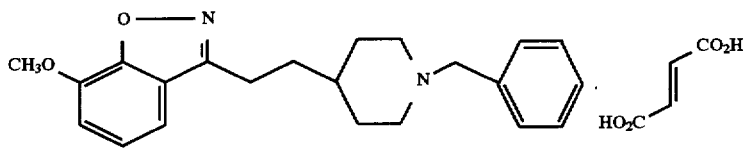

a) 4-[2-[7-Methoxy-1,2-benzisoxazol-3-yl]ethyl-1-piperidinecarboxylic acid, 1-(1,1-dimethylethyl)ester The procedure described in Example 1d was followed using 7-methoxy-3-methyl-1,2-benzisoxazole (0.30 g, 1.84 mmol), 4-iodomethyl-1-piperidinecarboxylic acid, 1-(1,1dimethylethyl)ester (0.60 g, 1.85 mmol), and 1M LDA (1.9 mL, 1.9 mmol) in dry THF (2 mL). After purification, the title compound (0.41 g, 62%) was obtained as a pale yellow oil.

$^1$H-NMR (CDCl₃) δ 7.12–7.19 (m, 2H), 6.91 (dd, 1H, J=6.5 Hz, J=2.2 Hz), 3.98–4.07 (m, 2H), 3.98 (s, 3H), 2.95 (t, 2H, J=7.8 Hz), 2.62 (br t, 2H, J=12.2 Hz), 1.67–1.78 (m, 4H), 1.40–1.48 (m, 1H), 1.40 (s, 9H), 1.10 (ddd, 2H, J=24.5 Hz, J=12.5 Hz, J=4.3 Hz).

b) 7-Methoxy-3-[-2-[1-(phenylmethyl)-4-piperidinyl]ethyl]-1,2-benzisoxazole fumarate The procedure described in Example 1e was followed using the piperidine formed in step a (0.40 g, 1.11 mmol) and TFA (6 mL) in CH₂Cl₂ (6 mL), and triethylamine (0.34 mL, 2.44 mmol) and benzyl bromide (0.14 mL, 1.18 mmol) in CH₂Cl₂ (10 mL). After purification, the title compound (free base) (0.080 g, 21%) was obtained as a clear oil.

The fumarate salt was prepared by adding a solution of fumaric acid (0.025 g, 0.213 mmol) in ethanol (EtOH) (2 mL) to a solution of the free base (0.071 g, 0.203 mmol) in Et₂O (10 mL). Upon concentration to 4–5 mL, a white/pink solid precipitated. This solid was collected and rinsed with Et₂O. Yield: 0.065 g, 69%.

M.p. 138°–139° C.

$^1$H NMR (CDCl₃) δ 7.27–7.41 (m, 7H), 7.19 (d, J=7.7, 1H), 6.59 (s, 2H), 3.97 (s, 3H), 3.65 (s, 2H), 2.90–3.01 (m, 4H), 2.18 (br t, J=10.8, 2H), 1.67–1.77 (m, 4H), 1.26–1.32 (m, 3H).

$^{13}$C NMR δ 166.6, 158.8, 152.4, 144.0, 136.5, 134.4, 129.4, 128.3, 127.5, 124.9, 122.9, 113.2, 111.4, 61.5, 56.2, 52.6, 34.3, 33.4, 30.7, 22.0.

HRMS Calc'd (free base) 350.1992. Found: 350.1984.

IR (KBr) 1705, 1531, 1266, 756, 642 cm$^{-1}$.

Calc'd for C₂₂H₂₆N₂O₂·C₄H₄O₄: C, 66.94; H, 6.48; N, 6.00. Found: C, 66.76; H, 6.31; N, 5.61.

EXAMPLE 7

6-Acetamido-3-[2-[1-(phenylmethyl)-4-piperidinyl]ethyl]-1,2-benzisoxazole hemifumarate

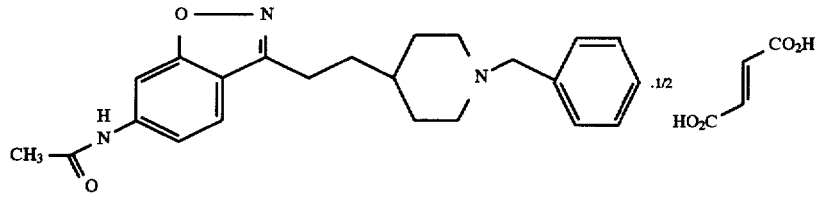

a) 4-[2-[6-Acetamido-1,2-benzisoxazol-3-yl]ethyl] piperidinecarboxylic acid, 1-(1,1-dimethylethyl)ester Freshly prepared 1M LDA (11.0 mL, 11.0 mmol) was added dropwise and quickly to a cold (−78° C.) solution of 6-N-acetyl-3-methylbenzisoxazole (1.0 g, 5.26 mol) in THF (50 mL). Immediately after addition was complete, a solution of 4-iodomethyl-1-piperidinecarboxylic acid, 1-(1,1-dimethylethyl)ester (1.71 g, 5.26 mmol) in THF (8 mL) was added all at once. The resulting yellow-orange solution was stirred for 30 minutes at −78° C. Saturated ammonium chloride (NH$_4$Cl) was added and the mixture was extracted with ethyl acetate (EtOAc) (3 times). The combined organic layer was washed with brine, dried over magnesium sulfate (MgSO$_4$), filtered, and concentrated.

Purification by silica gel flash chromatography (20%→50% EtOAc/CH$_2$Cl$_2$) gave the title compound (1.56 g, 76%) as a white solid.

M.p.: 142°–143° C.

$^1$H-NMR (CDCl$_3$) δ 8.76 (s, 1H), 8.05 (s, 1H), 7.48 (d, 1H, J=8.5 Hz), 7.32 (dd, 1H, J=8.6 Hz, J=1.5 Hz), 4.06 (br d, 2H, J=11.5 Hz), 2.94 (t, 2H, J=7.8 Hz), 2.66 (br t, 2H, J=11.8 Hz), 2.20 (s, 3H), 1.69–1.80 (m, 4H), 1.41–1.47 (m, 1H), 1.44 (s, 9H), 1.12 (ddd, 2H, J=23.8 Hz, J=12.0 Hz, J=3.9 Hz).

b) 6-Acetamido-3-[2-[1-(phenylmethyl)-4-piperidinyl]ethyl]-1,2-benzisoxazole fumarate Trifluoroacetic acid (TFA) (4 mL) was added dropwise to a cold (0° C.) solution of the piperidine formed in step a (0.40 g, 1.03 mmol) in CH$_2$Cl$_2$ (8 mL). The resulting solution was stirred at 0° C. for 30 min. Volatiles were removed under reduced pressure and excess TFA was removed by concentrating from toluene twice. The crude product was redissolved in CH$_2$Cl$_2$ (10 mL) and triethylamine (1.44 mL, 10.3 mmol) and benzyl bromide (0.184 mL, 1.55 mmol) was added. The resulting mixture was stirred for 6 hours at room temperature. The mixture was washed with water and brine and dried (MgSO$_4$), filtered, and concentrated. Purification by silica gel flash chromatography (CH$_2$Cl$_2$→10% MeOH/CH$_2$Cl$_2$) gave the title compound (free base) (0.270 g, 69%) as a white solid.

The fumarate salt was prepared by adding a solution of fumaric acid (0.091 g, 0.788 mmol) in ethanol (EtOH) (5 mL) to a solution of the free base (0.270 g, 0.716 mmol) in CH$_2$Cl$_2$ (20 mL). After concentrating, the solid obtained was recrystallized from EtOH to give white needles. Yield: 0.17 g, 48%.

M.p. 225°–226° C.

$^1$H NMR (DMSO-d$_6$) δ 10.37 (s, 1H), 8.13 (s, 1H), 7.76 (d, 1H, J=8.5), 7.25–7.36 (m, 6H), 6.59 (s, 2H), 3.54 (s, 2H), 2.83–2.96 (m, 4H), 2.10 (s, 3H), 2.01 (br t, 2H, J=11.1), 1.69–1.73 (m, 4H), 1.20–1.28 (m, 3H).

Calc'd for C$_{23}$H$_{27}$N$_3$O$_2$.½C$_4$H$_4$O$_4$.¼H$_2$O: C, 68.24; H, 6.76; N, 9.55. Found: C, 68.35; H, 6.63; N, 9.35.

EXAMPLE 8

6-Amino-3-[2-[1-(phenylmethyl)-4-piperidinyl]ethyl]-1,2-benzisoxazole maleate

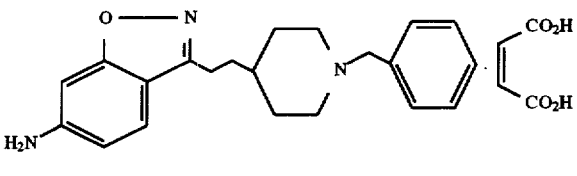

A mixture of 6-acetamido-3-[2-[1-(phenylmethyl)-4-piperidinyl]ethyl]-1,2-benzisoxazole (0.30 g, 0.79 mmol) in 1N HCl (10 mL) was heated to reflux for 30 min. The cooled reaction mixture was made basic with 10% NaOH and extracted with EtOAc (2 times). The combined organic layer was washed with brine and dried (MgSO$_4$), filtered, and concentrated to give the title compound (free base) (0.259 g, 98%) as an oil.

The mono maleate salt was prepared by adding a solution of maleic acid (0.099 g, 0.85 mmol) in EtOH (5 ml) to a solution of the free base (0.26, 0.77 mmol) in CH$_2$Cl$_2$ (3 mL). After concentrating, the residue was triturated with Et$_2$O to give a white powder. Yield: 0.29 g, 64%.

M.p. 173.0°–173.5° C.

$^1$H NMR (DMSO-d$_6$) δ 7.41–7.47 (m, 6H), 6.58–6.63 (m, 2H), 6.06 (s, 2H), 5.87 (br s, 2H), 4.26 (s, 2H), 3.29–3.38 (m, 2H), 2.80–2.95 (m, 4H), 1.90 (br d, J=12.5, 2H) 1.25–1.80 (m, 5H).

$^{13}$C NMR (DMSO-d$_6$) 167.4, 164.8, 157.4, 151.9, 136.0, 131.2, 130.1, 129.5, 128.9, 121.9, 112.8, 110.7, 90.9, 59.3, 51.5, 32.6, 32.6, 28.6, 21.6.

EIMS (no parent) 289, 268, 218, 190 (base).

IR (KBr) 3483, 3384, 2929, 2526, 1633, 1619, 1582, 1515, 1474, 1459, 1438, 1389, 1379, 1359, 877, 702 cm$^{-1}$.

Calc'd for C$_{21}$H$_{25}$N$_2$O.C$_4$H$_4$O$_4$: C, 66.50; H, 6.47; N, 9.31. Found: C, 66.49; H, 6.43; N, 9.22.

EXAMPLE 9

6-Benzaamide-3-[2-[1-(phenylmethyl)-4-piperidinyl]ethyl]-1,2-benzisoxazole maleate

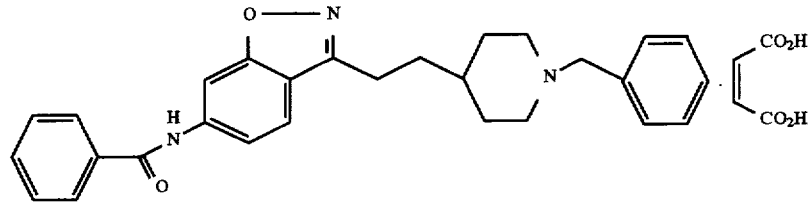

a) 6-Benzamide-3-methyl-1,2-benzisoxazole

Benzoyl chloride (0.56 mL, 4.82 mmol) was added to a solution of 6-amino-3-[2-[1-(phenylmethyl)-4-piperidinyl]ethyl]-1,2-benzisoxazole (0.70 g, 4.72 mmol), triethylamine (1.35 mL, 9.69 mmol), and 4-dimethylaminopyridine (0.07 g, 0.57 mmol) in $CH_2Cl_2$ (30 mL). The resulting mixture was stirred overnight at room temperature. The heterogenous mixture was concentrated, and the solid obtained was collected and washed with water and ether and air-dried to give the title compound (1.02 g, 86%) as an off-white solid. A small sample was purified by recrystallization from EtOH to give pure white flakes.

M.p.: 213°–214° C.

$^1$H-NMR (DMSO-$d_6$) δ 10.6 (s, 1H), 8.30 (s, 1H), 7.98 (d, 2H, J=6.9 Hz), 7.80 (d, 1H, J=8.6 Hz), 7.68 (d, 1H, J=8.8 Hz), 7.52–7.63 (m, 3H), 2.53 (s, 3H).

b) 4-[2-[6-Benzamide-1,2-benzisoxazole-3-yl]ethyl]-1-piperidinecarboxylic acid, 1-(1,1-dimethylethyl)ester The procedure described in Example 7a was followed using the benzamide formed in step a (1.0 g, 3.96 mmol), 1M LDA (7.95 mL, 7.95 mmol), and 4-iodomethyl-1-piperidinecarboxylic acid, 1-(1,1-dimethylethyl)ester (1.30 g, 4.00 mmol) in dry THF (50 mL), except that after addition of reagents, the mixture was stirred at −78° C. for 1.5 hours. After purification by chromatography (30%→50% EtOAc/hexanes), the title compound (1.54 g, 87%) was obtained as a pale yellow solid. A small sample was purified by recrystallization ($CH_2Cl_2/Et_2O$) to give a white solid.

M.p.: 177°–178.5° C.

$^1$H-NMR (CDCl$_3$) δ 8.61 (s, 1H), 8.15 (s, 1H), 7.86 (d, 2H, J=7.4 Hz), 7.39–7.53 (m,5H), 4.03 (br d, 2H, J=12.7 Hz), 2.92 (t, 2H, J=8.0 Hz), 2.50–2.73 (m, 2H), 1.60–1.80 (m, 4H), 1.40–1.45 (m, 1H), 1.41 (s, 9H), 1.13 (ddd, 2H, J=24.0 Hz, J=12.2 Hz, J=3.8 Hz).

c) 6-Benzamide-3-[2-[1-(phenylmethyl)-4-peridinyl]ethyl]-1,2-benzisoxazole maleate Trifluoroacetic acid (TFA) (8.4 mL) was added dropwise to a cold (0° C.) solution of the piperidine formed in step b (0.70 g, 1.56 mmol) in $CH_2Cl_2$ (10 mL). The resulting solution was stirred at 0° C. for 30 min. Volatiles were removed under reduced pressure and excess TFA was removed by concentrating from toluene twice. The crude product was dissolved in THF (10 mL) and triethylamine (2.1 mL, 15.1 mmol) followed by benzyl bromide (0.21 mL, 1.77 mmol) was added. The resulting mixture was diluted with ethyl acetate and stirred overnight at room temperature. The mixture was then washed with water and brine and dried (MgSO$_4$), filtered, and concentrated. Purification by silica gel flash chromatography (30% EtOAc/$CH_2Cl_2$→100% EtOAc) gave the title compound (free base) (0.280 g, 41%) as a pale yellow solid.

The maleate salt was prepared by adding a solution of maleic acid (0.081 g, 0.702 mmol) in EtOH (5 mL) to a solution of the free base (0.280 g, 0.638 mmol) in $CH_2Cl_2$ (20 mL). After concentrating, the solid obtained was recrystallized from EtOH/$CH_2Cl_2$ to give a white solid. Yield: 0.208 g, 59%.

M.p. 181.5°–183.0° C.

$^1$H NMR (DMSO-$d_6$) δ 10.65 (s, 1H), 8.31 (s, 1H), 7.98 (d, J=7.2, 2H), 7.85 (d, J=8.6, 1H), 7.48–7.71 (m, 9H), 6.03 (s, 2H), 4.25 (br s, 2H), 3.20–3.60 (m, 4H), 2.89–3.02 (t, @ 2.99, J=7.5 and m, 4H), 1.40–1.97 (m, 7H).

$^{13}$C NMR (DMSO-$d_6$) δ 167.2, 166.2, 163.0, 158.1, 141.5, 135.9, 134.6, 132.0, 131.2, 129.5, 128.9, 128.5, 127.8, 121.9, 117.01, 116.8, 99.9, 59.5, 51.7, 32.8, 32.5, 28.8, 21.7.

EIMS 439.2, 422.2 (100), 383, 348, 293, 185.

IR (KBr) 2934, 2919, 1657, 1610, 1579, 1536, 1499, 1491, 1462, 1453, 1352 cm$^{-1}$.

Calc'd for $C_{28}H_{29}N_3O_2 \cdot C_4H_4O_4$: C, 69.17; H, 5.99; N, 7.56. Found: C, 68.81; H, 5.90; N, 7.49.

EXAMPLE 10

6-Benzenesulfonamide-3-[2-[1-(phenylmethyl)-4-piperidinyl]ethyl]-1,2-benzisoxazole fumarate

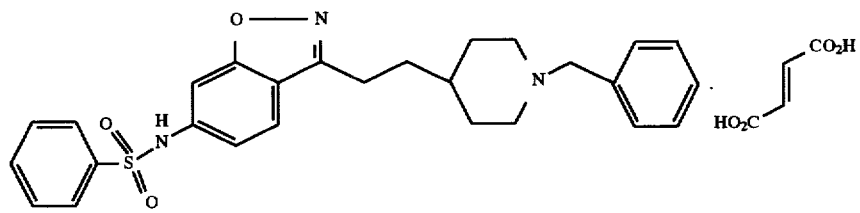

a) 6-Benzenesulfonamide-3-methyl-1,2-benzisoxazole

Benzenesulfonyl chloride (0.528 mL, 4.14 mmol) was added to a cold (0° C.) solution of 6-amino-3-[2-[1-(phenylmethyl)-4-piperidinyl]ethyl]-1,2-benzisoxazole (0.613 g, 4.14 mmol) and pyridine (0.670 mL, 8.28 mmol) in $CH_2Cl_2$ (30 mL). After 1.3 hours, saturated sodium bicarbonate (NaHCO$_3$) was added and the resulting mixture was stirred overnight at room temperature. The organic layer

37 was separated and washed with water and brine and dried (MgSO₄), filtered, and concentrated. Purification by silica gel flash chromatograph (5% EtOAc/CH₂Cl₂) gave the title compound (0.867 g, 83%) as a white solid.

M.p.: 183°–184° C.

¹H-NMR (CDCl₃) δ 10.9 (br s, 1H), 7.84 (d, 2H, J=6.7 Hz), 7.68 (d, 1H, J=8.5 Hz), 7.52–7.63 (m, 3H), 7.34 (d, 1H, J=1.5 Hz), 7.11 (dd, 1H, J=8.5 Hz, J=1.7 Hz), 2.52 (s, 3H).

b) 4-[2-[6-Benzenesulfonamide-1,2-benzisoxazol-3-yl]ethyl]-1-piperidinecarboxylic acid, 1-(1,1-dimethylethyl) ester The procedure described in Example 7a was followed using the benzenesulfonamide formed in step a (0.60 g, 2.08 mmol), 1M LDA (4.58 mL, 4.58 mmol), and 4-iodomethyl-1-piperidinecarboxylic acid, 1-(1-dimethylethyl)ester (0.813 g, 2.50 mmol) in dry THF (70 mL), except that after addition of reagents, the mixture was stirred at −78° C. for 10–15 min. After purification by chromatography (20%→40% EtOAc/hexanes), the title compound (0.997 g, 99%) was obtained as a white foam.

M.p.: 66°–67° C.

¹H-NMR (CDCl₃) δ 7.85 (dd, 2H, J=8.3 Hz, J=1.6 Hz), 7.35–7.57 (m,6H), 7.02 (dd, 1H, J=8.5 Hz, J=1.6 Hz), 4.11 (br d, 2H, J=13.2 Hz), 2.94 (t, 2H, J=7.4 Hz), 2.68 (br t, 2H, J=12.8 Hz), 1.71–1.77 (m, 4H), 1.46 (s, 9H), 1.46–1.55 (m, 1H), 1.15 (ddd, 2H, J=23.6 Hz, J=11.7 Hz, J=3.9 Hz).

c) 6-Benzenesulfonamide-3-[2-[1-(phenylmethyl)-4-piperidinyl]ethyl]-1,2-benzisoxazole fumarate Trimethylsilyl trifluoromethanesulfonate (1.30 mL, 6.76 mmol) was added dropwise to a cold (0° C.) solution of the piperidine formed in step b (0.819 g, 1.69 mmol) and 2,6-lutidine (0.590 mL, 5.07 mmol) in CH₂Cl₂ (17 mL). After 1.5 hours, saturated sodium bicarbonate (NaHCO₃) was added and the resulting mixture was stirred at room temperature for 15 min. The white precipitate formed was collected by filtration and redissolved in water at pH 2. This acidic aqueous layer was extracted with CH₂Cl₂ (2 times) and EtOAc (1 time). All organic layers were combined, dried (MgSO₄), filtered, and concentrated. The crude white solid obtained was suspended in THF (30 mL) and DMF (50 mL), and triethylamine (0.40 mL, 2.86 mmol) and benzyl bromide (0.22 mL, 1.86 mmol) were added. The resulting heterogenous mixture was stirred at room temperature for 24 hours (with time a more homogenous mixture was obtained). The mixture was concentrated, and CH₂Cl₂ was added to the residue. The organic layer was washed with water and brine and dried (MgSO₄), filtered, and concentrated. Purification by silica gel flash chromatography (CH₂Cl₂→5% MeOH/CH₂Cl₂) gave the title compound (free base) (0.334 g, 49%) as a white foam.

The fumarate salt was prepared by adding a solution of fumaric acid (0.040 g, 0.345 mmol) in EtOH (3 mL) to a solution of the free base (0.150 g, 0.315 mmol) in CH₂Cl₂ (6 mL). After concentrating, the residue was triturated with Et₂O to give a white solid. Yield: 0.151 g, 81%.

¹H NMR (DMSO-d₆) δ 7.82 (d, 2H, J=7.0), 7.70 (d, 1H, J=8.6), 7.51–7.60 (m, 3H), 7.27–7.32 (m, 6H), 7.07 (dd, 1H, J₁=8.6, J₂=1.6), 6.59 (s, 2H), 3.55 (s, 2H), 2.82–2.90 (m, 4H), 2.03 (br t, 2H, J=11.5), 1.61–1.70 (m, 4H), 1.20–1.25 (m, 3H).

38

EXAMPLE 11

6-(4-Morpholinyl)-3-[2-[1-(phenylmethyl)-4-piperidinyl]-ethyl]-1,2-benzisoxazole

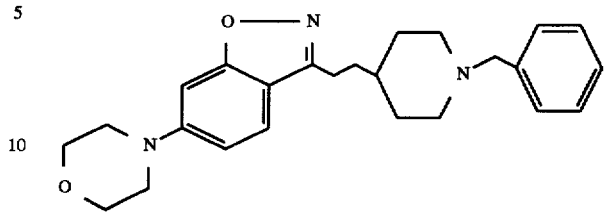

a) 3-Methyl-6-(4-morpholinyl)-1,2-benzisoxazole

A mixture of 6-amino-3-[2-[1-(phenylmethyl)-4-piperidinyl]ethyl]-1,2-benzisoxazole (0.230 g, 1.55 mmol), β,β'-dibromodiethyl ether (0.397 g, 1.71 mmol), and diisopropylethyl amine (Hunig's base, 0.648 mL, 3.72 mmol) in toluene (2.5 mL) was heated at 120° C. for 15 hours. The cooled reaction mixture was diluted with EtOAc and washed with water and brine and dried (MgSO₄), filtered, and concentrated. Two additional separate reactions using 6-amino-3-[2-[1-(phenylmethyl)-4-piperidinyl]ethyl]-1,2-benzisoxazole (0.050 g, 0.34 mmol, and 0.150 g, 1.01 mmol) were carried out in the same manner. Crude product from the three reactions was combined and purified by silica gel flash chromatography (1% MeOH/CH₂Cl₂) to give the title compound (0.499 g, 79% combined yield) as a pale yellow solid. A small sample was further purified by recrystallization (EtOAc/hexanes) to give a white solid.

M.p.: 138.5°–139.5° C.

¹H-NMR (CDCl₃) δ 7.46 (d, 1H, J=8.7 Hz), 6.95 (dd, 1H, J=8.7 Hz, J=2.0 Hz), 6.90 (d, 1H, J-1.9 Hz), 3.88 (t, 4H, J=4.9 Hz), 3.27 (t, 4H, J=4.8 Hz), 2.52 (s, 3H).

b) 4-[2-[6-(4-Morpholinyl)-1,2-benzisoxazol-3-yl]ethyl]-1-piperidinecarboxylic acid, 1-(1,1-dimethylethyl)ester The procedure described in Example 7a was followed using the morpholino derivative formed in step a (0.369 g, 1.69 mmol), 1M LDA (1.86 mL, 1.86 mmol), and 4-iodomethyl-1-piperidinecarboxylic acid, 1-(1,1-dimethylethyl)ester (0.605 g, 1.86 mmol) in dry THF (8 mL). Another reaction with the above morpholino derivative (0.100 g, 0.46 mmol) was also carried out. Crude product from both reactions was combined and after purification by chromatography (5%→40% EtOAc/hexanes), the title compound (0.477 g, 53%) was obtained as a white solid. A small sample was further purified by recrystallization (EtOAc/hexanes) to give a white solid.

M.p.: 164°–165° C.

¹H-NMR (CDCl₃) δ 7.46 (d, 1H, J=8.6 Hz), 6.92–6.97 (m, 2H), 4.02–4.15 (m, 2H), 3.89 (t, 4H, J=4.9 Hz), 3.27 (t, 4H, J=4.9 Hz), 2.95 (t, 2H, J-7.8 Hz), 2.7 (br t, 2H, J=12.1 Hz), 1.74–1.80 (m, 4H), 1.46–1.56 (m, 1H), 1.46 (s, 9H), 1.10–1.22 (m, 2H).

c) 6-(4-Morpholinyl)-3-[2-[1-(phenylmethyl)-4-piperidinyl]ethyl]-1,2-benzisoxazole Trifluoroacetic acid (TFA) (5 mL) was added to a cold (0° C.) solution of the piperidine formed in step b (0.40 g, 0.96 mmol) and thioanisole (1.13 mL, 9.60 mmol) in CH₂Cl₂ (10 mL). The resulting mixture was stirred at 0° C. for 30 min. Volatiles were removed under reduced pressure and 1N sodium hydroxide (NaOH) was added to the residue. The aqueous layer was extracted with EtOAc (2 times) and the combined organic layer was washed with water and brine and dried (MgSO₄), filtered, and concentrated. The yellow oil obtained was redissolved in CH₂Cl₂ (10 mL), and triethylamine (0.267 mL, 1.92 mmol) and benzyl bromide (0.148 mL, 1.25 mmol) were added. The resulting mixture was stirred overnight at room temperature. The mixture was washed with water and brine and dried (MgSO₄), filtered, and concentrated. Purification by silica gel flash chromatography (CH₂Cl₂→10% MeOH/(CH₂Cl₂) gave the title compound (0.285 g, 73%) as a white solid. A small sample was further purified by recrystallization (EtOH) to give a white solid.

M.p. 129°–130° C.

¹H NMR (CDCl₃) δ 7.44 (d, J=8.7, 1H), 7.23–7.30 (m, 5H), 6.89–6.93 (m, 2H), 3.87 (t, J=4.8, 4H), 3.47 (s, 2H), 3.25 (t, J=4.8, 4H), 2.85–2.94 (m, 4H), 1.92 (br t, J=10.8, 2H), 1.72–1.79 (m, 4H), 1.21–1.31 (m, 3H).

¹³C NMR 165, 158, 153.4, 138.8, 129.2, 128.1, 126.9, 121.3, 113.3, 94.5, 66.7, 63.5, 53.7, 49.1, 35.3, 34.4, 32.1, 22.7.

IR (KBr) 3020, 2920, 1950, 1895, 1815, 1722, 1620, 1450, 1250, 1122, 738 cm⁻¹.

Calc'd for C₂₅H₃₁N₃O₂: C, 74.04; H, 7.70; N, 10.36. Found: C, 73.75; H, 7.69; N, 10.36.

EXAMPLE 12

5,7-Dihydro-3-[2-[1-(phenylmethyl)-4-piperidinyl]ethyl]-6H-pyrrolo[4,5-f]-1,2-benzisoxazol-6-one maleate

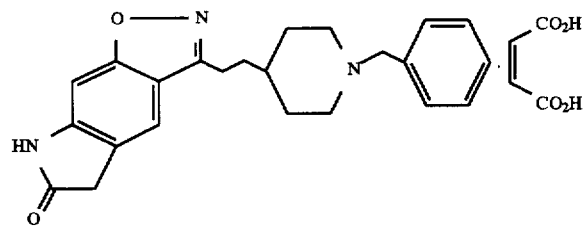

a) 5-Acetyl-1,3-dihydro-6-hydroxy-2H-indol-2-one

Acetyl chloride (4.09 mL, 0.0575 mol) was added to a slurry of aluminum trichloride (AlCl₃) (35.36 g, 0.265 mol) in carbon disulfide (CS₂) (250 mL). After 2–3 min, 6-methoxyoxindole (7.22 g, 0.0442 mol) was added. The resulting mixture was heated to reflux for 2.5 hours. (A black tar developed with time). Excess solvent was decanted and ice water was added carefully to the residue. The resulting mixture was stirred overnight. The pale yellow solid obtained was collected, washed with water and dried under high vacuum to give the title compound (7.32 g, 87%).

¹H-NMR (DMSO-d₆) δ 13.0 (s, 1H), 10.8 (s, 1H), 7.70 (s, 1H), 6.30 (s, 1H), 3.40 (s, 2H), 2.54 (s, 3H).

b) 5-Acetyl-1,3-dihydro-6-hydroxy-2H-indol-2-one, 5-oxime

An aqueous solution of hydroxylamine hydrochloride (8.26 g, 0.119 mol) and sodium acetate trihydrate (16.9 g, 0.124 mol) was a added to a mixture of the ketone formed in step a (9.88 g, 0.0517 mol) in EtOH (600 mL). The resulting mixture was heated to reflux for 20 hours. The hot reaction mixture was filtered and the solid collected was rinsed with EtOH. After drying, the title compound (10.11 g, 95%) was obtained as a pale yellow solid.

¹H-NMR (DMSO-d₆) δ 12.0 (s, 1H), 11.4 (s, 1H), 10.5 (s, 1H), 7.29 (s, 1H), 6.35 (s, 1H), 3.38 (s, 2H), 2.20 (s, 3H).

c) 5-Acetyl-1,3-dihydro-6-hydroxy-2H-indol-2-one, 5-oxime acetate

A heterogenous mixture of the oxime formed in step b (7.15 g, 34.7 mmol) in acetic anhydride (55 mL) was heated at 80° C. for 2 hours. The cooled reaction mixture was filtered and the solid collected was rinsed with water. After drying, the title compound (4.67 g, 54%) was obtained as a pale yellow solid.

¹H-NMR (DMSO-d₆) δ 11.3 (s, 1H), 10.6 (s, 1H), 7.35 (s, 1H), 6.44 (s, 1H), 3.41 (s, 2H), 2.37 (s, 3H), 2.21 (s, 3H).

d) 5,7-Dihydro-3-methyl-6H-pyrrolo[4,5-f]-1,2-benzisoxazol-6-one

A mixture of the oxime acetate formed in step c (4.48 g, 18.0 mmol) and pyridine (14.6 mL, 180 mmol) in dimethylformamide (DMF) (660 mL) was heated at 125°–130° C. for 4 hours. The cooled reaction mixture was poured over water and extracted with EtOAc (4 times). The combined organic layer was washed with water and brine and dried (MgSO₄), filtered, and concentrated. Purification by silica gel flash chromatography (50% EtOAc/hexanes→100% EtOAc) gave the title compound (2.20 g, 65%) as a pale yellow-orange solid.

M.p. (EtOAc): 264°–265° C. (dec).

¹H-NMR (DMSO-d₆) δ 10.8 (s, 1H), 7.60 (s, 1H), 6.98 (s, 1H), 3.57 (s, 2H), 2.47 (s, 3H).

e) 4-[2-[5,7-Dihydro-6H-pyrrolo[4,5-f]-1,2-benzisoxazol-6-one-3-yl]ethyl]-1-piperidinecarboxylic acid, 1-(1,1-dimethylethyl)ester The procedure described in Example 7a was followed using the benzisoxazole formed in step d (2.33 g, 12.4 mmol), 1M LDA (40.9 mL, 40.9 mmol), and 4-iodomethyl-1-piperidine-carboxylic acid, 1-(1,1-dimethylethyl)ester (4.42 g, 13.6 mmol) in dry THF (500 mL), except that after addition of reagents, the mixture was stirred at −78° C. for 4 hours. Purification by chromatography (20%→30% EtOAc/CH₂Cl₂) gave recovered starting material (0.210 g, 9%) and the title compound (2.75 g, 58%) as an off-white solid.

¹H-NMR (CDCl₃) δ 8.48 (s, 1H), 7.44 (s, 1H), 7.03 (s, 1H), 4.08–4.14 (m, 2H), 3.63 (s, 2H), 2.97 (t, 2H, J=7.8 Hz), 2.69 (br t, 2H, J=12.8 Hz), 1.74–1.84 (m, 4H), 1.46–1.55 (m, 1H), 1.46 (s, 9H), 1.18 (ddd, 2H, J=24.4 Hz, J=12.1 Hz, J=4.3 Hz).

f) 5,7-Dihydro-3-[2-[1-(phenylmethyl)-4-peridinyl]ethyl]-6H-pyrrolo[4,5-f]-1,2-benzisoxazol-6-one maleate Trifluoroacetic acid (TFA) (3.3 mL) was added dropwise to a cold (0° C.) solution of the piperidine formed in step e (0.50 g, 1.30 mmol) in CH₂Cl₂ (13 mL). After 30 min, the mixture was concentrated and excess TFA was removed by concentrating from toluene (2 to 3 times). The crude residue was dissolved in DMF (12.5 mL) and sodium carbonate (Na₂CO₃) (0.689 g, 6.50 mmol) and benzyl bromide (0.186 mL, 1.56 mmol) were added. The resulting mixture was stirred at room temperature for 4 hours. The reaction was filtered and the filtrate was concentrated in vacuo. The residue was dissolved in methylene chloride and washed with brine, and dried (MGSO₄), filtered, and concentrated. Purification by silica gel chromatography (CH₂Cl₂→10% methanol/CH₂Cl₂) gave the title compound (free base) (0.343 g, 70%) as a white solid.

The maleate salt was prepared by adding a solution of maleic acid (0.061 g, 0.528 mmol) in ethanol (EtOH) (1 mL) to a solution of the free base (0.180 g, 0.48 mmol) in CH₂Cl₂ (10 mL). After concentrating, the salt was purified by recrystallization from isopropanol to give an off-white solid. Yield: 0.173 g, 73%.

M.p. 194°–195° C.

¹H NMR (DMSO-d₆) δ 10.82 (s, 1H), 7.65 (s, 1H), 7.48 (s, 5H), 7.00 (s, 1H), 6.03 (s, 1H), 4.24 (br s, 2H), 3.58 (s, 2H), 3.25–3.38 (m, 2H), 2.94 (t, 2H, J=7.6), 2.81–2.97 (m, 2H), 1.86–1.96 (m, 2H), 1.62–1.76 (m, 2H), 1.30–1.60 (m, 3H).

Calc'd for C₂₃H₂₅N₃O₂·C₄H₄O₄: C, 65.97; H, 5.95; N, 8.55. Found: C, 65.98; H, 6.04; N, 8.54.

EXAMPLE 13

1-[2-[1-(Phenylmethyl)-4-piperidinyl]ethyl]-isoquinoline maleate

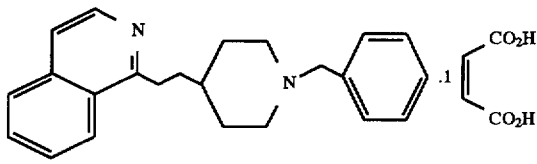

a) 4-[2-[1-Isoquinolyl]ethyl]-1-piperidinecarboxylic acid, 1-(1,1-dimethylethyl)ester The procedure described in Example 7a was followed using 1-methyl isoquinoline (0.50 g, 3.49 mmol), 1M LDA (4.2 mL, 4.2 mmol), and 4-iodomethyl-1-piperidinecarboxylic acid, 1-(1,1-dimethylethyl)ester (1.2 g, 3.84 mmol) in dry THF (45 mL) except that after addition of the reagents, the mixture was stirred at –78° C. for 1.75 hours. Purification by chromatography (30% EtOAc/toluene) gave the title compound (0.784 g, 66%) as a yellow oil.

$^1$H-NMR (CDCl$_3$) δ 8.38 (d, 1H, J=5.8 Hz), 8.08 (d, 1H, J=8.3 Hz), 7.77 (d, 1H, J=8.0 Hz), 7.62 (t, 1H, J=7.1 Hz), 7.54 (t, 1H, J=7.1 Hz), 7.46 (d, 1H, J=5.7 Hz), 4.08 (br s, 2H), 3.25–3.30 (m, 2H), 2.67 (br t, 2H, J=12.3 Hz), 1.73–1.81 (m, 4H), 1.49–1.63 (m, 1H), 1.42 (s, 9H), 1.17 (ddd, 2H, J=24.6 Hz, J=12.1 Hz, J=3.8 Hz).

b) 1-[2-[1-(Phenylmethyl)-4-piperidinyl]ethyl]isoquinoline maleate

The procedure described in Example 1e was followed using the piperidine formed in step a (0.713 g, 2.10 mmol) and TFA (7 mL) in CH$_2$Cl$_2$ (14 mL), and triethylamine (2.9 mL, 21.0 mmol) and benzyl bromide (0.275 mL, 2.31 mmol) in CH$_2$Cl$_2$ (60 mL). After purification (CH$_2$Cl$_2$→5% MeOH/CH$_2$Cl$_2$), the title compound (free base) (0.26 g, 38%) was obtained as a pale yellow oil.

The mono maleate salt was prepared by adding a solution of maleic acid (0.10 g, 0.867 mmol) in EtOH (3 mL) to a solution of the free base (0.26 g, 0.788 mmol) in CH$_2$Cl$_2$ (7 mL). After concentrating, the salt was purified by recrystallization [cold (0°) EtOAc] to give an off-white solid. Yield: 0.195 g, 56%.

$^1$H NMR (DMSO-d$_6$) δ 8.39 (d, 1H, J=5.7), 8.26 (d, 1H, J=8.3), 7.97 (d, 1H, J=8.1), 7.77 (t, 1H, J=7.4), 7.66–7.71 (m, 2H), 7.49 (s, 5H), 6.05 (s, 2H), 4.28 (br s, 2H), 3.27–3.32 (m, 2H), 2.87–2.90 (m, 2H), 1.76–2.03 (m, 6H), 1.55–1.69 (m, 1H), 1.33–1.46 (m, 2H).

EXAMPLE 14

3-[2-[1-(Phenylmethyl)-4-piperidinyl]ethyl]-1,2-benzisothiazole maleate

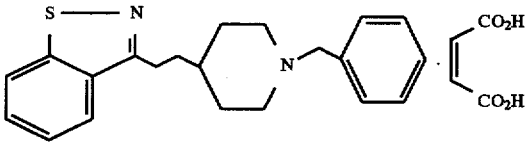

a) 4-[2-[1,2-Benzisothiazol-3-yl]ethyl]-1-piperidinecarboxylic acid, 1-(1,1-dimethylethyl)ester The procedure described in Example 1d was followed using 3-methyl-1,2-benzisothiazole (0.50 g, 3.35 mmol), 4-iodomethyl-1-piperidinecarboxylic acid, 1-(1,1-dimethylethyl)ester (1.20 g, 3.69 mmol), and 1M lithium diisopropylamide (LDA) (3.35 mL, 3.35 mmol) in dry THF (100 mL). After purification, the title compound (0.582 g, 50%) was obtained as a pale yellow oil.

$^1$H-NMR (CDCl$_3$) δ 7.91–7.96 (m, 2H), 7.43–7.52 (m, 2H), 4.05–4.14 (m, 2H), 3.15 (t, 2H, J=7.9 Hz), 2.69 (br t, 2H, J=12.1 Hz), 1.74–1.88 (m, 4H), 1.46–1.60 (m, 1H), 1.46 (s, 9H), 1.29–1.10 (m, 2H).

b) 3-[2-[1-(Phenylmethyl)-4-piperidinyl]ethyl]-1,2-benzisothiazole maleate

The procedure described in Example 1e was followed using the piperidine formed in step a (0.102 g, 0.29 mmol) and trifluoroacetic acid (TFA) (0.75 mL) in methylene chloride (CH$_2$Cl$_2$) (3 mL), and triethylamine (0.202 mL, 1.45 mmol) and benzyl bromide (0.038 mL, 0.32 mmol) in methylene chloride (CH$_2$Cl$_2$) (3 mL). After purification, the title compound (free base) (0.058 g, 62%) was obtained as a clear oil.

The maleate salt was prepared by adding a solution of maleic acid (0.020 g, 0.17 mmol) in EtOH (3 mL) to a solution of the free base (0.058 g, 0.17 mmol) in CH$_2$Cl$_2$ (3 mL). The resulting mixture was concentrated and the residue was triturated with Et$_2$O. The white solid obtained was filtered and collected to give the title compound (0.077 g, 96%).

$^1$H-NMR (CDCl$_3$) δ 8.14–8.21 (m, 2H), 7.63 (t, J=7.4, 1H), 7.50–7.55 (m, 6H), 6.04 (s, 2H), 4.26 (br s, 2H), 3.35 (br s, 2H), 3.15 (t, J=7.6, 2H), 2.80–2.92 (m, 2H), 1.92–2.00 (m, 2H), 1.78–1.88 (m, 2H), 1.54–1.65 (m, 1H), 1.35–1.45 (m, 2H).

M.p.: 175°–176° C.

$^{13}$C-NMR (DMSO-d$_6$) δ 167.3, 166.2, 151.6, 136.0, 134.2, 131.2, 130.1, 129.5, 128.9, 127.9, 124.9, 123.6, 120.6, 59.4, 51.6, 32.5, 33.5, 28.9, 27.8.

IR (KBr) 3030, 2910, 2350, 1700, 1575, 1445, 1350 cm$^{-1}$.

EIMS: 336.2 (M+, free base), 319.1, 245.1, 185.1, 172.1, 91.0 (base).

Anal. Calcd. for C$_{21}$H$_{24}$N$_2$S.C$_4$H$_4$O$_4$: C, 66.35; H, 6.24; N, 6.19. Found: C, 66.21; H, 5.93; N, 6.03.

EXAMPLE 15

4-[2-[1-(Phenylmethyl)-4-piperidyl]ethyl]-1,3-quinazoline maleate

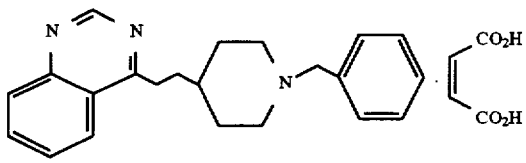

a) 4-[2-[1,3-Quinazol-4-yl]ethyl]-1-piperidinecarboxylic acid, 1-(1,1-dimethylethyl)ester Freshly made 1M LDA (4.2 mL, 4.2 mmol) was added to a solution of 4-methyl-1,3-quinazoline (0.60 g, 4.2 mmol) in THF (35 mL) at 0° C. To the yellow solution obtained, was added neat trimethylsilyl chloride (0.53 mL, 4.2 mmol). The ice bath was removed and the reaction was allowed to stir for 3 min. The mixture was re-cooled to 0° C., and a second equivalent of 1M LDA (4.2 mL, 4.2 mmol) was added. Next, a solution of 4-iodomethyl-1-piperidinecarboxylic acid, 1-(1,1-dimethylethyl)ester (1.49 g, 4.6 mmol) in THF (10 mL) was added and stirring was continued at 0° C. for 1 hour. Dilute HCl (1N) was added and the mixture was stirred at room temperature for 30 min. The reaction was made basic by addition of 1N NaOH and extracted with EtOAc. The organic layer was washed with brine, dried (MgSO$_4$), filtered, and concentrated. Purification by silica gel flash chromatography (20→50% EtOAc-hexanes) gave the title compound (0.466 g, 33%) as an oil.

¹H-NMR (CDCl₃) δ 9.21 (s, 1H), 8.12 (d, 1H, J=7.7 Hz), 8.05 (d, 1H, J=8.4 Hz), 7.90 (t, 1H, J=7.8 Hz), 7.65 (t, 1H, J=7.7 Hz), 4.08–4.17 (m, 2H), 3.32 (t, 2H, J=8.3 Hz), 2.72 (br t, 2H, J=12.1 Hz), 1.78–1.90 (m, 4H), 1.57–1.59 (m, 1H), 1.47 (s, 9H), 1.18–1.29 (m, 2H).

b) 4-[2-[1-(Phenylmethyl)-4-piperidyl]ethyl]-1,3-quinazoline maleate

The procedure described in Example 1e was followed with the piperidine obtained in step a (0.429 g, 1.26 mmol) and TFA (3.5 mL) in CH₂Cl₂ (13 mL), and triethylamine (0.88 mL, 6.3 mmol) and benzyl bromide (0.17 mL, 1.39 mmol) in CH₂Cl₂ (22 mL). After purification by chromatography (CH₂Cl₂→10% MeOH—CH₂Cl₂), the title compound, free base (0.179 g, 43%) was obtained as a colorless oil.

The maleate salt was prepared by adding a solution of maleic acid (0.052 g, 0.45 mmol) in Et₂O (10 mL) to a solution of the free base (0.135 g, 0.41 mmol) in Et₂O (200 mL). The white solid obtained was collected by filtration to give the title compound (0.103 g, 56%).

M.p.: 121°–122° C.

¹H-NMR (DMSO-d₆) δ 9.16 (s, 1H), 8.33 (d, 1H, J=8.4 Hz), 7.98–8.01 (m, 2H), 7.72–7.78 (m, 1H), 7.43 (s, 5H), 6.02 (s, 2H), 4.08 (br s, 2H), 3.32 (t, 2H, J=7.7 Hz), 3.15–3.35 (m, 2H), 2.60–2.80 (m, 2H), 1.89–1.94 (m, 2H), 1.76–1.79 (m, 2H), 1.30–1.60 (m, 3H).

IR (KBr) 3037, 2923, 1705, 1571, 1386 cm⁻¹.

EIMS: 331 (M+, free base), 318, 248, 143, 77 (base).

Anal. Calcd. for $C_{22}H_{25}N_3 \cdot C_4H_4O_4$: C, 69.78; H, 6.53; N, 9.39. Found: C, 69.46; H, 6.61; N, 9.26.

EXAMPLE 16

6-Hydroxy-3-[2-[1-(phenylmethyl)-4-piperidyl]ethyl]-1,2-benzisoxazole

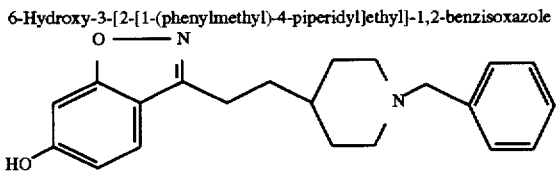

A mixture of 6-methoxy-3-[2-[1-(phenylmethyl)-4-piperidinyl]ethyl]-1,2-benzisoxazole (0.1.1 g, 0.288 mmol) in 48% aqueous HBr (10 mL) was heated at 110° C. for 16 hours. The mixture was made basic by addition of saturated NaHCO₃ and extracted with CH₂Cl₂. The organic layer was dried (MgSO₄), filtered, and concentrated. Purification by silica gel flash chromatography (3→6% MeOH—CH₂Cl₂) gave the title compound (0.055 g, 57%) as a white solid.

M.p.: 148°–149° C.

¹H-NMR (CDCl₃) δ 7.70 (br s, 1H), 7.27–7.37 (m, 6H), 6.74–6.80 (m, 2H), 3.63 (s, 2H), 3.04 (br d, 2H, J=10.8 Hz), 2.88 (t, 2H, J=7.7 Hz), 2.05–2.20 (m, 2H), 1.65–1.95 (m, 4H), 1.30–1.60 (m, 3H).

IR (KBr) 3080, 3040, 2945, 1624, 1437, 1384 cm⁻¹.

EIMS: 336.2 (M+), 319.2, 255.0, 185.1, 91.1 (base).

HRMS calcd. for $C_{21}H_{24}N_2O_2$: 336.18382. Found: 336.18187.

EXAMPLE 17

6-Bromo-3-[2-[1-(phenylmethyl)-4-piperidyl]ethyl]-1,2-benzisoxazole maleate

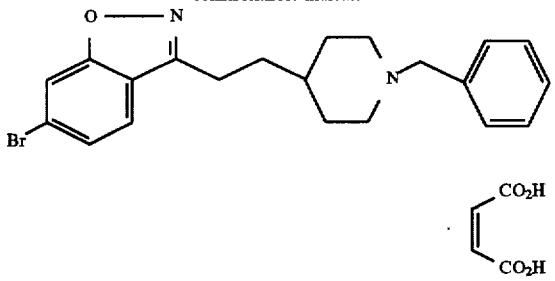

a) 4-[2-[6-Bromo-1,2-benzisoxazol-3-yl]ethyl]-1-piperidinecarboxylic acid, 1-(1,1-dimethylethyl)ester The procedure described in Example 1d was followed with 6-bromo-3-methyl-1,2-benzisoxazole (1.02 g, 4.81 mmol), 4-iodomethyl-1-piperidinecarboxylic acid, 1-(1,1-dimethylethyl)ester (1.72 g, 5.29 mmol), and 1M LDA (5.30 mL, 5.30 mmol) in dry THF (40 mL), except that after addition of reagents, the mixture was stirred at −78° C. for 1.5 hours. After purification, the title compound (0.697 g, 35%) was obtained as a pale yellow solid.

¹H-NMR (CDCl₃) δ 7.77 (s, 1H), 7.52 (d, 1H, J=7.2 Hz), 7.45 (d, 1H, J=7.2 Hz), 4.11 (br d, 2H, J=14.3 Hz), 3.02 (t, 2H, J=7.2 Hz), 2.70 (dt, 2H, J=12.9 Hz, J=3.6 Hz), 1.70–1.85 (m, 4H), 1.49 (s, 9H), 1.45–1.55 (m, 1H), 1.09–1.29 (m, 2H).

b) 6-Bromo-3-[2-[1-(phenylmethyl)-4-piperidinyl]ethyl]-1,2-benzisoxazole maleate The procedure described in Example 1e was followed with the piperidine formed in step a (0.398 g, 0.972 mmol) and TFA (4 mL) in CH₂Cl₂ (26 mL), and triethylamine (1.6 mL, 11.8 mmol) and benzyl bromide (0.155 mL, 1.3 mmol) in CH₂Cl₂ (12 mL). Another reaction with the above piperidine (0.102 g, 0.249 mmol) was also carried out. Crude product from both reactions was combined and after purification, the title compound, free base (0.021 g, 4%) was obtained as a tan solid.

The maleate salt was prepared by adding a solution of maleic acid (0.023 g, 0.198 mmol) in EtOH (5 mL) to a solution of the free base (0.072 g, 0.18 mmol) in CH₂Cl₂ (6 mL). After concentration, the residue was recrystallized from EtOH to give the title compound (0.035 g, 38%) as a white solid.

M.p.: 156.8°–157.5° C.

¹H-NMR (DMSO-d₆) δ 8.08 (s, 1H), 7.87 (d, 1H, J=8.4 Hz), 7.58 (d, 1H, J=8.5 Hz), 7.47 (s, 5H), 6.03 (s, 2H), 4.23 (br s, 2H), 3.25–3.40 (m, 2H), 3.02 (t, 2H, J=7.5 Hz), 2.80–2.95 (m, 2H), 1.88–2.00 (m, 2H), 1.70–1.80 (m, 2H), 1.30–1.60 (m, 3H).

¹³C-NMR (DMSO-d₆) δ 167.2, 162.8, 158.6, 136.0, 131.1, 129.5, 128.9, 127.0, 124.0, 123.7, 120.6, 113.1, 59.6, 51.9, 32.7, 28.9, 21.6.

EIMS: 398 (M+), 381, 309, 252, 200, 185 (base), 172, 91.

HRMS calc'd for $C_{21}H_{23}BrN_2O$: 398.0994. Found: 398.0941.

EXAMPLE 18

6-Cyano-3-[2-[1-(phenylmethyl)-4-piperidyl]ethyl]-1,2-benzisoxazole

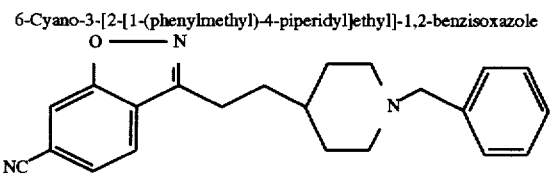

A solution of $NaNO_2$ (0.112 g, 1.62 mmol) in $H_2O$ (4 mL) was added to a solution of 6-amino-3-[2-[1-(phenylmethyl)-4-piperidinyl]ethyl]-1,2-benzisoxazole (0.534 g, 1.59 mmol) in 28% HCl (20 mL) kept at 0° C. The resulting mixture was neutralized to pH 7 by cautious addition of solid $Na_2CO_3$. The neutral mixture was added in portions to a well-stirred mixture of toluene (75 mL), ice, and a freshly prepared solution of CuCN (organic Synthesis, Coll. Vol. I, p. 514; $CuSO_4$: 0.318 g, 1.99 mmol). The mixture obtained was kept at 0° C. for 30 minutes, then at room temperature for 2 hours, and finally, heated at 50° C. for 5 minutes. The mixture was extracted with ethyl acetate and the organic phase was washed with $H_2O$, brine, dried ($MgSO_4$), filtered, and concentrated. Purification by silica gel flash chromatography (3% MeOH—$CH_2Cl_2$) gave the title compound (0.236 g, 43%) as a pale orange solid. Recrystallization (EtOH-hexanes) of a small sample gave the title compound as an off-white solid.

M.p.: 113°–114.5° C.

$^1$H-NMR ($CDCl_3$) δ 7.89 (s, 1H), 7.77 (d, 1H, J=8.4 Hz), 7.57 (d, 1H, J=8.7 Hz), 7.24–7.33 (m, 5H), 3.51 (s, 2H), 3.04 (t, 2H, J=7.9 Hz), 2.92 (br d, 2H, J=11.2 Hz), 1.97 (br t, 2H, J=10.7 Hz), 1.74–1.85 (m, 4H), 1.26–1.40 (m, 3H).

$^{13}$C-NMR ($CDCl_3$) δ 161.7, 158.8, 129.2, 128.2, 127.0, 126.3, 125.1, 122.5, 118.1, 114.5, 113.2, 63.4, 53.6, 35.2, 34.0, 32.0, 22.6.

IR ($CHCl_3$) 2830, 2720, 2160, 1600, 1425, 1385 $cm^{-1}$.

FABMS: 346 (M++1), 309, 275, 239, 155, 119 (base).

HRMS calc'd for $C_{22}H_{23}N_3O$: 345.1842. Found: 345.1826.

EXAMPLE 19

6-Carboxamide-3-[2-[1-(phenylmethyl)-4-piperidyl]ethyl]-1,2-benzisoxazole

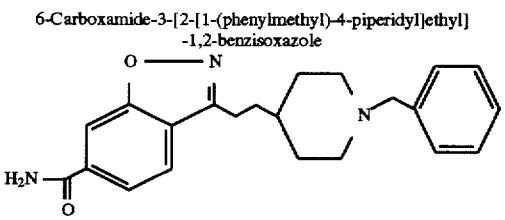

Powdered KOH (0.150 g, 2.68 mmol) was added to a mixture of 6-cyano-3-[2-[1-(phenylmethyl)-4-piperidyl]ethyl]-1,2-benzisoxazole (0.250 g, 0.724 mmol) in t-BuOH (10 mL). The resulting mixture was heated at 85° C. for 20 minutes. The cooled reaction mixture was poured over brine and extracted with $CH_2Cl_2$. The organic phase was washed with 10% NaOH, brine, dried ($MgSO_4$), filtered, and concentrated. The crude product was purified by recrystallization (EtOAc-hexanes) to give the title compound (0.114 g, 43%) as a white solid.

M.p.: 181°–182° C.

$^1$H-NMR (DMSO-$d_6$) δ 8.20 (br s, 1H, —NH), 8.15 (s, 1H), 7.97 (d, 1H, J=8.4 Hz), 7.87 (d, 1H, J=8.1 Hz), 7.64 (br s, 1H—NH), 7.22–7.31 (m, 5H), 3.42 (s, 2H), 3.02 (t, 2H, J=7.8 Hz), 2.78 (br d, 2H, J=11.5 Hz), 1.87 (br t, 2H, J=10.9 Hz), 1.69–1.73 (m, 4H), 1.22–1.26 (m, 3H).

$^{13}$C-NMR (DMSO-$d_6$) δ 167.1, 162.0, 158.9, 138.9, 136.3, 128.7, 126.8, 126.8, 123.3, 122.9, 122.0, 108.7, 62.5, 53.2, 34.9, 33.7, 31.6, 22.0.

FABMS: 346 [(M++1), base], 321, 272, 185, 172.

EXAMPLE 20

3-[(1-Phenylmethyl-4-piperidyl)methoxy]-1,2-benzisoxazole fumarate

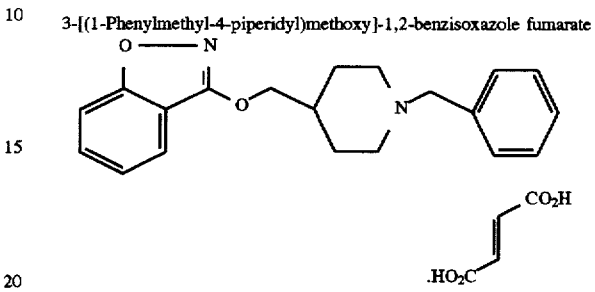

a) 4-[(1,2-Benzisoxazol-3-yl)oxymethyl]-1-piperidinecarboxylic acid, 1-(1,1-dimethylethyl)ester NaH (60% mineral oil dispersion, 0.941 g, 23.53 mmol) was added in portions to a solution of 4-hydroxymethyl-1-piperidinecarboxylic acid, 1-(1,1-dimethylethyl)ester (4.82 g, 22.41 mmol) in DMF (220 mL) at 0° C. After 10 minutes, the reaction was warmed to room temperature and 3-chloro-1,2-benzisoxazole (3.44 g, 22.41 mmol) was added. The mixture obtained was heated at 115° C. for 16 hours. The reaction mixture was diluted with EtOAc and washed with $H_2O$ (4×), brine, dried ($MgSO_4$), filtered, and concentrated. Purification by silica gel flash chromatography (10% EtOAc-hexanes) gave the title compound (4.16 g, 56%) as a white solid.

M.p.: 103°–104.5° C.

$^1$H-NMR ($CDCl_3$) δ 7.61 (d, 1H, J=7.9 Hz), 7.48–7.54 (m, 1H), 7.41 (d, 1H, J=8.5 Hz), 7.22–7.27 (m, 1H), 4.28 (d, 2H, J=6.5 Hz), 4.16 (br d, 2H, J=13.3 Hz), 2.75 (dt, 2H, J=13.2 Hz, J=2.6 Hz), 2.04–2.13 (m, 1H), 1.83 (br d, 2H, J=13.7 Hz), 1.45 (s, 9H), 1.30 (ddd, 2H, J=24.9 Hz, J=12.5 Hz, J=4.2 Hz).

b) 3-[(1-Phenylmethyl-4-piperidyl)methoxy]-1,2-benzisoxazole fumarate

Trifluoroacetic acid (TFA) (10 mL) was added dropwise to a solution of piperidine formed in step a (0.827 g, 2.49 mmol) in $CH_2Cl_2$ (25 mL) at 0° C. The resulting mixture was stirred at 0° C. for 20 minutes. The mixture was concentrated, and excess TFA was removed by concentrating from toluene. The residue was partitioned between $CH_2Cl_2$ and saturated $NaHCO_3$. The organic layer was dried ($MgSO_4$), filtered, and concentrated. The crude product (0.192 g, 0.827 mmol) was dissolved in $CH_2Cl_2$ (8 mL), and triethylamine (0.58 mL, 4.13 mmol) followed by benzyl bromide (0.128 mL, 1.07 mmol) was added. The mixture was stirred overnight (18 hours) at room temperature. The reaction was washed with $H_2O$, brine, dried ($MgSO_4$), filtered, and concentrated. Purification by silica gel flash chromatography (5% MeOH—$CH_2Cl_2$) gave the title compound, free base (0.199 g, 25%) as an off-white solid.

The fumarate salt was prepared by adding fumaric acid (0.074 g, 0.633 mmol) dissolved in the minimum amount of EtOH to a solution of the free base (0.186 g, 0.58 mmol) in $CH_2Cl_2$ (6 mL). After concentrating, the crude salt was purified by recrystallization (EtOH—$Et_2O$) to give the title compound (0.134 g, 53%) as an off-white solid.

M.p.: 163°–164° C.

¹H-NMR (DMSO-d₆) δ 7.74 (d, 1H, J=7.8 Hz), 7.61–7.69 (m, 2H), 7.26–7.41 (m, 6H), 6.60 (s, 2H), 4.28 (d, 2H, J=6.4 Hz), 3.65 (s, 2H), 2.97 (br d, 2H, J=11.4 Hz), 2.20 (br t, 2H, J=11.7 Hz), 1.90–2.05 (m, 1H), 1.81 (brd, 2H, J=12.8 Hz), 1.38–1.49 (m, 2H).

¹³C-NMR (DMSO-d₆) δ 166.5, 166.1, 163.3, 137.0, 134.3, 131.1, 129.3, 128.3, 127.3, 123.6, 120.8, 113.5, 110.3, 74.2, 61.7, 52.2, 34.7, 27.6.

IR (KBr) 2980, 2550, 1706, 1650, 1616, 1573, 1447, 1374 cm⁻¹.

EIMS: 305, 185, 172, 91 (base).

HRMS calc'd. for C₂₀H₂₂N₂O₂ (freebase): 322.1682. Found: 322.1719.

Anal. Calc'd. for C₂₀H₂₂N₂O₂·C₄H₄O₄·0.75H₂O: C, 63.78; H, 6.13; N, 6.20. Found: C, 63.88; H, 5.85; N, 6.14.

EXAMPLE 21

3-[(1-Phenylmethyl-4-piperidyl)methylamino]-1,2-benzisoxazole

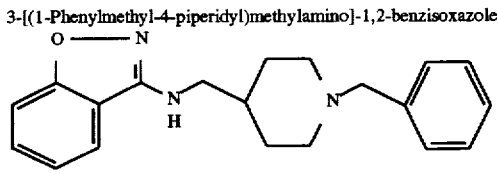

A mixture of 3-chloro-1,2-benzisoxazole (0.238 g, 1.55 mmol), 4-aminomethyl-1-phenylmethyl piperidine (0.316 g, 1.55 mmol), and K₂CO₃ (0.214 g, 1.55 mmol) in DMSO (10 mL) was heated at 150° C. for 20 hours. The cooled reaction mixture was diluted with EtOAc (75 mL) and poured over H₂O (200 mL). The organic phase was separated and washed with brine, dried (MgSO₄), filtered, and concentrated. The brown oil obtained was purified by silica gel flash chromatography (4% MeOH—CH₂Cl₂) to give the title compound (0.084 g, 17%) as pale yellow oil.

¹H-NMR (CDCl₃): δ 7.44–7.50 (m, 2H), 7.38 (d, 1H, J=8.8 Hz), 7.16–7.31 (m, 6H), 4.35–4.42 (m, 1H, —NH—), 3.51 (s, 2H), 3.33 (t, 2H, J=6.2 Hz), 2.92 (br d, 2H, J=11.5 Hz), 1.99 (t, 2H, J=11.6 Hz), 1.77 (br d, 2H, J=12.7 Hz), 1.75–1.80 (m, 1H), 1.33–1.45 (m, 2H).

¹³C-NMR (CDCl₃) δ 162.8, 158.6, 137.8, 129.8, 129.3, 128.2, 127.2, 122.1, 119.7, 116.2, 110.1, 63.2, 53.3, 49.4, 35.2, 29.9, 29.7.

IR (KBr) 3290, 2924, 2852, 1614, 1564, 1450, 1365 cm⁻¹.

EIMS: 321 (M+), 230, 201, 185, 172, 91 (base).

HRMS calc'd. for C₂₀H₂₃N₃O: 321.1842. Found: 321.1825.

EXAMPLE 22

3-[2-[(1-Phenylmethyl)-4-piperidyl]ethylamino]-1,2-benzisoxazole

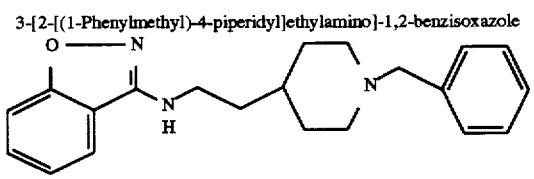

The procedure described in Example 21 was followed with 3-chloro-1,2-benzisoxazole (0.682 g, 4.44 mmol), 4-aminoethyl-1-phenylmethyl piperidine (0.970 g, 4.44 mmol), and K₂CO₃ (0.614 g, 4.44 mmol) in DMSO (30 mL). After purification, the title compound (0.231 g, 15%) was obtained as a pale yellow oil.

¹H-NMR (CDCl₃) δ 7.45–7.54 (m, 2H), 7.24–7.40 (m, 6H), 7.19 (t, 1H, J=7.8 Hz), 4.40 (brt, 1H, J=5.5 Hz), 3.52 (s, 2H), 3.45 (dt, 2H, J=7.4 Hz, J=6.0 Hz), 2.91 (brd, 2H, J=111.8 Hz), 1.99 (brt, 2H, J=11.2 Hz), 1.62–1.73 (m, 4H), 1.37–1.52 (m, 3H).

¹³C-NMR (CDCl₃) δ 162.7, 158.6, 137.8, 129.8, 129.4, 128.2, 127.1, 122.1, 119.8, 116.3, 110.0, 63.3, 53.6, 41.5, 36.1, 33.4, 32.0.

EIMS: 335 (M+), 244, 199, 186, 172, 91 (base).

HRMS calc'd. for C₂₁H₂₅N₃O: 335.1998. Found: 335.1909.

EXAMPLE 23

3-[3-[1-(Phenylmethyl)-4-piperidyl]propyl]-1,2-benzisoxazole maleate

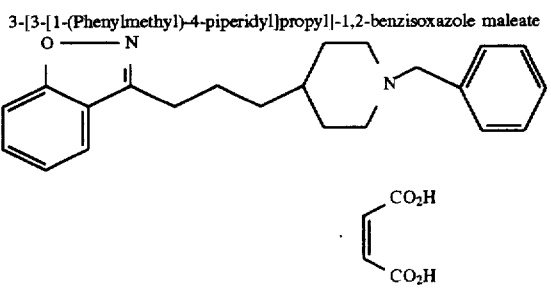

a) 4-(2-Ethoxy-2-oxoethylidine)-1-piperidinecarboxylic acid, 1-(1,1-dimethylethyl)ester A solution of triethyl phosphonoacetate (3.1 mL, 15.69 mmol) in freshly distilled 1,2-dimethoxyethane (DME, 12.5 mL) was added to a slurry of NaH (60% mineral oil dispersion, 0.75 g, 18.18 mmol) in DME (6.5 mL). The mixture obtained was stirred for 1 hour at room temperature and a solution of 4-keto-1-piperidinecarboxylic acid, 1-(1,1-dimethyethyl)ester (2.5 g, 12.55 mmol) in DME (12.5 mL) was added. After stirring overnight (15 hours), the mixture was concentrated. The residue was purified by silica gel flash chromatography (5→20% EtOAc-hexanes) to give the title compound (3.06 g, 91%) as a white solid.

¹H-NMR (CDCl₃) δ 5.71 (s, 1H), 4.16 (q, 2H, J=7.1 Hz), 3.45–3.53 (m, 4H), 2.94 (t, 2H, J=5.7 Hz), 2.28 (t, 2H, J=5.6 Hz), 1.48 (s, 9H), 1.28 (t, 3H, J=7.1 Hz).

b) 4-Ethoxycarbonylmethyl-1-piperidinecarboxylic acid, 1-(1,1-dimethylethyl)ester A mixture of olefin obtained in step a (3.05 g, 11.3 mmol) and 10% Pd/C (1.2 g, 1.13 mmol) in EtOH (50 mL) was hydrogenated in a Parr shaker at 50 psi (3.45 bars) for 1.5 hours. The mixture was filtered through a CELITE™ pad, and the filtrate was concentrated to give the title compound (3.07 g, quantitative) as a colorless oil.

¹H-NMR (CDCl₃) δ 4.14 (q, 2H, J=7.0 Hz), 4.05–4.12 (m, 2H), 2.72 (br dt, 2H, J=12.1 Hz, J=2.8 Hz), 2.23 (d, 2H, J=7.2 Hz), 1.85–1.95 (m, 1H), 1.61–1.66 (m, 2H), 1.45 (s, 9H), 1.26 (t, 3H, J=7.0 Hz), 1.05–1.23 (m, 2H).

c) 4-Hydroxyethyl-1-piperidinecarboxylic acid, 1-(1,1-dimethylethyl)ester

The procedure described in Example 1b was followed with the ester obtained in step b (3.06 g, 11.3 mmol) and lithium aluminum hydride (0.47 g, 12.4 mmol) in THF (105 mL). Purification by silica gel flash chromatography (50% EtOAc-hexanes) gave unreacted starting material (0.73 g, 24%) and the title compound (1.74 g, 68%) as a colorless oil.

¹H-NMR (CDCl₃) 4.07 (br d, 2H, J=14.1 Hz), 3.71 (t, 2H, J=6.5 Hz), 2.69 (brt, 2H, J=12.5 Hz), 1.50–1.70 (m, 6H), 1.45 (s, 9H), 1.05–1.15 (m, 2H).

d) 4-Iodoethyl-1-piperidinecarboxylic acid, 1-(1,1-dimethylethyl)ester

The procedure described in Example 1c was followed with the alcohol obtained in step c (1.74 g, 7.59 mmol), triphenylphosphine (2.49 g, 9.49 mmol), iodine (2.31 g, 9.11 mmol), and pyridine (1.5 mL, 18.2 mmol) in benzene (50 mL). After purification, the title compound (2.27 g, 98%) was obtained as a colorless oil.

$^1$H-NMR (CDCl$_3$) δ 4.09 (br d, 2H, J=11.4 Hz), 3.22 (t, 2H, J=7.3 Hz), 2.70 (brt, 2H, J=12.5 Hz), 1.78 (q, 2H, J=6.9 Hz), 1.47–1.68 (m, 3H), 1.46 (s, 9H), 1.12 (ddd, 2H, J=24.3 Hz), J=12.9 Hz, J=4.3 Hz).

e) 4-[3-[1,2-Benzisoxazol-3-yl]-propyl]-1-piperidinecarboxylic acid, 1-(1,1-dimethylethyl)ester The procedure described in Example 1d was followed with 3-methyl-1,2-benzisoxazole (0.412 g, 3.09 mmol), the iodide obtained in step d (1.15 g, 3.4 mmol), and 1M LDA (3.4 mL, 3.4 mmol) in THF (8 mL). After purification, the title compound (0.694 g, 65%) was obtained as pale yellow oil.

$^1$H-NMR (CDCl$_3$) δ 7.65 (d, 1H, J=8.0 Hz), 7.54–7.57 (m, 2H), 7.27–7.34 (m, 1H), 4.08 (brd, 2H, J=12.5 Hz), 2.99 (t, 2H, J=7.6 Hz), 2.66 (brt, 2H, J=12.0 Hz), 1.86–1.92 (m, 2H), 1.63–1.68 (m, 4H), 1.45 (s, 9H), 1.36–1.45 (m, 1H), 1.06–1.12 (m, 2H).

f) 3-[3-[1-(Phenylmethyl)-4-piperidyl]propyl]-1,2-benzisoxazole maleate

The procedure described in Example 1e was followed with piperidine obtained in step e (0.544 g, 1.58 mmol) and TFA (4 mL) in CH$_2$Cl$_2$ (16 mL), and triethylamine (1.1 mL, 7.9 mmol) and benzyl bromide (0.21 mL, 1.74 mmol) in CH$_2$Cl$_2$ (10 mL) for 7.25 hours. Purification by chromatography (2→5% MeOH—CH$_2$Cl$_2$) gave the title compound, free base (0.285 g, 54%) as a pale yellow oil.

The maleate salt was prepared by adding maleic acid (0.109 g, 0.94 mmol) dissolved in the minimum amount of EtOH to a solution of the free base (0.285 g, 0.85 mmol) in CH$_2$Cl$_2$ (10 mL). After concentrating, the residue was purified by recrystallization (EtOAc) to give the title compound (0.292 g, 76%) as an off-white solid.

M.p.: 134.5–135.5.

$^1$H-NMR (DMSO-d$_6$) δ 7.90 (d, 1H, J=7.9 Hz), 7.61–7.72 (m, 2H), 7.47 (s, 5H), 7.38 (t, 1H, J=7.3 Hz), 6.04 (s, 2H), 4.26 (br s, 2H), 3.22–3.45 (m, 2H), 2.99 (t, 2H, J=7.4 Hz), 2.70–2.96 (m, 2H), 1.70–1.90 (m, 4H), 1.40–1.65 (m, 1H), 1.20–1.40 (m, 4H).

$^{13}$C-NMR (DMSO-d$_6$) δ 167.2, 162.2, 158.4, 135.8, 131.2, 130.3, 129.5, 128.9, 123.5, 122.1, 121.2, 109.7, 59.3, 51.7, 34.8, 32.6, 28.9, 24.5, 24.1.

IR (KBr) 2942, 1705, 1581, 1460, 1359 cm$^{-1}$.

EIMS: 334 (M+, free base), 243, 202, 173 (base), 91.

Anal. calc'd. for C$_{22}$H$_{26}$N$_2$O.C$_4$H$_4$O$_4$: C, 69.31; H, 6.71; N, 6.22. Found: C, 69.11; H, 6.64; N, 6.46.

EXAMPLE 24 trans-3-[2-[1-(Phenylmethyl)-4-piperidyl]ethenyl]-1,2-benzisoxazole maleate

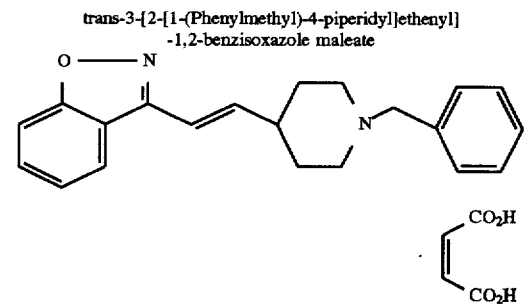

NaH (60% mineral oil dispersion, 0.10 g, 2.51 mmol) was added to a mixture of 3-triphenylphosphoniummethyl-1,2-benzisoxazole bromide (1.19 g, 2.51 mmol) in THF (10 mL). After stirring at room temperature for 1 hour, a solution of 4-carboxaldehyde-1-phenylmethylpiperidine (0.51 g, 2.51 mmol) in THF (2 mL) was added. The mixture obtained was stirred for 4 hours and filtered. The filtrate was concentrated and the residue was partitioned between diethyl ether and H$_2$O. The separated organic layer was dried (MgSO$_4$), filtered, and concentrated. Purification by silica gel flash chromatography (40% EtOAc-hexanes) gave the title compound, free base (0.483 g, 60%) as a colorless oil.

The maleate salt was prepared by adding maleic acid (0.194 g, 1.67 mmol) dissolved in the minimum amount of EtOH to a solution of the free base (0.483 g, 1.52 mmol) in Et$_2$O (25 mL). The white solid obtained was collected by filtration to give the title compound (0.581 g, 88%).

M.p.: 174°–175° C.

$^1$H-NMR (DMSO-d$_6$) δ 8.16 (d, 1H, J=7.8 Hz), 7.75 (d, 1H, J=8.4 Hz), 7.67 (t, 1H, J=8.2 Hz), 7.41–7.55 (m, 6H), 6.96 (br dd, 1H, J=16.5 Hz, J=5.6 Hz), 6.78 (d, 1H, J=16.5 Hz), 6.08 (s, 2H), 4.33 (s, 2H), 3.32–3.39 (m, 2H), 2.95–3.15 (m, 2H), 2.50–2.70 (m, 1H), 2.06 (br d, 2H, J=12.6 Hz), 1.60–1.90 (m, 2H).

$^{13}$C-NMR (DMSO-d$_6$) δ 167.3, 162.7, 154.9, 142.7, 135.9, 131.2, 130.4, 130.2, 129.5, 128.9, 124.2, 122.7, 119.4, 116.5, 109.9, 59.2, 51.0, 36.2, 27.8.

IR (KBr) 3035, 2944, 1708, 1588, 1472, 1360 cm$^{-1}$.

EIMS: 3.18 (M+, free base), 201, 227, 172, 91 (base).

Anal. Calc'd. for C$_{21}$H$_{22}$N$_2$O.C$_4$H$_4$O$_4$: C, 69.11; H, 6.03; N, 6.45. Found: C, 69.04; H, 6.27; N, 6.38.

EXAMPLE 25

3-[2-[1-(Phenylmethyl)-4-piperazinyl]ethyl]-1,2-benzisoxazole dihydrochloride salt

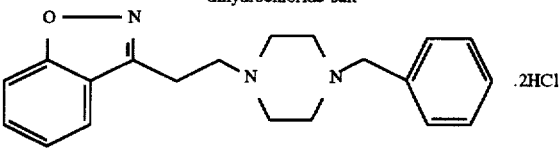

A mixture of 3-(2-chloroethyl)-1,2-benzisoxazole (0.55 g, 3.03 mmol) and N-benzylpiperazine (1.06 mL, 6.06 mmol) in xylene (4 mL) was heated at 150° C. for 4.75 hours. The cooled mixture was diluted with CH$_2$Cl$_2$ and washed with H$_2$O. The organic layer was dried (MgSO$_4$), filtered and concentrated. Purification by silica gel flash chromatography (50% EtOAc-hexanes→100% EtOAc) gave the title compound, free base (0.337 g, 35%) as a pale yellow oil.

The dihydrochloride salt was made by bubbling excess hydrogen chloride through a solution of the free base (0.337 g, 1.05 mmol) in Et$_2$O (50 mL). The white solid formed was collected by filtration to give the title compound (0.259 g, 63%).

M.p.: 233°–234° C.

$^1$H-NMR (D$_2$O) δ 7.79 (d, 1H, J=8.0 Hz), 7.53–7.69 (m, 2H), 7.50 (s, 5H), 7.40 (ddd, 1H, J=7.9 Hz, J=6.6 Hz, J=1.3 Hz), 4.47 (s, 2H), 3.82 (t, 2H, J=7.5 Hz), 3.60–3.80 (m, 8H), 3.55 (t, 2H, J=7.5 Hz).

$^{13}$C-NMR (D$_2$O) δ 165.5, 158.0, 134.1, 133.6, 132.4, 130.3, 127.1, 124.4, 123.2, 112.8, 63.4, 56.6, 51.8, 51.0, 23.2.

IR (KBr) 2989, 1608, 1436, 1375 cm$^{-1}$.

EIMS: 321 (M+, free base), 256, 189, 91 (base).

Anal. Calc'd. for C$_{20}$H$_{23}$N$_3$O.2HCl: C, 60.92; H, 6.39; N, 10.66. Found: C, 60.64; H, 6.57; N, 10.42.

EXAMPLE 26

5,7-Dihydro-7-methyl-3-[2-[1-(phenylmethyl)-4-piperidinyl]ethyl]-6H-pyrrolo[4,5-fl-1,2-benzisoxazole-6-one mesylate

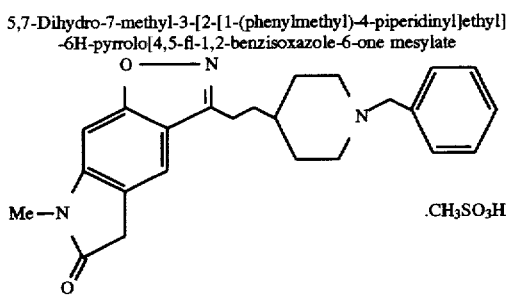

NaH (60% mineral oil dispersion, 0.048 g, 1.2 mmol) was added to a solution of 5,7-dihydro-3-[2-[1-(phenylmethyl)-4-piperidinyl]ethyl]-6H-pyrrolo[4,5-f]-1,2-benzisoxazole-6-one (0.374 g, 1.0 mmol) in DMF (10 mL) at room temperature. After evolution of hydrogen gas had subsided, methyl iodide (0.093 mL, 1.5 mmol) was added and the mixture obtained was stirred for 5.5 hours. Saturated $NH_4Cl$ and $H_2O$ (>50 mL) were added. The reaction was extracted with $CH_2Cl_2$ and the organic layer was dried ($MgSO_4$), filtered, and concentrated. Purification by silica gel flash chromatography ($CH_2Cl_2 \rightarrow 3\%$ MeOH—$CH_2Cl_2$) gave the title compound, free base (0.056 g, 14%) as an off-white foam.

The mesylate salt was made by adding methanesulfonic acid (0.009 mL, 0.144 mmol) to a solution of the free base (0.056 g, 0.044 mmol) in $CH_2Cl_2$ (5 mL). After concentration, the residue was triturated from $Et_2O$ to give the title compound (0.049 g, 70%) as an off-white solid.

M.p.: 164°–165° C. (dec).

$^1$H-NMR (DMSO-$d_6$) 7.69 (s, 1H), 7.49 (s, 5H), 7.32 (s, 1H), 4.28 (s, 2H), 3.64 (s, 2H), 3.35 (br d, 2H, J=11.6 Hz), 3.18 (s, 3H), 2.85–2.99 (m, 4H), 2.30 (s, 3H), 1.95 (br d, 2H, J=12.9 Hz), 1.66–1.80 (m, 2H), 1.45–1.60 (m, 1H), 1.35–1.44 (m, 2H).

EIMS: 389 (M+, free base), 298, 217, 200, 185 (base), 172.

HRMS Calc'd. for $C_{24}H_{27}N_3O_2 \cdot CH_3SO_3H$: 389.2104. Found: 389.2075.

EXAMPLE 27

5,7-Dihydro-7-ethyl-3-[2-[1-(phenylmethyl)-4-piperidinyl]ethyl]-6H-pyrrolo[4,5-fl-1,2-benzisoxazol-6-one mesylate

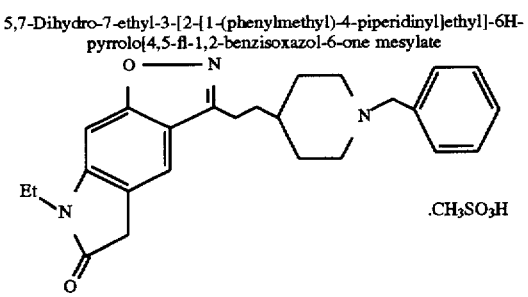

The procedure described in Example 26 was followed with 5,7-dihydro-3-[2-[1-(phenylmethyl)-4-piperidinyl]ethyl]-6H-pyrrolo[4,5-f]-1,2-benzisoxazol-6-one (0.374 g, 1.0 mmol), NaH (0.068 g, 1.7 mmol), and ethyl iodide (0.16 mL, 2.0 mmol) in DMF (10 mL). After purification, the title compound, free base (0.076 g, 19%) was obtained as a pale yellow oil.

The mesylate salt was made by adding methanesulfonic acid (0.007 mL, 0.112 mmol) to a solution of the free base (0.045 g, 0.112 mmol) in $CH_2Cl_2$ (5 mL). After concentration, the residue was triturated from $Et_2O$ to give the title compound (0.042 g, 75%) as an off-white solid (hygroscopic).

M.p.: ~162+ C. (dec at >60° C.)

$^1$H-NMR (DMSO-$d_6$) δ 7.69 (s, 1H), 7.48 (s, 5H), 7.39 (s, 1H), 4.27 (s, 2H), 3.77 (br q, 2H, J=7.1 Hz), 3.64 (s, 2H), 3.34–3.39 (m, 2H), 2.92–2.98 (m, 4H), 2.30 (s, 3H), 1.94 (br d, 2H, J=12.8 Hz), 1.66–1.78 (m, 2H), 1.30–1.60 (m, 3H), 1.16 (t, 3H, J=7.1 Hz).

$^{13}$C-NMR (DMSO-$d_6$) 174.5, 163.2, 158.1, 147.0, 131.4, 131.0, 129.8, 129.6, 128.9, 121.2, 117.0, 115.2, 90.0, 59.3, 51.6, 34.5, 34.4, 33.0, 32.6, 28.5, 21.6, 12.3.

IR (KBr) 2934, 1716, 1630, 1605, 1466, 1330 cm$^{-1}$.

EIMS 403 (M+, free base), 386, 312, 185 (base), 172.

HRMS Calc'd. for $C_{25}H_{29}N_3O_2 \cdot CH_3SO_3H$: 403.22605. Found: 403.22761.

EXAMPLE 28

5,7-Dihydro-3-[2-[1-(2-chloro-5-thiophenemethyl)-4-piperidinyl]ethyl]-6H-pyrrolo[4,5-fl-1,2-benzisoxazol-6-one

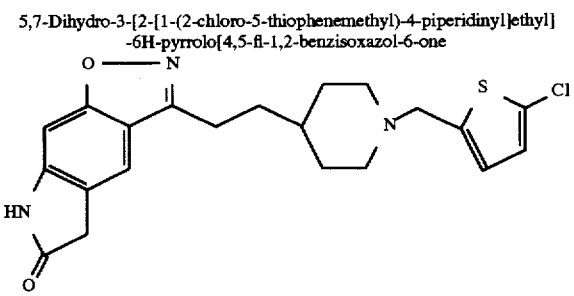

The procedure described in Example 12f was followed with 4-[2-[5,7-dihydro-6H-pyrrolo[4,5-f]-1,2-benzisoxazol-6-one-3-yl]ethyl]-1-piperidinecarboxylic acid, 1-(1,1-dimethylethyl)ester (0.328 g, 0.851 mmol) and TFA (2 mL) in $CH_2Cl_2$ (8 mL). Only a portion of the crude salt was utilized in the alkylation step: $Na_2CO_3$ (0.175 g, 1.66 mmol) and 2-chloro-5-chloromethylthiophene (0.048 mL, 0.40 mmol) in DMF (3 mL). After purification (2–4% MeOH—$CH_2Cl_2$), the title compound (0.0514 g, 43%) was obtained as a white solid.

M.p.: 202°–204° C. (dec)

$^1$H-NMR (DMSO-$d_6$) δ 10.8 (s, 1H), 7.62 (s, 1H), 6.97 (s, 1H), 6.92 (d, 1H, J=3.7 Hz), 6.80 (d, 1H, J=3.7 Hz), 3.57 (s, 2H), 3.55 (s, 2H), 2.81–2.93 (m, 4H), 1.91 (br t, 2H, J=10.7 Hz), 1.61–1.71 (m, 4H), 1.11–1.23 (m, 3H).

$^{13}$C-NMR (DMSO-$d_6$) δ 176.7, 162.9, 158.3, 146.5, 142.8, 127.0, 126.1, 125.1, 123.2, 117.1, 115.1, 90.1, 57.0, 53.0, 35.0, 34.8, 33.9, 31.6, 21.9.

IR (KBr) 3174, 2950, 1702, 1631, 1453, 1330 cm$^{-1}$.

EIMS: 398, 382, 350, 322, 236, 172, 91, 81 (base).

HRMS calc'd. for $C_{21}H_{22}ClN_3O_2S$: 415.1122. Found: 415.1085.

Anal. Calc'd. for $C_{21}H_{22}ClN_3O_2S \cdot 0.5H_2O$: C, 59.36; H, 5.46; N, 9.89. Found: C, 59.21; H, 5.12; N, 9.65.

EXAMPLE 29

5,7-Dihydro-3-[2-[1-(2-methyl-4-thiazolemethyl)-4-piperidinyl]ethyl]-6H-pyrrolo[4,5-f]-1,2-benzisoxazol-6-one

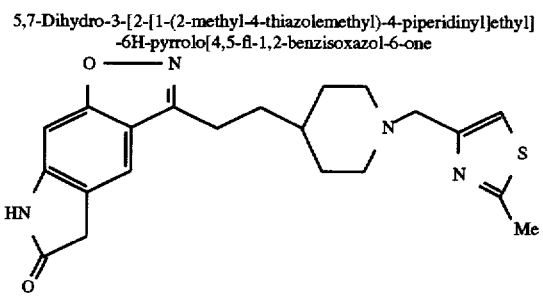

The procedure described in Example 12f was followed with 4-[2-[5,7-dihydro-6H-pyrrolo[4,5-f]-1,2-benzisoxazol-6-one-3-yl]ethyl]-1-piperidinecarboxylic acid, 1-(1,1-dimethylethyl)ester (0.367 g, 0.952 mmol) and TFA (2.5 mL) in $CH_2Cl_2$ (10 mL), and $Na_2CO_3$ (1.01 g, 9.52 mmol) and 4-chloromethyl-2-methylthiazole hydrochloride salt (0.210 g, 1.142 mmol) in DMF (10 mL). Purification by chromatography (4% MeOH-EtOAc) followed by recrystallization (EtOAc-hexanes) gave the title compound (0.074 g, 20%) as a white solid.

M.p.: 172°–173° C. (dec.)

$^1$H-NMR (CDCl$_3$) δ 9.40 (br s, 1H), 7.41 (s, 1H), 7.05 (s, 1H), 7.02 (s, 1H), 3.72 (s, 2H), 3.61 (s, 2H), 3.07 (brd, 2H, J=11.3 Hz), 2.93 (t, 2H, J=7.8 Hz), 2.69 (s, 3H), 2.15 (brt, 2H, J=10.8 Hz), 1.76–1.85 (m, 4H), 1.42–1.55 (m, 3H).

$^{13}$C-NMR (CDCl$_3$) δ 177.4, 166.0, 163.6, 158.3, 151.7, 145.1, 122.2, 116.9, 116.8, 116.3, 91.5, 57.8, 53.4, 35.4, 34.8, 34.0, 31.2, 22.5, 19.2.

IR (KBr) 3101, 3015, 2938, 2924, 1713, 1633, 1456, 1328 cm$^{-1}$.

EIMS: 396 (M+), 379, 284, 267, 206 (base).

HRMS calc'd. for $C_{21}H_{24}N_4O_2S$: 396.1621. Found: 396.1631.

EXAMPLE 30

3-[2-[1-(3-Bromophenylmethyl)-4-piperidinyl]ethyl]-5,7-dihydro-6H pyrrolo[4,5-f]-1,2-benzisoxazol-6-one

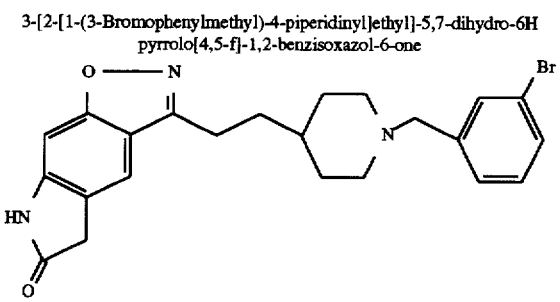

The procedure described in Example 12f was followed with 4-[2-[5,7-dihydro-6H-pyrrolo[4,5-f]-1,2-benzisoxazol-6-one-3-yl]ethyl]-1-piperidinecarboxylic acid, 1-(1,1-dimethylethyl)ester (0.50 g, 1.30 mmol) and TFA (3 mL) in $Ch_2Cl_2$ (12 mL), and $Na_2CO_3$ (0.689 g, 6.5 mmol) and 3-bromobenzyl bromide (0.46g, 1.84 mmol) in DMF (20 mL). Purification aby chromatography ($CH_2Cl_2 \rightarrow 5\%$ MeOH—$CH_2Cl_2$) gave the title compound (0.314 g, 53%) as a pale yellow solid. Recrystallization (EtOAc, twice) gave a white solid (0.076 g, 13%).

M.p.: 173°–174° C.

$^1$H-NMR (CDCl$_3$) δ 8.77 (s, 1H), 7.47 (s, 1H), 7.41 (s, 1H), 7.36 (d, 1H, J=7.7 Hz), 7.23 (d, 1H, J=7.9 Hz), 7.16 (t, 1H, J=7.7 Hz), 7.00 (s, 1H), 3.61 (s, 2H), 3.46 (s, 2H), 2.86–2.96 (m, 4H), 1.90–2.02 (m, 2H), 1.70–1.85 (m, 4H), 1.30–1.42 (m, 3H).

$^{13}$C-NMR (CDCl$_3$) δ 177.1, 163.5, 158.4, 144.7, 132.0, 130.1, 129.8, 127.8, 122.3, 122.0, 116.9, 116.5, 91.5, 62.6, 53.6, 35.3, 35.2, 34.3, 31.9, 22.6.

EXAMPLE 31

3-[2-[1-(4-Bromophenylmethyl)-4-piperidinyl]ethyl]-5,7-dihydro-6H-pyrrolo[4,5-f]-1,2-benzisoxazol-6-one

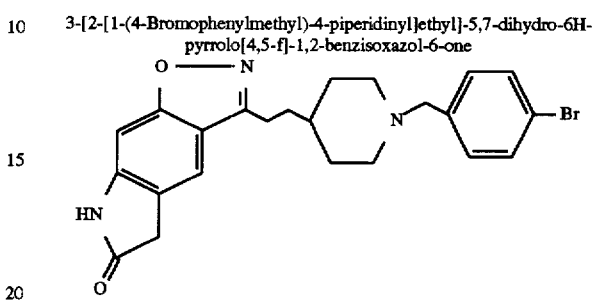

The procedure described in Example 12f was followed with 4-[2-[5,7-dihydro-6H-pyrrolo[4,5-f]-1,2-benzisoxazol-6-one-3-yl]ethyl]-1-peperidinecarboxylic acid, 1-(1,1-dimethyl-ethyl)ester (0.50 g, 1.3 mmol) and TFA (3 mL) in $CH_2Cl_2$ (12 mL), and $Na_2CO_3$ (0.689 g, 6.5 mmol) and 4-bromobenzyl bromide (0.39 g, 1.56 mmol) in DMF (15 mL). Purification by chromatography ($CH_2Cl_2 \rightarrow 5\%$ MeOH—$CH_2Cl_2$) gave the title compound (0.415 g, 70%) as an off-white solid.

M.p.: 177°–178° C.

$^1$H-NMR (CDCl$_3$) δ 9.98 (br s, 1H), 7.37–7.40 (m, 3H), 7.16 (d, 2H, J=8.2 Hz), 6.99 (s, 1H), 3.60 (s, 2H), 3.42 (s, 2H), 2.87–2.94 (m, 4H), 1.94 (brt, 2H, J=10.5 Hz), 1.65–1.80 (m, 4H), 1.20–1.35 (m, 3H).

$^{13}$C-NMR (CDCl$_3$) δ 178.1, 163.5, 158.4, 145.2, 137.3, 131.2, 130.8, 122.2, 120.7, 116.7, 116.3, 91.5, 62.5, 53.5, 35.5, 35.2, 34.2, 31.9, 22.5.

EXAMPLE 32

5,7-Dihydro-3-[3-[1-(phenylmethyl)-4-piperidinyl]-propyl]-6H-pyrrolo[4,5-f]-1,2-benzisoxazol-6-one

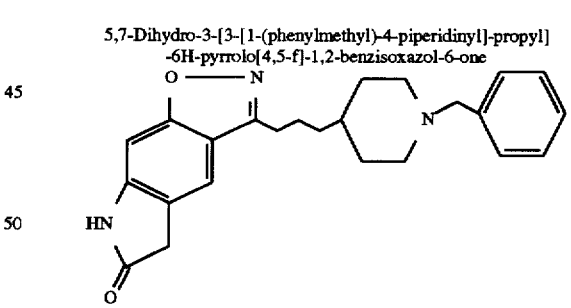

a) 4-[3-[5,7-Dihydro-6H-pyrrolo[4,5-f]-1,2-benzisoxazol-6-one-3-yl]propyl]-1-piperidinecarboxylic acid, 1-(1,1-dimethylethyl)ester The procedure described in Example 7a was followed with 5,7-dihydro-3-methyl-6H-pyrrolo[4,5-f]-1,2-benzisoxazol-6-one (0.13 g, 0.69 mmol), 1M LDA (2.8 mL, 2.8 mmol), and 4-iodoethyl-1-piperidinecarboxylic acid, 1-(1,1-dimethylethyl)ester (0.233 g, 0.69 mmol) in dry THF (14 mL), except that after addition of reagents, the mixture was stirred at −78° C. for 4 hours. Purification by chromatography (10% →50% EtOAc—$CH_2Cl_2$) gave recovered starting material (0.031 g, 24%) and the title compound (0.129 g, 47%) as a colorless oil.

¹H-NMR (CDCl₃) δ 9.50 (s, 1H), 7.42 (s, 1H), 7.04 (s, 1H), 4.06 (brd, 2H, J=14.5 Hz), 3.62 (s, 2H), 2.91 (t, 2H, J=7.5 Hz), 2.66 (dt, 2H, J=13.0 Hz, J=2.0 Hz), 1.81–1.87 (m, 2H), 1.65 (brd, 2H, J=12.3 Hz), 1.44 (s, 9H), 1.34–1.43 (m, 3H), 1.09–1.20 (m, 2H).

b) 5,7-Dihydro-3-[3-[1-(phenylmethyl)-4-piperidinyl]propyl]-6H-pyrrolo[4,5-f]-1,2-benzisoxazol-6-one The procedure described in Example 12f was followed with the piperidine obtained in step a (0.114 g, 0.29 mmol) and TFA (1.5 mL) in CH₂Cl₂ (6 mL), and Na₂CO₃ (0.154 g, 1.45 mmol) and benzyl bromide (0.042 mL, 0.35 mmol) in DMF (5 mL). Purification by chromatography (CH₂Cl₂→5% MeOH—CH₂Cl₂) gave the title compound (0.070 g, 62%) as a white foamy solid. Recrystallization (CH₂Cl₂) gave a white solid (0.054 g, 48%)

M.p.: 164°–166° C.

¹H-NMR (CDCl₃) δ 9.73 (br s, 1H), 7.41 (s, 1H), 7.24–7.34 (m, 5H), 6.99 (s, 1H), 3.61 (s, 2H), 3.56 (s, 2H), 2.86–2.97 (m, 4H), 1.97–2.05 (m, 2H), 1.76–1.88 (m, 2H), 1.65–1.70 (m, 2H), 1.26–1.38 (m, 5H).

¹³C-NMR (CDCl₃) 177.7, 163.6, 158.3, 145.2, 129.5, 128.3, 127.3, 122.2, 116.8, 116.4, 91.6, 63.2, 53.6, 36.1, 35.5, 35.3, 31.9, 25.4, 25.0.

IR (KBr) 3150, 3096, 2930, 1705, 1634, 1495, 1345 cm⁻¹.

EIMS 389 (M+), 372, 298, 202, 172, 108, 91 (base).

HRMS calc'd. for C₂₄H₂₇N₃O: 389.2104. Found: 389.2107.

EXAMPLE 33

3-[2-[1-(Phenylmethyl)-4-piperidinyl]ethyl]-5,6,8-trihydro-7H-isoxazolo[4,5-g]quinolin-7-one

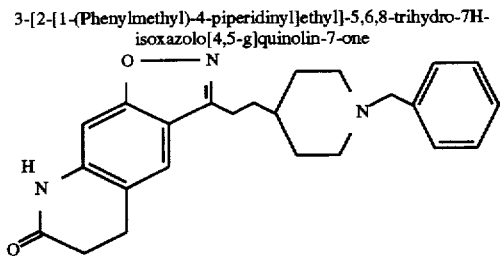

a) 6-Acetyl-3,4-dihydro-7-hydroxy-2H-quinolin-2-one

Acetyl chloride (2.0 mL, 28.1 mmoL) was added to a mixture of 3,4-dihydro-7-methoxy-2H-quinolin-2-one (1.99 g, 11.2 mmol) in 1,2-dichloroethane (30 mL). The mixture obtained was cooled to 0° C. and AlCl₃ (6.0 g, 44.98 mmol) was added in portions. The mixture was heated to reflux for 2 hours. The reaction was cautiously poured over ice-H₂O, stirred for a minimum of 1 hour (to overnight), and extracted with CH₂Cl₂. The organic layer was washed with brine, dried (MgSO₄), filtered, and concentrated to give the title compound (1.89 g, 82%) as an off-white solid.

¹H-NMR (DMSO-d₆) δ 12.4 (s, 1H), 10.4 (s, 1H), 7.74 (s, 1H), 6.38 (s, 1H), 2.86 (t, 2H, J=7.4 Hz), 2.56 (s, 3H1), 2.46–2.56 (m, 2H).

b) 6-Acetyl-3 4-dihydro-7-hydroxy-2H-quinolin-2-one, 6-oxime

An aqueous solution of hydroxylamine hydrochloride (1.47 g, 21.2 mmol) and sodium acetate trihydrate (3.0 g, 22.1 mmoL) was added to a mixture of the ketone obtained in step a (1.89 g, 9.2 mmol) in EtOH (100 mL). The mixture obtained was heated to reflux for 4 hours. The reaction was concentrated, and the residue was stirred with H₂O. The solid obtained was collected by filtration, and rinsed with EtOH and Et₂O to give the title compound (1.67 g, 82%) as an off-white solid.

M.p.: 286.5°–287.7° C. (dec).

¹H-NMR (DMSO-d₆) δ 11.7 (s, 1H), 11.3 (s, 1H), 10.1 (s, 1H), 7.28 (s, 1H), 6.37 (s, 1H), 2.81 (t, 2H, J=7.5 Hz), 2.43 (t, 2H, J=7.5 Hz), 2.21 (s, 3H).

c) 6-Acetyl-3 4-dihydro-7-hydroxy-2H-quinolin-2-one, 6-oxime acetate

A heterogenous mixture of the oxime obtained in step b (1.67 g, 7.57 mmol) in acetic anhydride (13 mL) was heated at 80° C. for 1.5 hours. The reaction mixture was concentrated, and excess acetic anhydride was removed by concentrating from toluene. After drying, the title compound (1.7 g, 86%) was obtained as an off-white solid.

¹H-NMR (DMSO-d₆) δ 11.0 (s, 1H), 10.2 (s, 1H), 7.36 (s, 1H), 6.44 (s, 1H), 2.82 (t, 2H, J=7.5 Hz), 2.45 (t, 2H, J=7.5 Hz), 2.38 (s, 3H), 2.22 (s, 3H).

d) 5,6,8-Trihydro-7H-isoxazolo[4,5-g]quinolin-7-one

A mixture of the oxime acetate obtained in step c (1.58 g, 6.02 mmol) and pyridine (4.9 mL, 60.2 mmol) in DMF (75 mL) was heated in 125°–130° C. for 2 hours. The reaction was concentrated in vacuo and the residue obtained was purified by recrystallization (EtOAc) to give the title compound (0.80 g, 66%) as a pale yellow solid.

M.p.: 309°–311° C. (dec).

¹H-NMR (DMSO-d₆) δ 10.4 (s, 1H), 7.62 (s, 1H), 7.02 (s, 1H), 2.99 (t, 2H, J=7.4 Hz), 2.49–2.53 (m, 2H), 2.47 (s, 3H).

e) 4-[2-[5,6,8-Trihydro-7H-isoxazolo[4,5-g]quinolin-7-one-3-yl]ethyl]-1-piperidinecarboxyl acid, 1-(1,1-dimethylethyl) ester The procedure described in Example 7a was followed with the benzisoxazole obtained in step d (0.47 g, 2.3 mmol), 1M LDA (8.1 mL, 8.1 mmol), and 4-iodomethyl-1-piperidinecarboxylic acid, 1-(1,1-dimethylethyl)ester (0.75 g, 2.3 mmol) in dry THF (150 mL), except that after addition of reagents, the mixture was stirred at −78° C. for 3.5 hours. An additional reaction was benzisoxazole obtained in step d (0.206 g, 1.02 mmol) was carried out in the same manner. Crude product from both reactions was combined and purification by chromatography (EtOAc) gave the title compound (0.72 g, 54% as a white solid.

¹H-NMR (DMSO-d₆) δ 10.4 (s, 1H), 7.67 (s, 1H), 7.02 (s, 1H), 3.93 (brd, 2H, J=13.4 Hz), 2.89–3.31 (m, 4H), 2.57–2.75 (brm, 2H), 2.49–2.53 (m, 2H), 1.64–1.72 (m, 4H), 1.38 (s, 9H), 1.36–1.50 (m, 1H), 1.01–1.16 (m, 2H).

f) 3-[2-[1-(Phenylmethyl)-4-piperidinyl]ethyl]-5,6,8-trihydro-7H-isoxazolo[4,5-g]quinolin-7-one The procedure described in Example 12f was followed with the piperidine obtained in step e (0.55 g, 1.37 mmol) and TFA (3.5 mL) in CH₂CL₂ (14 mL), and Na₂CO₃ (0.758 g, 7.14 mmol) and benzyl bromide (0.23 mL, 1.93 mmol) in DMF (14 mL). After purification by chromatography (5–30% MeOH—CH₂Cl₂), the title compound (0.23 g, 43%) was obtained as a white solid. A sample could be recrystallized from EtOAc—MeOH.

M.p.: 164.4°–165.9° C. ¹H-NMR (CDCl₃) δ 9.37 (s, 1H), 7.38 (s, 1H), 7.22–7.36 (m, 5H), 7.01 (s, 1H), 3.55 (s, 2H), 3.09 (t, 2H, J=7.4 Hz), 2.91–2.97 (m, 4H), 2.70 (t, 2H, J=7.4 Hz), 2.01 (brt, 2H, J=10.3 Hz), 1.75–1.80 (m, 4H), 1.39–1.50 (m, 3H).

¹³C-NMR (CDCl₃) 170.6, 162.0, 158.2, 141.1, 140.9, 128.7, 128.2, 126.8, 121.2, 120.3, 115.7, 94.6, 62.5, 53.2, 34.9, 33.8, 31.6, 30.2, 24.8, 21.9.

IR (KBr) 3172, 3088, 2921, 1694, 1631, 1447, 1381 cm⁻¹.

EIMS 389 (M+), 388, 372, 298, 185, 172, 91 (base).

HRMS Calc'd. for C₂₄H₂₇N₃O₂: 389.2104. Found: 389.2102.

EXAMPLE 34

6,8-Dihydro-3-[2-[1-(phenylmethyl)-4-piperidinyl]-ethyl]-7H-pyrrolo[5,4-g]-1,2-benzisoxazol-7-one

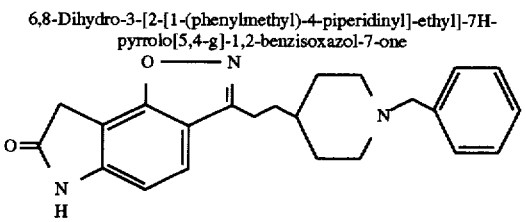

a) 5-Acetyl-1,3-dihydro-4-hydroxy-2H-indol-2-one

An intimate mixture of 4-acetyloxy-1,3-dihydro-2H-indol-2-one (0.876 g, 4.58 mmol) and AlCl₃ (1.83 g, 13.7 mmol) placed in a tear-shape flask was immersed in an oil bath pre-heated to 190° C. and heated for 1 hour. Ice-water was added cautiously to the cooled reaction mixture and stirred for 1.5 hours. Concentrated HCl was added and the mixture was extracted with EtOAc. The organic layer was dried (MgSO₄), filtered, and concentrated. Purification by silica gel flash chromatography (1→3% MeOH—CH₂Cl₂) gave the title compound (0.441 g, 50%) as an off-white solid.

¹H-NMR (DMSO-d₆) δ 12.6 (s, 1H), 10.8 (s, 1H), 7.85 (d, 1H, J=8.4 Hz), 6.49 (d, 1H, J=8.4 Hz), 3.41 (s, 2H), 2.57 (s, 3H).

b) 5-Acetyl-1 3-dihydro-4-hydroxy-2H-indol-2-one, 5-oxime

The procedure described in Example 33b was followed with the ketone obtained in step a (0.40 g, 2.09 mmol), and an aqueous solution of NH₂OH hydrochloride (0.29 g, 4.18 mmol), and NaOAc trihydrate (0.569 g, 4.18 mmol) in EtOH (32 mL). After 3 hours, the mixture was diluted with H₂O and extracted with EtOAc. The organic layer was dried (MgSO₄), filtered, and concentrated to give the title compound (0.436 g, quantitative) as an off-white solid.

¹H-NMR (DMSO-d₆) δ 12.0 (s, 1H), 11.4 (s, 1H), 10.4 (s, 1H), 7.35 (d, 1H, J=8.2 Hz), 6.41 9d, 1H, 8.3 Hz), 3.34 (s, 2H), 2.22 (s, 3H).

c) 5-Acetyl-1,3-dihydro-4-hydroxy-2H-indol-2-one, 5-oxime acetate

The procedure described in Example 33c was followed with the oxime obtained in step b (0.392 g, 1.9 mmol) in Ac₂O (10 mL). The solid obtained was freed from any inorganic salts from previous step by stirring in H₂O. Filtration and drying gave the title compound (0.417 g, 88%) as a red-pinkish solid.

¹H-NMR (DMSO-d₆) δ 11.45 (s, 1H), 10.6 (s, 1H), 7.50 (d, 1H, J=8.2 Hz), 6.49 (d, 1H, J=8.2 Hz), 3.40 (s, 2H), 2.41 (s, 3H), 2.23 (s, 3H).

d) 6,8-Dihydro-3-methyl-7H-pyrrolo[5,4-g]-1,2-benzisoxazol-7-one

The procedure described in Example 33d was followed with the oxime acetate obtained in step c (0.334 g, 1.35 mmol) and pyridine (0.55 mL, 6.75 mmol) in DMF (25 mL). After work-up, the residue was purified by silica gel flash chromatography (50→75% EtOAc-hexanes) to give the title compound (0.086 g, 34%) as a white solid.

M.p.: 259°–260° C. (dec).

¹H-NMR (DMSO-d₆) δ 10.79 (s, 1H), 7.67 (d, 1H, J=8.5 Hz), 6.92 (d, 1H, J=8.3 Hz), 3.73 (s, 2H), 2.49 (s, 3H).

e) 4-[2-[6,8-Dihydro-7H-pyrrolo[5,4-g]-1,2-benzisoxazol-7-one-3-yl]ethyl]-1-piperidinecarbarboxylic acid 1-(1,1-dimethylethyl)ester The procedure described in Example 7a was followed with the benzisoxazole obtained in step d (0.040 g, 0.213 mmol), 1M LDA (0.85 mL, 0.85 mmol), and 4-iodomethyl-1-piperidinecarboxylic acid, 1-(1,1-dimethylethyl)ester (0.078 g, 1.234 mmol) in dry THF (20 mL), except that after addition of reagents, the mixture was stirred at −78° C. for 4 hours. Purification by chromatography (25→45% EtOAc—CH₂Cl₂) gave the title compound (0.042 g, 51%) as a pale yellow solid.

¹-NMR (CDCl₃) δ 8.85 (s, 1H), 7.53 (d, 1H, J=8.1 Hz), 6.95 (d, 1H, J=8.3 Hz), 4.08–4.14 (m, 2H), 3.78 (s, 2H), 2.99 (t, 2H, J=7.8 Hz), 2.68 (brt, 2H, J=12.1 Hz), 1.73–1.84 (m, 4H), 1.46–1.60 (m, 1H), 1.46 (s, 9H), 1.17 (ddd, 2H, J=23.2 Hz, J=12.1 Hz, J=4.3 Hz).

f) 6,8-Dihydro-3-[2-[1-(phenylmethyl)-4-piperidinyl]ethyl]-7H-pyrrolo[5,4-g]-1,2-benzisoxazol-7-one The procedure described in Example 12f was followed with the piperidine obtained in step e (0.042 g, 0.109 mmol) and TFA (1.5 mL) in CH₂Cl₂ (6 mL), Na₂CO₃ (0.058 g, 0.545 mmol) and benzyl bromide (0.016 mL, 0.131 mmol) in DMF (6 mL). After purification by chromatography (1–10% MeOH—CH₂Cl₂), the title compound (0.018 g, 44%) was obtained as an off-white solid.

M.p.: 188°–189° C.

¹H-NMR (CDCl₃) δ 9.59 (s, 1H), 7.51 (d, 1H, J=8.1 Hz), 7.23–7.33 (m, 5H), 6.94 (d, 1H, J=8.2 Hz), 3.77 (s, 2H), 3.56 (s, 2H), 2.93–2.99 (in, 4H), 2.02 (brt, 2H, J=10.7 Hz), 1.75–1.79 (m, 4H), 1.26–1.39 (m, 3H).

¹³C-NMR (CDCl₃) δ 177.2, 158.9, 158.5, 145.0, 129.4, 128.3, 127.2, 121.5, 117.9, 107.1, 105.1, 63.2, 53.5, 35.1, 34.1, 33.8, 31.7, 29.7, 22.5.

EXAMPLE 35

5,7-Dihydro-3-[2-[1-(phenylmethyl)-4-piperidinyl]-ethyl]-6H-pyrrolo[5,4-f]-1,2-benzisoxazol-6-one

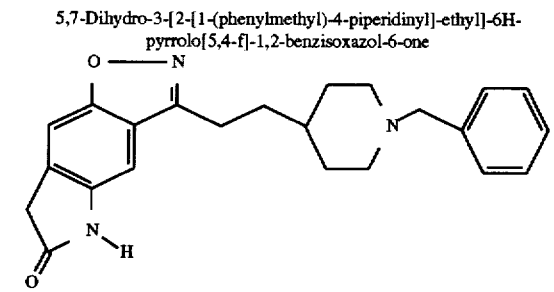

a) 6-Acetyl-1,3-dihydro-5-hydroxy-2H-indol-2-one

The procedure described in Example 33a was followed with 1,3-dihydro-5-methoxy-2H-indol-2-one (4.4 g, 26.96 mmol), acetyl chloride (4.8 mL, 67.41 mmol), and AlCl₃ (14.4 g, 107.8 mmol) in 1,2-dichloroethane (210 mL) for 6 hours. After aqueous work-up and overnight stirring, a precipitate was obtained. This yellow solid was collected by filtration and dried to give the title compound (2.7 g, 52%).

¹H-NMR (DMSO-d₆) δ 12.0 (s, 1H), 10.4 (s, 1H), 7.12 (s, 1H), 6.89 (s, 1H), 3.54 (s, 2H), 2.61 (s, 3H).

b) 6-Acetyl-1,3-dihydro-5-hydroxy-2H-indol-2-one, 6-oxime

The procedure described in Example 33b was followed with the ketone obtained in step a (2.7 g, 14.4 mmol), and an aqueous solution of NH₂OH hydrochloride (2.26 g, 32.5 mmol) and NaOAc trihydrate (4.6 g, 33.9 mmol) in EtOH (155 mL) to give the title compound (2.7 g, 93%) as an off-white solid.

¹H-NMR (DMSO-d₆) δ 11.5 (s, 1H), 11.3 (s, 1H), 10.2 (s, 1H), 6.81 (s, 1H), 6.78 (s, 1H), 3.44 (s, 2H), 2.22 (s, 3H).

c) 6-Acetyl-1,3-dihydro-5-hydroxy-2H-indol-2-one, 6-oxime acetate

The procedure described in Example 33c was followed with the oxime obtained in step b (2.7 g, 13.1 mmol) in Ac₂O (65 mL) for 3 hours to give the title compound (2.93 g, 90%) as an off-white solid.

¹H-NMR (DMSO-d₆) δ 10.4 (s, 1H), 10.2 (s, 1H), 6.86 (s, 1H), 6.81 (s, 1H), 3.48 (s, 2H), 2.37 (s, 3H), 2.22 (s, 3H).

d) 5,7-Dihydro-3-methyl-6H-pyrrolo[5,4-f]-1,2-benzisoxazol-6-one

The procedure described in Example 33d was followed with the oxime acetate obtained in step c (2.75 g, 10.97 mmol) and pyridine (8.9 mL, 109.7 mmol) in DMF (110 m). After concentration in vacuo, the residue was purified by silica gel flash chromatography (2% MeOH—CH₂Cl,) to give the title compound (0.245 g, 12%) as a pastel yellow solid.

¹H-NMR (DMSO-d₆) δ 10.6 (s, 1H), 7.58 (s, 1H), 7.03 (s, 1H), 3.63 (s, 2H), 2.50 (s, 3H).

e) 4-[2-[5,7-Dihydro-6H-pyrrolo[5,4-f]-1,2-benzisoxazol-6-one-3-yl]ethyl]-1-piperidinecarboxylic acid, 1-(1,1-dimethylethyl)ester The procedure described in Example 7a was followed with the benzisoxazole obtained in step d (0.152 g, 0.808 mmol), 1M LDA (3.2 mL, 3.2 mmol), and 4-iodomethyl-1-piperidinecarboxylic acid, 1-(1,1-dimethylethyl)ester (0.315 g, 0.970 mmol) in dry THF (30 mL), except that after addition of reagents, the mixture was stirred at −78° C. for 4.5 hours. Purification by chromatography (50% EtOAc—CH₂Cl₂) gave an inseparable mixture (0.153 g, 1.6:1) of starting material and the title compound, respectively, as a pale yellow soft solid. In a separate experiment, a better ratio (starting material/title compound→1:3) was observed.

¹H-NMR (CDCl₃) δ 9.84 (s, 1H), 7.45 (s, 1H), 7.05 (s, 1H), 4.05–4.15 (m, 2H), 3.69 (s, 2H), 2.96 (t, 2H, J=7.8 Hz), 2.68 (brt, 2H, J=11.8 Hz), 1.72–1.82 (m, 4H), 1.45 (s, 9H), 1.43–1.53 (m, 1H), 1.15 (ddd, 2H, J=23.6 Hz, J=12.1 Hz, J=4.0 Hz).

f) 5,7-Dihydro-3-[2-[1-(phenylmethyl)-4-piperidinyl]ethyl]-6H-pyrrolo[5,4-f]-1,2-benzisoxazol-6-one The procedure described in Example 12f was followed with the mixture obtained in step a (0.153 g) and TFA (1.5 mL) in CH₂Cl₂ (6 mL). Only a portion of the crude salt mixture (0.081 g) was utilized in the alkylation step: Na₂CO₃ (0.041 g, 0.388 mmol) and benzyl bromide (0.012 mL, 0.101 mmol) in DMF (6 mL). Note: For the alkylation step, the solvent (DMF) was thoroughly degassed with Ar and work-up with saturated NaHCO₃ was omitted (brine was used instead). After purification (2–6% MeOH—CH₂Cl₂), the title compound (0.018 g, 60% based on percentage of desired starting material) was obtained as a light yellow solid.

M.p.: 204.5°–205.5° C. (dec).

¹H-NMR (CDCl₃) δ 8.09 (s, 1H), 7.46 (s, 1H), 7.27–7.33 (m, 5H), 6.99 (s, 1H), 3.68 (s, 2H), 3.50–3.52 (m, 2H), 2.90–2.99 (m, 4H), 1.92–2.05 (m, 2H), 1.70–1.80 (m, 4H), 1.30–1.40 (m, 3H).

EXAMPLE 36

3-[2-[1-(Phenylmethyl)-4-piperidinyl]ethyl]-1H-indazole maleate

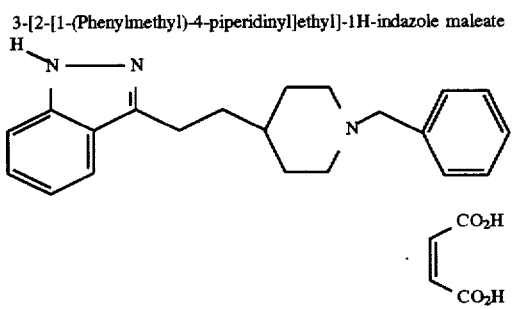

a) 1-(2-Fluorophenyl)-3-[1-(phenylmethyl)-4-piperidinyl]propanone

Lithium hexamethyldisilazide (1M, 14.5 mL, 14.5 mmol) was added to a solution of o-fluoroacetophenone (2.0 g, 14.5 mmol) in THF (100 mL) at −78° C. The mixture obtained was allowed to warm to −20° C. over a 30–60 minute period and then re-cooled to −78° C. A solution of 4-carboxaldehyde-1-piperidinecarboxylic acid, 1-(1,1-dimethylethyl)ester (2.94 g, 14.5 mmol) in THF (20 mL) was added. The mixture was kept at −78° C. for 30 minutes and then allowed to warm to room temperature and stirred for 40 minutes. Saturated NH₄Cl was added and the reaction was extracted with EtOAc. The organic layer was dried (MgSO₄), filtered, and concentrated. Purification by silica gel flash chromatography (30→50% EtOAc—CH₂Cl₂) gave a yellow oil (2.14 g). ¹H-NMR showed mixture of compounds (two major components). Further purification was not attempted. Used as such in next step.

A portion of the mixture obtained above (0.661 g) and PtO₂ (0.070 g, 0.31 mmol) in EtOH was hydrogenated in a Parr shaker at 48 psi (3.31 bars) for 2 hours. The mixture was filtered through a Celite pad and the filtrate was concentrated. An additional reaction with the mixture above (1.00 g) was also carried out. Crude products from these reactions were combined and purified by silica gel flash chromatography (1→3% MeOH—CH₂Cl₂, then 30% EtOAc-hexanes) to give the title compound (0.192 g, 5.3% overall) as a colorless oil.

¹H-NMR (CDCl₃) δ 7.85 (dt, 1H, J=7.6 Hz, J=1.8 Hz), 7.47–7.56 (m, 1H), 7.09–7.33 (m, 7H), 3.49 (s, 2H), 2.95–3.03 (m, 2H), 2.89 (brd, 2H, J=11.4 Hz), 1.94 (brt, 2H, J=11.1 Hz), 1.63–1.77 (m, 4H), 1.24–1.39 (m, 3H).

EIMS: 325 (M+), 202, 188, 172, 91, 66 (base).

b) 3-[2-[1-(Phenylmethyl)-4-piperidinyl]ethyl]-1H-indazole maleate

A mixture of the ketone obtained in step b (0. 178 g, 0.55 mmol) in anhydrous hydrazine (10 mL) was heated to reflux for 3 hours. The reaction was allowed to cool, H₂O was added, and the mixture was extracted with CH₂Cl₂. The organic layer was dried (MgSO₄), filtered, and concentrated. Purification by silica gel radial chromatography (CH₂Cl₂→10% MeOH—CH₂Cl₂) gave the title compound, free base (0.047 g, 27%) as a colorless oil.

The maleate salt was prepared by adding a solution of maleic acid (0.010 g, 0.085 mmol) in Et₂O (5 mL) to a solution of the free base (0.027 g, 0.085 mmol) in Et₂O (75 mL). The white solid obtained was collected by filtration to give the title compound (0.014 g, 38%).

M.p.: 151.5°–152.5° C.

¹H-NMR (DMSO-d₆) δ 12.64 (s, 1H), 7.72 (d, 1H, J=8.0 Hz), 7.44–7.47 (m, 6H), 7.31 (t, 1H, J=7.3 Hz), 7.06 (t, 1H, J=7.4 Hz), 6.02 (s, 2H), 4.24 (br s, 2H), 2.93 (t, 2H, J=7.6 Hz), 1.90–2.00 (m, 2H), 1.60–1.80 (m, 3H), 1.30–1.50 (m, 4H).

We claim:
1. A compound of the formula

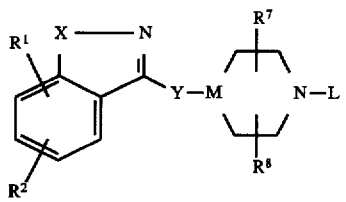

wherein $R^1$ and $R^2$ are attached to adjacent carbon atoms and form, together with the carbon atoms to which they are attached, a group of the formula

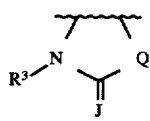

wherein J is oxygen, sulfur or $NR^4$, $R^4$ is hydrogen or $(C_1-C_4)$alkyl, $R^3$ is hydrogen or $(C_1-C_6)$alkyl and Q is $(CH_2)_l$ wherein l is 1;

X is oxygen or sulfur;

Y is $—(CH_2)_m—$, $—CH=CH(CH_2)_n—$, $—NR^4(CH_2)_m—$, or $—O(CH_2)_m—$ wherein $R^4$ is hydrogen or $(C_1-C_4)$ alkyl, n is an integer from 0 to 3 and m is 1 or 2;

$R^5$ and $R^6$ are each independently selected from hydrogen, $(C_1-C_6)$alkyl, phenyl or benzyl, wherein the phenyl moieties of said phenyl and benzyl may optionally be substituted with 1 or 2 substituents independently selected from fluoro, chloro, bromo, iodo, $(C_1-C_4)$ alkyl, trifluoromethyl, $(C_1-C_4)$ alkoxy, cyano, nitro and hydroxy, or $NR^5R^6$ together form a 4 to 5 membered ring wherein one atom of the ring is nitrogen and the others are carbon, oxygen or nitrogen, or $NR^5COR^6$ together form a 4 to 5 membered cyclic lactam ring;

M is —CH—;

L is phenyl, phenyl-$(C_1-C_6)$alkyl, cinnamyl or pyridylmethyl, wherein the phenyl moieties of said phenyl and phenyl-$(C_1-C_6)$alkyl may optionally be substituted with 1-3 substituents independently selected from $(C_1-C_6)$alkyl, $(C_1-C_6)$alkoxy, $(C_1-C_4)$ alkoxycarbonyl, $(C_1-C_4)$alkylcarbonyl, $—OCONR^5R^6$, $—NHCOOR^5$ or halo; or L is a group of the formula

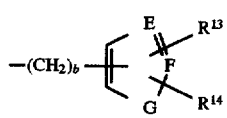

wherein b is an integer from 1 to 4, $R^{13}$ and $R^{14}$ are independently selected from hydrogen, $(C_1-C_4)$ alkyl, halo and phenyl, E and F are independently selected from —CH— and nitrogen, and G is oxygen, sulfur or $NR^4$ wherein $R^4$ is hydrogen or $(C_1-C_4)$alkyl, with the proviso that when E and F are both nitrogen, one of $R^{13}$ and $R^{14}$ is absent; and $R^7$ and $R^8$ are independently selected from hydrogen, $(C_1-C_6)$alkyl, $(C_1-C_6)$alkoxycarbonyl, $(C_1-C_6)$alkylcarbonyl and $(C_1-C_6)$alkoxy, with the proviso that said $(C_1-C_6)$alkoxy is not attached to a carbon that is adjacent to a nitrogen;

or pharmaceutically acceptable salt of such compound.

2. A compound of the formula

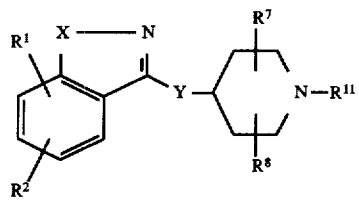

wherein $R^1$ and $R^2$ are attached to adjacent carbon atoms and form, together with the carbon atoms to which they are attached, a group of the formula

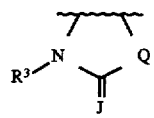

wherein J is oxygen, sulfur or $NR^4$, $R^4$ is hydrogen or $(C_1C_4)$alkyl, $R^3$ is hydrogen or $(C_1-C_6)$alkyl and Q is $(CH_2)_l$ wherein l is 1;

X is oxygen or sulfur;

Y is $—(CH_2)_m—$, $—CH=CH(CH_2)_n—$, $—NR^4(CH_2)_m—$, or $—O(CH_2)_m—$ wherein $R^4$ is hydrogen or $(C_1-C_4)$ alkyl, n is an integer from 0 to 3 and m is an integer from 1 to 3;

$R^5$ and $R^6$ are each independently selected from hydrogen, $(C_1-C_6)$alkyl, phenyl or benzyl, wherein the phenyl moieties of said phenyl and benzyl may optionally be substituted with 1 or 2 substituents independently selected from fluoro, chloro, bromo, iodo, $(C_1-C_4)$ alkyl, trifluoromethyl, $(C_1-C_4)$ alkoxy, cyano, nitro and hydroxy, or $NR^5R^6$ together form a 4 to 5 membered ring wherein one atom of the ring is nitrogen and the others are carbon, oxygen or nitrogen, or $NR^5COR^6$ together form a 4 to 5 membered cyclic lactam ring;

$R^7$ and $R^8$ are independently selected from hydrogen, $(C_1-C_6)$alkyl, $(C_1-C_6)$alkoxycarbonyl, $(C_1-C_6)$alkylcarbonyl and $(C_1-C_6)$alkoxy, with the proviso that said $(C_1-C_6)$alkoxy is not attached to a carbon that is adjacent to a nitrogen; and $R^{11}$ is hydrogen or a nitrogen protecting group.

3. A compound of the formula

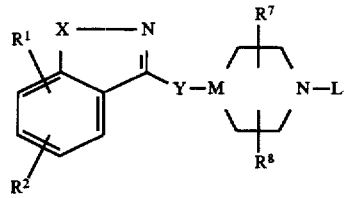

wherein $R^1$ and $R^2$ are independently selected from hydrogen, $(C_1-C_6)$alkoxy, benzyloxy, phenoxy, hydroxy, phenyl, benzyl, halo, nitro, cyano, $COR^5$, $—COOR^5$, $—CONHR^5$, $—NR^5R^6$, $—NR^5COR^6$, $—OCONR^5R^6$, $—NHCOOR^5$, $(C_1-C_6)$alkyl optionally substituted with from 1 to 3 fluorine atoms; $SO_pCH_2$-phenyl or $SO_p(C_1-C_6)$alkyl, wherein p is 0, 1 or 2; pyridylmethyloxy or thienylmethyloxy; 2-oxazolyl, 2-thiazolyl and benzenesulfonamide; wherein the phenyl moieties of said phenoxy, benzyloxy, phenyl, benzyl and benzenesulfonamide groups, the pyridyl and thienyl moieties of said pyridylmetholoxy or thienylmethyloxy and the oxazolyl and thiazolyl moieties of said 2-oxaxolyl and 2-thiazolyl may optionally be substituted with 1 or 2 substituents independently selected from halo, $(C_1-C_4)$alkyl, trifluoromethyl, $(C_1-C_4)$alkoxy, cyano, nitro and hydroxy;

X is sulfur;

Y is $—(CH_2)_m—$, $—CH=CH(CH_2)_n—$, $—NR^4(CH_2)_m—$, or $—O(CH_2)_m—$ wherein $R^4$ is hydrogen or $(C_1-C_4)$ alkyl, n is an integer from 0 to 3 and m is 1 or 2;

$R^5$ and $R^6$ are each independently selected from hydrogen, $(C_1-C_6)$alkyl, phenyl or benzyl, wherein the phenyl moieties of said phenyl and benzyl may optionally be substituted with 1 or 2 substituents independently selected from fluoro, chloro, bromo, iodo, $(C_1-C_4)$ alkyl, trifluoromethyl, $(C_1-C_4)$ alkoxy, cyano, nitro and hydroxy, or $NR^5R^6$ together form a 4 to 5 membered ring wherein one atom of the ring is nitrogen and the others are carbon, oxygen or nitrogen, or $NR^5COR^6$ together form a 4 to 5 membered cyclic lactam ring;

M is $—CH—$;

L is phenyl, phenyl-$(C_1-C_6)$alkyl, cinnamyl or pyridylmethyl, wherein the phenyl moieties of said phenyl and phenyl-$(C_1-C_6)$alkyl may optionally be substituted with 1-3 substituents independently selected from $(C_1-C_6)$alkyl, $(C_1-C_6)$alkoxy, $(C_1-C_4)$ alkoxycarbonyl, $(C_1-C_4)$alkylcarbonyl, $—OCONR^5R^6$, $—NHCOOR^5$ or halo; or L is a group of the formula

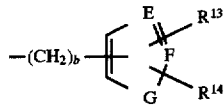 (K)

wherein b is an integer from 1 to 4, $R^{13}$ and $R^{14}$ are independently selected from hydrogen, $(C_1-C_4)$ alkyl, halo and phenyl, E and F are independently selected from $—CH—$ and nitrogen, and G is oxygen, sulfur or $NR^4$ wherein $R^4$ is hydrogen or $(C_1-C_4)$alkyl, with the proviso that when E and F are both nitrogen, one of $R^{13}$ and $R^{14}$ is absent; and $R^7$ and $R^8$ are independently selected from hydrogen, $(C_1-C_6)$alkyl, $(C_1-C_6)$alkoxycarbonyl, $(C_1-C_6)$ alkylcarbonyl and $(C_1-C_6)$alkoxy, with the proviso that said $(C_1-C_6)$alkoxy is not attached to a carbon that is adjacent to a nitrogen;

or pharmaceutically acceptable salt of such compound.

4. A compound according to claim 1, wherein X is oxygen, L is benzyl, Y is $—CH_2—CH_2—$, M is CH, and $R^1$ and $R^2$ form a group of the formula A wherein Q is $CH_2$ and J is oxygen.

5. A compound according to claim 1 that is selected from the group consisting of:

5,7-dihydro-7-methyl-3-[2-[1-(phenylmethyl)-4-piperidinyl]ethyl]-6H-pyrrolo[4,5-f]-1,2-benzisoxazol-6-one;

5,7-dihydro-7-ethyl-3-[2[1-(phenylmethyl)-4-piperidinyl]ethyl]-6H-pyrrolo[4,5-f]-1,2-benzisoxazol-6-one;

5,7-dihydro-3-[2-[1-(2-chloro-5-thiophenemethyl)-4-piperidinyl]ethyl]-6H-pyrrolo[4,5-f]-1,2-benzisoxazol-6-one;

5,7-dihydro-3-[2-[1-(2-methyl-4-thiazolemethyl)-4-piperidinyl]ethyl]-6H-pyrrolo[4,5-f]-1,2-benzisoxazol-6-one;

3-[2-[1-(3-bromophenylmethyl)-4-piperidinyl]ethyl]-5,7-dihydro-6H-pyrrolo[4,5-f]-1,2-benzisoxazol-6-one;

3-[2-[1-(4-bromophenylmethyl)-4-piperidinyl]ethyl]-5,7-dihydro-6H-pyrrolo[4,5-f]-1,2-benzisoxazol-6-one;

5,7-dihydro-3-[3-[1-(phenylmethyl)-4-piperidinyl]propyl]-6H-pyrrolo[4,5-f]-1,2-benzisoxazol-6-one;

6,8-dihydro-3-[2-[1-(phenylmethyl)-4-piperidinyl]ethyl]-7H-pyrrolo[5,4-g]-1,2-benzisoxazol-7-one; and 5,7-dihydro-3-[2-[1-(phenylmethyl)-4-piperidinyl]ethyl]-6H-pyrrolo[5,4-f]-1,2-benzisoxazol-6-one;

or a pharmaceutically acceptable salt of such compound.

6. A pharmaceutical composition for enhancing memory or treating or preventing Alzheimer's disease comprising a compound according to claim 1 and a pharmaceutically acceptable carrier.

* * * * *